(12) United States Patent
Danysz et al.

(10) Patent No.: US 12,239,661 B2
(45) Date of Patent: Mar. 4, 2025

(54) METHODS AND COMPOSITIONS FOR TREATING UNDESIRED IMPLANTED TISSUE FILLER

(71) Applicant: MERZ NORTH AMERICA, INC., Raleigh, NC (US)

(72) Inventors: Wojciech Danysz, Nidderau (DE); Peter Kreymerman, Raleigh, NC (US); Patrick Plitt, Bad Homburg (DE)

(73) Assignee: Merz North America, Inc., Raleigh, NC (US)

( * ) Notice: Subject to any disclaimer, the term of this patent is extended or adjusted under 35 U.S.C. 154(b) by 202 days.

(21) Appl. No.: 17/612,159

(22) PCT Filed: Jun. 3, 2020

(86) PCT No.: PCT/US2020/035881
§ 371 (c)(1),
(2) Date: Nov. 17, 2021

(87) PCT Pub. No.: WO2020/247469
PCT Pub. Date: Dec. 10, 2020

(65) Prior Publication Data
US 2022/0218739 A1  Jul. 14, 2022

Related U.S. Application Data

(60) Provisional application No. 62/949,381, filed on Dec. 17, 2019, provisional application No. 62/858,316, filed on Jun. 6, 2019.

(51) Int. Cl.
| | | |
|---|---|---|
| A61K 33/14 | (2006.01) |
| A61K 8/19 | (2006.01) |
| A61K 8/20 | (2006.01) |
| A61K 8/23 | (2006.01) |
| A61K 8/24 | (2006.01) |
| A61K 8/34 | (2006.01) |
| A61K 8/36 | (2006.01) |
| A61K 8/365 | (2006.01) |
| A61K 8/60 | (2006.01) |
| A61K 9/00 | (2006.01) |
| A61L 27/12 | (2006.01) |
| A61P 17/00 | (2006.01) |
| A61Q 19/08 | (2006.01) |

(52) U.S. Cl.
CPC ............... *A61K 33/14* (2013.01); *A61K 8/19* (2013.01); *A61K 8/20* (2013.01); *A61K 8/23* (2013.01); *A61K 8/24* (2013.01); *A61K 8/345* (2013.01); *A61K 8/36* (2013.01); *A61K 8/365* (2013.01); *A61K 8/60* (2013.01); *A61L 27/12* (2013.01); *A61P 17/00* (2018.01); *A61Q 19/08* (2013.01); *A61K 9/0019* (2013.01); *A61K 2800/884* (2013.01); *A61K 2800/91* (2013.01)

(58) Field of Classification Search
None
See application file for complete search history.

(56) References Cited

U.S. PATENT DOCUMENTS

| 8,808,718 B2 | 8/2014 | Van Der Waal et al. |
| 2017/0079957 A1 | 3/2017 | Chapin et al. |

FOREIGN PATENT DOCUMENTS

| WO | WO 2018/085748 A1 | 5/2018 |
| WO | WO 2019/152964 A1 | 8/2019 |

OTHER PUBLICATIONS

WDCSkin, Radiesse, published Jun. 27, 2016, https://web.archive.org/web/20160627044212/https://www.wdcskin.com/radiesse/ (Year: 2016).*
Berlin et al. (2008) "Calcium hydroxylapatite filler for facial rejuvenation: a histologic and immunohistochemical analysis," Dermatol Surg. 34 (suppl 1): S64-S67.
Halimi et al. (2015) "Chitosan solutions as injectable systems for dermal filler applications: Rheological characterization and biological evidence." 2015 37th Annual International Conference of the IEEE Engineering in Medicine and Biology Society (EMBC), pp. 2596-2599. doi: 10.1109/EMBC.2015.7318923.
International Search Report and Written Opinion, dated Sep. 2, 2020, corresponding to International Application No. PCT/US2020/035881, from which the present application claims priority, 9 pages.
Otsu (1979) "A threshold selection method from gray-level histograms," IEEE Transactions on systems, man and cybernetics, 9: 62-66.
Rabago et al. (2010) "Prolotherapy in Primary Care Practice," Prim Care Clin Office Pract 37, 65-80.
Robinson (Nov. 2018) "In Vitro Analysis of the Degradation of Calcium Hydroxyapatite Dermal Filler: A Proof-of-Concept Study," Dermatologic Surgery 44:S5-S9 (November Special Issue).

(Continued)

*Primary Examiner* — David J Blanchard
*Assistant Examiner* — Edwin Coleman Mitchell
(74) *Attorney, Agent, or Firm* — Leydig, Voit & Mayer, Ltd.

(57) ABSTRACT

A method for treating undesired implanted calcium phosphate tissue filler by administering an effective amount of a pharmaceutically acceptable hyperosmotic composition. The hyperosmotic composition may be hyperosmotic solution, particularly a hyperosmotic aqueous solution. The hyperosmotic composition is administration to an area containing the undesired calcium phosphate tissue filler. Administration of the hyperosmotic composition can reduce, dilute/or redistribute an undesired amount or accumulation of implanted calcium phosphate tissue filler implanted. Methods herein can ameliorate undesired filler that is implanted in an undesired or unintended location, that migrates to an undesired location, that results in an undesired visual result, and/or that results in undesired compression of surrounding tissue, and/or that results in pain, infection, and/or inflammation.

13 Claims, 22 Drawing Sheets

(56) References Cited

OTHER PUBLICATIONS

Robinson (Oct. 2020) "Commentary on the Use of Intralesional Sodium Thiosulfate to Dissolve Facial Nodules From Calcium Hydroxylapatite," Dermatologic Surgery: Oct. 2020—vol. 46—Issue 10—p. 1368-1370. doi: 10.1097/DSS.0000000000002360.
Strazzula et al. (2013) "Intralesional Sodium Thiosulfate for the Treatment of Calciphylaxis," JAMA Dermatol. 149(8):946-949. doi:10.1001/jamadermatol.2013.4565.
Vala et al. (Feb. 2013) "A Review on Otsu Image Segmentation Algorithm," International Journal of Advanced Research in Computer Engineering & Technology (IJARCET) vol. 2, Issue 2, 387-389.
Voigts et al. (2010) "Dispersion of Calcium Hydroxylapatite Accumulations in the Skin: Animal Studies and Clinical Practices," Dermatologic Surgery 36:S1:798-803.

\* cited by examiner

METHODS AND COMPOSITIONS FOR TREATING UNDESIRED IMPLANTED TISSUE FILLER

CROSS-REFERENCE TO RELATED APPLICATIONS

This application is a U.S. National Stage Application filed under 35 U.S.C. § 371 of International Application No. PCT/US2020/035881, filed Jun. 3, 2020 (WO2020/247469), which claims the benefit of priority to U.S. Provisional Patent Applications Nos. 62/858,316, filed Jun. 6, 2019, and 62/949,381, filed Dec. 17, 2019, each of which is incorporated by reference herein in its entirety to the extent not inconsistent with the description herein.

BACKGROUND

The present invention relates to methods and compositions for treating undesired implanted tissue filler implanted in a subject. The methods and composition herein can, for example, be used to reduce the amount of or redistribute tissue filler implanted in a subject. More specifically, methods and compositions herein can be used to dilute the amount of tissue filler at one or more selected in vivo locations. More specifically, the invention relates to using a hyperosmotic aqueous solution to reduce, dilute or redistribute tissue fillers implanted in a subject.

Radiesse® (Merz North America, Inc.) tissue filler is a calcium hydroxyapatite-based soft tissue filler, approved by the FDA for hand augmentation and for treatment of moderate to severe facial wrinkles. Currently, concerns exist regarding the use of Radiesse® treatment due to the lack of an effective method for reversing the treatment. Irreversibility of treatment raises possible safety issues, if inadvertent intravascular injection, overcorrection, vascular compromise, or nodule formation occurs. A particular undesired result of tissue filler use can be development of nodules, or uneven contours that result from improper placement of filler. Such undesired results can occur immediately after implantation or develop over time after implantation. Even in those cases where the tissue filler treatment is fully successful, a subject may wish later wish to reverse the treatment.

Therefore, despite its superior longevity and volume replacement, medical providers and patients have concerns with respect to the use of Radiesse® tissue filler. Trials of using various agents to reduce, redistribute or dissolve Radiesse® tissue filler have been largely unsuccessful. For example, hyaluronidase, which dissolves hyaluronic acid-based fillers, cannot effectively dissolve calcium hydroxyapatite. Additionally, chelating agents targeting divalent cations, such as ethylenediaminetetraacetic acid (EDTA), have also been unsuccessful in reducing the amount of calcium hydroxyapatite.

Voigts, R. et al. (2010) "Dispersion of Calcium Hydroxylapatite Accumulations in the Skin: Animal Studies and Clinical Practices," Dermatologic Surgery 36: S1:798-803 reports a method for dispersing calcium hydroxylapatite by local injection of sterile water or normal saline followed by vigorous massage. Three possible treatments are referenced: massage alone; injection of normal saline into the site followed by massage; or injection of sterile water into the site followed by massage. Injection of sterile water and massage was reported to have the largest effect for dispersing calcium hydroxylapatite. The reference also reports the use of lidocaine injection.

PCT published application WO 2018/085748 9 (published May 11, 2018) reports a pharmaceutical composition containing a thiosulfate or metabisulfite for degrading, dissolving or reducing the level of implanted calcium hydroxyapatite tissue filler and methods employing the composition. The use of 25% (w/v) sodium thiosulfate or 25% (w/v) sodium metabisulfite for degrading, dissolving or reducing the level of implanted calcium hydroxyapatite tissue filler is reported.

Robinson D. (2018) "In Vitro Analysis of the Degradation of Calcium Hydroxyapatite Dermal Filler: Proof-of-Concept Study," Dermatologic Surgery 44: S5-S9 (November Special Issue) reports the results of animal skin sample tests of intralesion injection of purported 25% (w/v) sodium thiosulfate or topical application of purported 25% (w/v) sodium metabisulfite in a gel for dissolution of calcium hydroxyapatite in tissue samples.

There is still a significant need in the art for methods effective for reducing and/or redistributing implanted tissue filler, and particularly for reducing or redistributing calcium hydroxyapatite tissue filler.

SUMMARY

This invention provides a method for treating undesired calcium phosphate tissue filler implanted in a subject comprising the step of administering to the subject an effective amount of a pharmaceutically acceptable hyperosmotic composition. In an embodiment, the composition is a hyperosmotic solution. In an embodiment, the composition is a hyperosmotic aqueous solution. In an embodiment, administration is to an area containing the undesired calcium phosphate tissue filler. In an embodiment, the method relates to reducing, diluting, and/or redistributing an undesired amount or accumulation of calcium phosphate tissue filler implanted in a subject. Undesired amounts of filler include, among others, those amounts that are implanted in an undesired or unintended location, those amounts that migrate to an undesired location, those amounts that result in an undesired visual result (e.g., undesired visible nodules), those amounts that result in undesired compression of surrounding tissue, those amounts that result in pain, those amount that result in infection, or those amounts that result in inflammation.

In embodiments, the osmolality of the composition ranges from 1000 to 5000 milliosmol/Kg. In embodiments, the osmolality of the composition ranges from 2500 to 5000 milliosmol/Kg. In embodiments, the osmolality of the composition ranges from 1000 to 4000 milliosmol/Kg. In embodiments, the osmolality of the composition ranges from 1000 to 3500 milliosmol/Kg. In embodiments, the osmolality of the composition ranges from 1000 to 3000 milliosmol/Kg. In embodiments, the osmolality of the composition ranges from 1000 to 2500 milliosmol/Kg. In embodiments, the osmolality of the composition ranges from 1000 to 2000 milliosmol/Kg. In embodiments, the osmolality of the composition ranges from 1000 to 1500 milliosmol/Kg. In embodiments, the osmolality of the composition ranges from 2000 to 4000 milliosmol/Kg. In embodiments, the osmolality of the composition ranges from 2000 to 3000 milliosmol/Kg. In embodiments, the osmolality of the composition ranges from 2500 to 3500 milliosmol/Kg. In embodiments, the osmolality of the composition ranges from 2500 to 3000 milliosmol/Kg.

In embodiments, the osmolality of the composition is adjusted by the inclusion of one or more tonicity modifying agents. Preferred tonicity modifying agents are those that are pharmaceutically acceptable at the concentration required to achieve the desired osmolality. Preferred tonicity modifying reagents are those that do not induce undesired levels of inflammation or necrosis on administration at the selected osmolarity. Preferred tonicity modifying reagents are those that do not induce undesired levels of skin or injection site irritation or necrosis on administration at the selected osmolality. In more specific embodiments, the one or more tonicity modifying agents are selected from pharmaceutically acceptable salts, pharmaceutically acceptable sugar alcohols, pharmaceutically acceptable sugars and any combinations thereof. It is noted that a given tonicity modifying agent is pharmaceutically acceptable at the concentration in the composition that is needed to achieve the selected osmolality alone or in combination with one or more other tonicity modifying agents.

In specific embodiments, the pharmaceutically acceptable salts are alkali metal salts. In specific embodiments, the pharmaceutically acceptable salts are sodium salts. In specific embodiments, the pharmaceutically acceptable salts are calcium salts. In specific embodiments, the pharmaceutically acceptable salts are magnesium salts. In specific embodiments, the salts are chloride salts. In specific embodiments, the salts are acetate salts. In specific embodiments, the salts are citrate salts. In specific embodiments, the salts are sulfate salts. In specific embodiments, the salts are dihydrogen phosphate salts. In specific embodiments, the salts are phosphate salts. In specific embodiments, the salts are bicarbonate salts (hydrogen carbonate salts). In specific embodiments, the pharmaceutically acceptable salts are alkali metal salts wherein the anion is selected from a halide, a carboxylate, a sulfate, a phosphate, a bicarbonate (hydrogen carbonate) or a dihydrogen phosphate. In specific embodiments, the pharmaceutically acceptable salts are alkali metal salts wherein the anion is selected from acetate or citrate. In specific embodiments, the pharmaceutically acceptable salts are alkali metal salts wherein the anion is selected from chloride, acetate, citrate, sulfate, phosphate, bicarbonate and dihydrogen phosphate. In specific embodiments, the salt is sodium chloride. In specific embodiments, the salt is sodium acetate. In specific embodiments, the salt is sodium citrate. In specific embodiments, the salt is sodium dihydrogen phosphate. In specific embodiments, the salt is magnesium chloride. In specific embodiments, the salt is magnesium sulfate. In specific embodiments, the salt is sodium bicarbonate.

In specific embodiments, the hyperosmotic composition comprises two or more different salts, wherein the total osmolarity of the composition is within one of the hyperosmolar ranges recited herein.

In specific embodiments, the hyperosmotic composition is an aqueous solution and the one or more tonicity modifying salts are water-soluble salts. It is noted that the tonicity modifying salt is soluble in the aqueous solution at the concentrated needed to achieve a desired osmolarity alone or in combination with one or more other selected tonicity modifying agents.

In specific embodiments, sugar alcohols include, among others, glycerol, sorbitol, mannitol, xylitol, isomalt, erythritol or maltitol. In specific embodiments, sugar alcohols include glycerol and mannitol. Sugar alcohols used herein are pharmaceutically acceptable at the concentration used to achieve the desired osmolality alone or in combination with other tonicity modifying agents.

In specific embodiments, sugars are mono- or disaccharides. In specific embodiments, monosaccharides are, among others, glucose, fructose or galactacose. In specific embodiments, disaccharides are sucrose, lactose, or maltose. Sugar alcohols used herein are pharmaceutically acceptable at the concentration used to achieve the desired osmolality alone or in combination with other tonicity modifying agents.

In specific embodiments, the hyperosmotic composition comprises a salt in combination with a sugar or sugar alcohol, at concentrations such that the total osmolality of the composition is within a range of osmolality recited herein.

In specific embodiments, the tonicity modifying agent is other than a salt.

In specific embodiments, the tonicity modifying agent is other than a sugar alcohol.

In specific embodiments, the tonicity modifying agent is other than a monosaccharide.

In specific embodiments, the tonicity reagent is other than a disaccharide.

In specific embodiments, the tonicity modifying agents is other than sodium thiosulfate.

In specific embodiments, the tonicity modifying agent is other than sodium metabisulfite.

In specific embodiments, the tonicity modifying agent is other than calcium chloride.

In embodiments, the hyperosmotic composition is formulated for injection. In embodiments, the hyperosmotic solution is formulated for injection. In embodiments, administration of the hyperosmotic composition is by injection at the location of the undesired accumulation of calcium phosphate tissue filler. This location can be, among others, deep dermal, subdermal, subcutaneous, intramuscular or supraperiosteal. The generic term lesion is used herein to generally describe the location of an undesired amount or an undesired accumulation of calcium phosphate tissue filler implanted in a subject. The term intralesional refers to administration to the lesion, which herein refers to the undesired amount or accumulation of calcium phosphate tissue filler in a subject. In specific embodiments, injection of hyperosmotic composition is by intralesional injection. In specific embodiments, injection of hyperosmotic composition is by deep dermal injection. In specific embodiments, injection of hyperosmotic composition is by subdermal injection. In specific embodiments, injection of hyperosmotic composition is by subcutaneous injection. In specific embodiments, injection of hyperosmotic composition is by intramuscular injection. In specific embodiments, injection of hyperosmotic composition is by supraperiosteal injection.

In embodiments of the methods herein, more than one administration of hyperosmotic composition may be needed to achieve the desired level of improvement desired. More specifically, in embodiments herein, more than one injection of hyperosmotic composition may be needed to achieve the desired amount, location or shape of calcium phosphate tissue filler. Such multiple administrations and/or injections may be made at the same time or separated in time by up to 1-12 hours or up to 1-7 days. In embodiments, multiple administrations and/or injections may be made over a period of several months. Multiple administrations can include injections to different locations. Multiple administrations can include injections at multiple locations within a given lesion. Multiple administrations can include injections of different volumes of the same or different hyperosmotic solutions. Multiple injections can include injections of different hyperosmotic solutions. Multiple injections can include injections of hyperosmotic solutions of different osmolality. Multiple administrations can include administration by means other than injection. Multiple administrations can include administration by injection combined with other means of administration. Other means of administration include those means that can deliver the hyperosmotic composition to the lesion. For example, hyperosmotic compositions and/or solutions can be administered directly to lesions by surgical methods. Preferred means of administration is by injection into the lesion.

The timing of administration of hyperosmotic composition to lesions after implantation of calcium phosphate filler is not critical. In the event that an implantation results in pain or undesired compression of surrounding tissue, it may be beneficial to administer the hyperosmotic composition as soon as possible after implantation or occurrence or recognition of the pain or undesired compression. For example, administration of hyperosmotic composition can be any time after implantation or any time after the discovery of the undesired amount or accumulation of calcium phosphate filler. It is preferred, however, to administer the hyperosmotic composition within 2 years of implantation.

The volume of hyperosmotic composition administered to a given lesion is not critical. In specific embodiments, the volume of hyperosmotic composition administered is based on the volume (or estimated volume) of the undesired amount of calcium phosphate filler that is intended to be reduced and/or redistributed. In more specific embodiments, the volume of hyperosmotic composition administered to a given lesion ranges from 0.20 to 5 times the volume or estimated volume of the undesired amount of calcium phosphate filler to be treated. In specific embodiments, the ratio of volume (or estimated volume) of filler to volume of hyperosmotic composition ranges from 5:1 to 1:5. More preferably, the ratio of filler volume to volume of hyperosmotic composition ranges from 1:2 to 1:5. In other embodiments, the ratio of filler volume to volume of hyperosmotic composition is 1:1, 1:2, 1:3, 1:4 or 1:5. In a specific embodiment, the hyperosmotic composition is an aqueous solution and all volume limitations recited above apply to such hyperosmolar solutions.

In embodiment, hyperosmotic solution, particularly hyperosmotic aqueous solutions are administered by injection. One of ordinary skill in the art can select an appropriate injection protocol dependent upon particular site of implantation. The gauge of needle used for injection is not believed to be critical. Needles ranging from gauge 26-32 are however useful in injection methods herein.

The invention also relates to use of a hyperosmotic composition as described herein in the manufacture of a medicament for treatment of undesired calcium phosphate tissue filler implanted in a subject. The invention more specifically relates to use of a hyperosmotic composition as described herein in the manufacture of a medicament for reducing, diluting or redistributing an amount of calcium phosphate tissue filler implanted in a subject. All ranges of composition components and all ranges of osmolality listed herein can be employed in such use. The invention more specifically relates to the use of a hyperosmotic aqueous solution in the manufacture of a medicament for treatment of or more specifically for reducing, diluting and/or redistributing an amount of calcium phosphate tissue filler implanted in a subject. All ranges of composition components and all ranges of osmolality listed herein can be employed in such use. Manufactured medicaments can be formulated as is known in the art of administration by injection. More specifically manufactured medicaments can be formulated as is known in the art for administration by intralesion injection. Such medicament formulations can be in the form of solutions, gels or other suitable carriers. Preferred formulations are aqueous solutions.

The invention also provides a hyperosmotic pharmaceutical composition comprising one or more salts, sugar alcohols or sugars or a combination thereof for use in the treatment of undesired calcium phosphate tissue filler implanted in a subject. The invention more specifically relates to use of a hyperosmotic composition as described herein for reducing, diluting and/or redistributing an amount of calcium phosphate tissue filler implanted in a subject. All ranges of composition components and all ranges of osmolality listed herein can be employed in such compositions and such uses. In a specific embodiment, the pharmaceutical composition is an aqueous solution. All ranges of composition components and all ranges of osmolality listed herein can be employed in such aqueous solutions and such uses.

The invention further provides a pharmaceutical combination, preferably in a kit, comprising:
(a) a calcium phosphate tissue filler; and
(b) a hyperosmotic pharmaceutical composition.

In specific embodiments, the tissue filler and the hyperosmotic composition are in unit dosage forms which are physically discrete units containing a predetermined amount of the active ingredient for producing the desired therapeutic effect. In specific embodiments, the calcium phosphate filler is calcium hydroxyapatite. In specific embodiments, the calcium phosphate filler is Radiesse® dermal filler. In specific embodiments, the hyperosmotic pharmaceutical composition is a hyperosmotic aqueous solution. In specific embodiments, the hyperosmotic composition or hyperosmotic solution is formulated as is known in the art for injection.

Other aspects of the invention will be apparent from review of the following more detailed description and the examples.

BRIEF DESCRIPTION OF THE DRAWINGS

FIG. 2A shows filler particles from untreated injections of Radiesse® tissue filler in lower magnification (top) and higher magnification (bottom). FIG. 2B shows filler particles from injections of Radiesse® tissue filler treated with 25% w/v STS in lower magnification (top) and higher magnification (bottom). FIG. 2C shows filler particles from injections of Radiesse® tissue filler treated with normal saline in lower magnification (top) and higher magnification (bottom).

FIG. 4A is slice of untreated filler injection. FIG. 4B is slice of filler injection treated with STS. FIG. 4C is slice of filler injection treated with saline. In the figures, Rad is Radiesse® filler, N is necrosis, SC is subcutaneous compartments and D is dermis.

FIG. 8A data are from CT scans of the untreated filler nodule. FIG. 8B data are from CT scans of an injection nodule treated with STS.

FIG. 16 3D models of nodules from Example 4 in pig PC02 from T=1 h 15 to Day 15. Radiesse® dermal filler nodules in pink. (1 & 6)—Radiesse® dermal filler (alone). (2 & 7)—Magnesium Chloride Hexahydrate. (3 & 8)—Fructose. (4 & 9)—Sodium Hydrogen Carbonate. (5 & 10)—Trisodium Citrate Dihydrate.

DETAILED DESCRIPTION OF THE INVENTION

Figure 1:
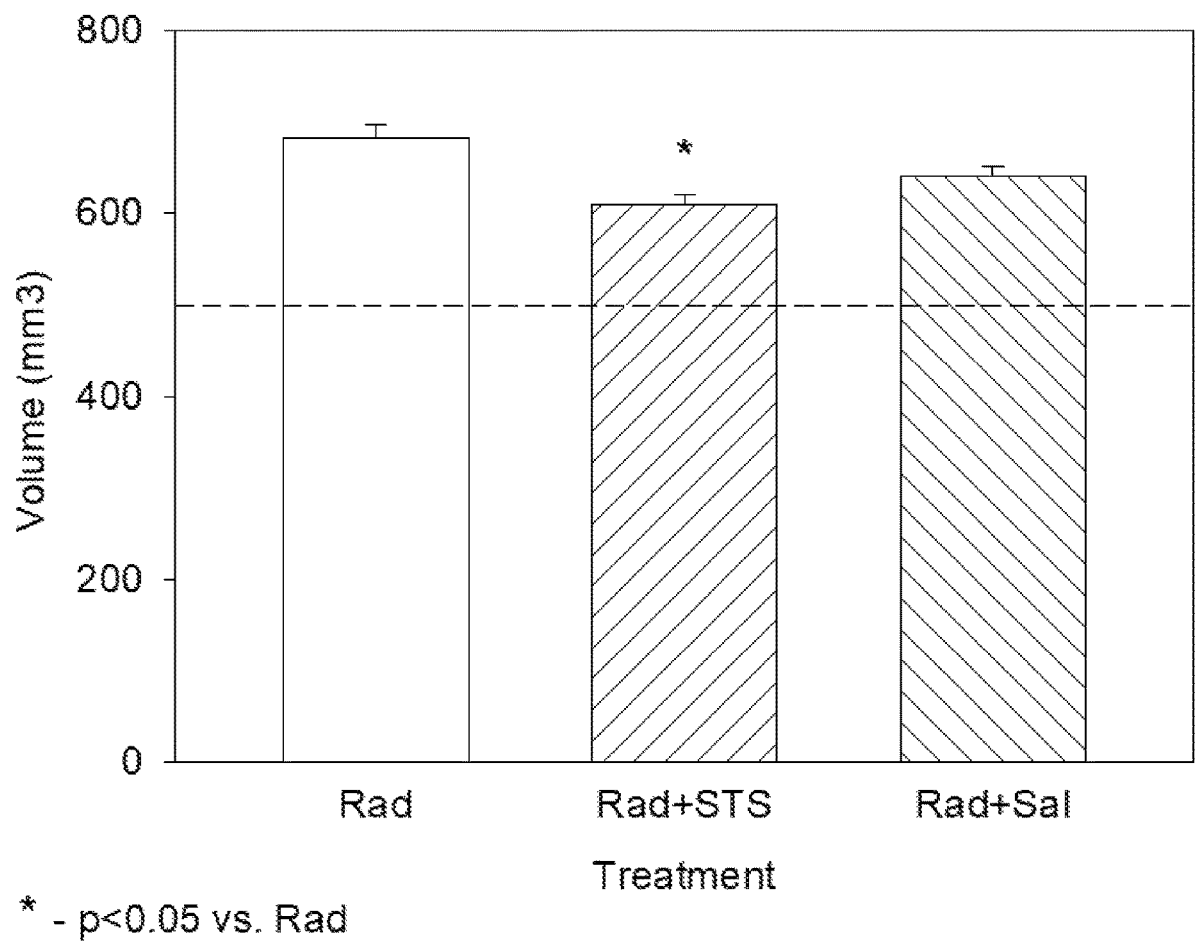
FIG. 1 is a graph showing the effect of STS and Saline treatment on dermal filler volume as measured by micro-CT on day 7 after injection.

The invention relates to methods, compositions, pharmaceutical compositions, or pharmaceutical compositions in the form of kits useful for treatment of undesired calcium phosphate tissue filler implanted in a subject. The invention more specifically relates to methods, compositions, pharmaceutical compositions, or pharmaceutical compositions in the form of kits useful for hyperosmotic composition as described herein in the manufacture of a medicament for reducing, diluting and/or redistributing undesired amounts and/or accumulations of calcium phosphate filler. The invention further relates to the use of hyperosmotic compositions for making medicaments for and hyperosmotic pharmaceutical compositions for use in the treatment, reduction and/or redistribution of such undesired amounts or accumulations of calcium phosphate filler. Undesired amounts of such filler, include undesired levels of such filler and undesired locations of such filler. Herein, such undesired amounts and locations of such filler are designated lesions. The methods, compositions, pharmaceutical compositions in the form of kits relates to the use of hyperosmotic composition for treating such lesions and more specifically for reducing, diluting and/or redistributing such undesired amounts and accumulations of such filler.

The methods and hyperosmotic compositions and solutions herein are used to dilute, reduce and/or redistribute undesired amounts or accumulations of calcium phosphate fillers. Such fillers are also called dermal fillers. Calcium phosphate fillers include those comprising calcium hydroxyapatite. In specific embodiments, the calcium phosphate filler is comprised of calcium hydroxyapatite microspheres in an aqueous gel carrier, such as Radiesse® filler as described, for example, in Berlin AL, Hussain M, Goldberg DJ. Calcium hydroxylapatite filler for facial rejuvenation: a histologic and immunohistochemical analysis. Dermatol Surg. 2008; 34 (suppl 1): S64-S67, which is incorporated by reference herein for the description of such filler and its use. PCT published application WO 2108/085748 is also incorporated by reference herein in its entirety for descriptions of calcium phosphate and related filler compositions. Reduction and/or redistribution of all such filler compositions can be achieved using methods and hyperosmotic compositions of this invention. U.S. provisional application 62/858,316, filed Jun. 6, 2019 is also incorporated by reference herein in its entirety.

In certain embodiments, the tissue filler composition comprises calcium phosphate, including, but not limited to, calcium hydroxyapatite (CaHA, also known as basic calcium phosphate), amorphous calcium phosphates (ACP), tetracalcium phosphate (TTCP), calcium pyrophosphate, monocalcium phosphates (MCPM), dicalcium phosphates (DCPA), tricalcium phosphate (TCP), octacalcium phosphate, calcium fluorapatite, calcium carbonate apatite, or combinations thereof. In certain embodiments, the tissue filler composition comprises hydroxyapatite derivatives. In certain embodiments, the tissue filler composition comprises calcium silicate, calcium carbonate, fluorapatite, fluorides or combinations thereof.

In certain embodiments, the tissue filler composition comprises calcium hydroxyapatite and a second tissue filler. In certain embodiments, the tissue filler composition comprises calcium hydroxyapatite and hyaluronic acid. In certain embodiments, weight ratio (or volume ratio, or molar ratio) of calcium hydroxyapatite and hyaluronic acid ranges from about 0.5:1 to about 0.6:1, from about 0.6:1 to about 0.8:1, from about 0.8:1 to about 1:1, from about 1:1 to about 1:1.5, from about 1:1.5 to about 1:2, from about 1:2 to about 1:2.5, or from about 1:2.5 to about 1:3.

In certain embodiments, the tissue filler composition comprises calcium hydroxyapatite and one or more other tissue filler. In certain embodiments, the tissue filler composition comprises calcium hydroxyapatite and one or more pharmaceutically acceptable carriers as described herein.

Hydroxyapatite, also known as hydroxylapatite, comprises calcium, phosphate and hydroxyl groups and has the chemical formula $Ca_5(PO_4)_3(OH)$. Hydroxyapatite is commonly written as $Ca_{10}(PO_4)_6(OH)_2$ to denote that the crystal unit comprises two hydroxyapatite molecules.

In one embodiment, the tissue filler is the injectable dermal filler Radiesse® (Merz North America, Inc.). Radiesse® filler is an opaque dermal filler composed of synthetic calcium hydroxylapatite (CaHA) microspheres (particles) suspended in a water-based gel carrier. In one embodiment, Radiesse® filler comprises synthetic calcium hydroxylapatite, water, glycerin and sodium carboxymethylcellulose. In certain embodiments, the sizes of the CaHA particles range from about 5 microns to about 100 microns, from about 10 microns to about 80 microns, from about 20 microns to about 60 microns, from about 10 microns to about 50 microns, from about 25 microns to about 45 microns, or from about 25 microns to about 40 microns. In certain embodiments, the sizes of the CaHA particles range from about 25 microns to about 45 microns.

In one embodiment, the tissue filler is Radiesse® (+) (Merz North America, Inc.) tissue filler. Radiesse® (+) tissue filler contains a small quantity (e.g., 0.3%) of local anesthetic (e.g., lidocaine), shown to reduce pain related to the injection.

As is known in the art, the calcium phosphate tissue filler can be implanted into a subject during plastic and/or reconstructive surgery. In a specific embodiment, calcium phosphate tissue filler is for hand augmentation. In a specific embodiment, calcium phosphate tissue filler is for hard or soft tissue augmentation, regeneration, and/or repair. In a specific embodiment, calcium phosphate tissue filler is for skin contour deficiencies. In a specific embodiment, calcium phosphate tissue filler is for treatment or amelioration of skin contour deficiencies comprising frown lines, worry lines, wrinkles, crow's feet, marionette lines, stretch marks, scars, or combinations thereof. While calcium phosphate tissue filler can be implanted into any subject, typically such filler is employed with human subjects. The reduction and/or redistribution methods of this invention can be employed after implantation of such filler as used for any of the recited applications noted above.

Hyperosmotic compositions and solutions herein are administered to treat undesired lesions comprising calcium phosphate filler.

Treatment herein refers to any improvement in undesired amounts or accumulations of implanted tissue filler, particularly calcium phosphate tissue filler and more particularly calcium hydroxyapatite tissue filler. Undesired amounts or accumulations of implanted tissue filler include any undesired or unintended results of tissue filler implantation and specifically include, among others, amounts or accumulations that are implanted in an undesired or unintended location; amounts or accumulations in a given location that are higher than desired or intended; amounts that migrate to one or more undesired locations; or amounts or accumulations that result in an undesirable visual result, such as undesired nodules or undesired uneven contours. Undesired amounts or accumulations can also include amounts or accumulations that result in undesired compression of surrounding tissue; amounts or accumulations that result in pain; amounts or accumulations that result in inflammation; or amounts or accumulations that result in infection. Undesired amounts or accumulations of tissue filler can further include those amounts or accumulations that a subject wishes to have reduced or reshaped.

Improvement achieved with the methods and composition herein typically involves a reduction in amount of tissue filler, particularly in a given location. The term lesion herein is used to describe a specific location of an amount or accumulation of implanted tissue filler. Certain lesions may be undesirable, for example, in location, lesion size or shape; or amount of filler in a lesion. Treatment herein includes improvement in location, size, shape, or amount of filler in an undesired lesion containing implanted tissue filler.

In specific embodiments, treatment involves injection of a hyperosmotic solution to a location containing an undesired amount or accumulation of implanted tissue filler. Such administration results in a measureable change in the size, location, or amount of tissue filler and preferably results in an improvement of the undesired amount or accumulation of tissue filler. Without wishing to be bound by any particular mechanism of action, this measurable change may in some embodiments, at least in part result from (1) direct degradation of the particles of tissue filler; (2) dilution of tissue filler in a given location; (3) indirect degradation, i.e., triggering of biological processes for filler degradation and/or improving access of such biological processes to particles or (4) redistribution of the particles of tissue filler. In certain embodiments, degradation of particles of tissue filler may be triggered at least in part by activation of inflammatory process, rather than by direct degradation of particles by action of the hyperosmotic solution. In a specific embodiment, the improvement in undesired implanted tissue filler is not due to direct degradation of the particles or molecules of tissue filler. In a specific embodiment, the improvement in undesired implanted tissue filler is due at least in part to dilution of implanted tissue filler at a selected location, for example, due to dilution of implanted tissue filler in a selected lesion. The term in situ dilution refers to a reduction of the amount of tissue filler in a lesion. In situ dilution can result in a change in size, shape or amount of filler in a lesion, which in turn provides a desired improvement of the undesired amount or accumulation of implanted tissue filler. More specifically, in situ dilution can result in a visual improvement, for example, reduction or reshaping of nodules or smoothing of contours. In situ dilution can further result in relief of compression of surrounding tissue or relief or pain. In situ dilution can facilitate treatment of inflammation or treatment of infection.

Again, while not wishing to be bound by any particular mechanism of action, it is currently believed that injection of certain hyperosmotic solutions can change the water dynamics in the vicinity of implanted dermal filler, for example, to pull water out of tissue in the vicinity of implanted tissue to dilute the filler. It is currently believed that this form of dilution is preferably achieved by use of hyperosmotic solution. This form of dilution of filler can result in acceleration of biological processes, such as inflammation, as particles of filler become more dispersed allowing better access of inflammatory cell to filler resulting in filler degradation (indirect degradation of filler).

Administration of hyperosmotic solution is optionally accompanied by massage of the area containing the undesired amount, shape or location of undesired tissue filler. In specific embodiments, treatment methods herein do not require application of massage.

Treatment of undesired amounts or accumulations herein can be combined with other known treatments or procedures to achieve desired improvements or benefits. For example, treatments herein can be combined with known methods for treatment of pain, inflammation or infection.

In specific embodiments, administration is by application to lesion tissue. For example, the hyperosmotic composition or solution is applied to an undesired nodule or other accumulation of the filler. In a specific embodiment, the hyperosmotic composition is injected into the lesion (intralesional injection). Dependent upon the location of the undesired amount or accumulation of filler, the hyperosmotic composition or solution can be administered by one or more of deep dermal, subdermal, subcutaneous, intramuscular, or supraperiosteal injection. Again dependent upon the nature and location of the undesired amount or accumulation of filler, the hyperosmotic composition or solution can be administered during a surgical procedure directly to the tissue of or surrounding the lesion.

The term hyperosmotic relates to compositions, particularly aqueous solutions, which have osmolality or osmolarity significantly higher than human tissue, as exemplified by the osmolarity of human plasma which ranges from about 275 to 299 milliosmol/liter (milliosmole/L). For comparison, normal saline is 0.9% (w/v) of sodium chloride in water which has calculated osmolality of 308 milleosmol/Kg (of solution) and calculated osmolarity of 308 milliosmol/L. At lower concentrations of solutes, calculated osmolality and osmolality are about the same, but the values diverge at higher concentrations of solutes. For purposes of clarity herein, hyperosmotic compositions are those that have a calculated osmolality of at least 3 times normal saline, i.e., at least 900 milliosmol/Kg. Those of ordinary skill in the art can readily calculate osmolality or osmolarity of a composition, particularly an aqueous solution, based on the known chemical formula of salt or non-salt compound and the concentration of that salt or non-salt in the composition or solution.

Osmolality is also known as osmotic concentration and refers to osmoles (osm per Kg of composition, particularly solution) and is a measure of solute concentration. As is known in the art, an osmole is one mole of any non-dissociable substance. Herein the units of osmolality used are milliosmole/Kg. All components of a composition can contribute to the osmolality of a composition. In particular, all solutes contribute to the osmolality of an aqueous solution. As is known in the art, osmolality is used for the concentration of the particles that are dissolved in a biological fluid, e.g., urine. Osmolality, as is also known in the art, is measured using an osmometer by freezing point depression or vapor pressure elevation techniques. It is further known in the art that measured osmolality may differ from calculated osmolality. As is known in the art, osmotic concentration can also be calculated in terms of osmolarity, osm per liter of solution.

In specific embodiments herein, hyperosmotic compositions herein have calculated osmolality ranging from 1000 to 5000 milliosmol/Kg. In embodiments, the calculated osmolality of the hyperosmotic composition ranges from 2500 to 5000 milliosmol/Kg. In embodiments, the calculated osmolality of the hyperosmotic composition ranges from 1000 to 4000 milliosmol/Kg. In embodiments, the calculated osmolality of the hyperosmotic composition ranges from 1000 to 3500 milliosmol/Kg. In embodiments, the calculated osmolality of the hyperosmotic composition ranges from 1000 to 3000 milliosmol/Kg. In embodiments, the calculated osmolality of the hyperosmotic composition ranges from 1000 to 2500 milliosmol/Kg. In embodiments, the calculated osmolality of the hyperosmotic composition ranges from 1000 to 2000 milliosmol/Kg. In embodiments, the calculated osmolarity of the hyperosmotic composition ranges from 1000 to 1500 milliosmol/Kg. In embodiments, the calculated osmolality of the hyperosmotic composition ranges from 2000 to 4000 milliosmol/Kg. In embodiments, the calculated osmolality of the hyperosmotic composition ranges from 2000 to 3000 milliosmol/Kg. In embodiments, the calculated osmolality of the hyperosmotic composition ranges from 2500 to 3500 milliosmol/Kg. In embodiments, the calculated osmolality of the hyperosmotic composition ranges from 2500 to 3000 milliosmol/Kg.

It will be appreciated by one of ordinary skill in the art that the maximum osmolality of a given tonicity modifying agent in a given solvent or solution is limited by the solubility of the tonicity agent in that solvent or solution. For example, the solubility of certain tonicity agents in water may be lower than that required to achieve the upper limits of osmolality recited herein.

Tonicity modifying agents are the components of the composition or solution that determine osmolality and osmolarity. A composition or solution herein can contain one or more such tonicity modifying agents. In specific embodiment, the tonicity modifying agents are species which on dissolution in water generate more than one solute particle, such as a salt. Tonicity modifying agents include those salts comprising more than one cation or more than one anion to satisfy charge balance, for example, sodium sulfate ($Na_2SO_4$) or magnesium chloride ($MgCl_2$).

Solutions having measured osmolality using an osmometer within the range of 1000 to 5000 milleosmol/Kg and any subranges thereof are useful in the present invention.

In more specific embodiments, the one or more tonicity modifying agents are selected from pharmaceutically acceptable salts, pharmaceutically acceptable sugar alcohols, pharmaceutically acceptable sugars and any combinations thereof. It is noted that a given tonicity modifying agent must be pharmaceutically acceptable at the concentration that it is used in the composition that is needed to achieve the selected osmolality alone or in combination with one or more other tonicity modifying agents.

In specific embodiments, the pharmaceutically acceptable salts are alkali metal salts. In specific embodiments, the pharmaceutically acceptable salts are sodium salts. In specific embodiments, the pharmaceutically acceptable salts are calcium salts. In specific embodiments, the pharmaceutically acceptable salts are magnesium salts. In specific embodiments, the salts are chloride salts. In specific embodiments, the salts are acetate salts. In specific embodiments, the salts are sulfate salts. In specific embodiments, the salts are dihydrogen phosphate salts. In specific embodiments, the salts are phosphate salts. In specific embodiments, the pharmaceutically acceptable salts are alkali metal salts wherein the anion is selected from a halide, a carboxylate, a sulfate, a phosphate, and a dihydrogen phosphate. In specific embodiments, the pharmaceutically acceptable salts are alkali metal salts wherein the anion is selected from chloride, acetate, sulfate, phosphate, and dihydrogen phosphate. In specific embodiments, the salt is sodium chloride. In specific embodiments, the salt is sodium acetate.

In specific embodiments, the salt is sodium dihydrogen phosphate. In specific embodiments, the salt is calcium chloride. In specific embodiments, the salt is magnesium sulfate.

In specific embodiments, the hyperosmotic composition or solution comprises two or more different salts, wherein the total calculated osmolality of the composition is within one of the hyperosmolar ranges recited herein.

In specific embodiments, the hyperosmotic composition is an aqueous solution and the one or more tonicity modifying salts are water-soluble salts. It is noted that the tonicity modifying salt is soluble in the aqueous solution at the concentration needed to achieve a desired osmolality alone or in combination with one or more other selected tonicity modifying agents.

In specific embodiments, sugar alcohols include, among others, glycerol, sorbitol, mannitol, xylitol, isomalt, erythritol or maltitol. In specific embodiments, sugar alcohols include glycerol and mannitol. Sugar alcohols used herein are pharmaceutically acceptable at the concentration used in the composition or solution to achieve the desired osmolality alone or in combination with other tonicity modifying agents. For aqueous solutions, water soluble sugar alcohols are employed.

Hyperosmotic solutions herein may include minor amount of components other than tonicity modifying agents, which may to a minor extent also contribute to osmolality, but which are employed in the solution as antimicrobial agents, preservatives, and the like as is known in the art or which may facilitate formulation of the solutions for administration as is also known in the art.

In embodiments of hyperosmotic solutions herein, the pH of a given hyperosmotic solution can be adjusted by addition of appropriate acid or base, such as HCl or NaOH (typically small amounts of concentrated acid or base) to hyperosmotic solutions. Addition of acid or base and pH adjustment may affect osmolality of the solution as is known in the art. In embodiments herein, the pH of hyperosmotic solutions ranges from pH 4 to pH 10. In embodiments herein, the pH of hyperosmotic solutions ranges from pH 5 to pH 9. In embodiments herein, the pH of hyperosmotic solutions ranges from pH 6 to pH 8.

In specific embodiments, hyperosmotic compositions useful in the methods and kits herein include the following:
- hyperosmotic pharmaceutical compositions or solutions containing a tonicity modifying agent which is a salt;
- hyperosmotic pharmaceutical compositions or solutions containing a tonicity modifying gent which is not a salt;
- hyperosmotic pharmaceutical compositions or solutions containing a tonicity modifying agent which is a sugar alcohol;
- hyperosmotic pharmaceutical compositions or solutions containing a tonicity modifying gent which is a mono- or disaccharide;
- hyperosmotic pharmaceutical compositions or solutions containing more than one tonicity modifying agent;
- hyperosmotic pharmaceutical compositions or solutions containing more than one tonicity modifying agent wherein one such tonicity modifying agent is a salt;
- hyperosmotic pharmaceutical compositions or solutions containing more than one tonicity modifying agent wherein one such tonicity modifying agent is a sugar alcohol;
- hyperosmotic pharmaceutical compositions or solutions containing more than one tonicity modifying agent wherein one such tonicity modifying agent is a sugar;
- hyperosmotic pharmaceutical compositions or solutions wherein the tonicity modifying agent is selected from a salt, a sugar alcohol, a sugar or a mixture thereof;
- hyperosmotic pharmaceutical compositions or solutions wherein the tonicity modifying agent is selected from a salt, a sugar alcohol, a sugar or a mixture thereof, and wherein the salt is a physiologically acceptable sodium, calcium or magnesium salt;
- hyperosmotic pharmaceutical compositions or solutions wherein the tonicity modifying agent is a pharmaceutically acceptable sodium, calcium or magnesium salt;
- hyperosmotic pharmaceutical compositions or solutions wherein the tonicity modifying agent is a pharmaceutically acceptable salt the formula of which contains more than one cation or anion;
- hyperosmotic pharmaceutical compositions or solutions wherein the tonicity modifying agent is other than sodium thiosulfate;
- hyperosmotic pharmaceutical compositions or solutions wherein the tonicity modifying agent is other than sodium metabisulfite;
- hyperosmotic pharmaceutical compositions or solutions which do not contain sodium thiosulfate or sodium metabisulfite;
- hyperosmotic pharmaceutical compositions or solutions comprising sodium thiosulfate wherein the osmolality contributed by the sodium thiosulfate is less than 3000 milliosmol/Kg;
- hyperosmotic pharmaceutical compositions or solutions comprising sodium thiosulfate wherein the osmolality contributed by the sodium thiosulfate is less than 2500 milliosmol/Kg;
- hyperosmotic pharmaceutical compositions or solutions comprising sodium thiosulfate wherein the osmolality contributed by the sodium thiosulfate is less than 1000 milliosmol/Kg;
- hyperosmotic pharmaceutical compositions or solutions comprising sodium metabisulfite wherein the osmolality contributed by the sodium metabisulfite is less than 3000 milliosmol/kg;
- hyperosmotic pharmaceutical compositions or solutions comprising sodium metabisulfite wherein the osmolality contributed by the sodium metabisulfite is less than 2500 milliosmol/Kg
- hyperosmotic pharmaceutical compositions or solutions comprising sodium metabisulfite wherein the osmolality contributed by the sodium metabisulfite is 1000 milliosmol/Kg or less;
- hyperosmotic pharmaceutical compositions or solutions which are aqueous solutions of sodium thiosulfate that have osmolality in the range of 1000 to 2500 milliosmol/Kg;
- hyperosmotic pharmaceutical composition which are aqueous solutions of sodium metabisulfite that have osmolality in the range of 1000 to 2500 milliosmol/Kg;
- hyperosmotic pharmaceutical compositions or solutions wherein the tonicity modifying agent of the hyperosmotic pharmaceutical composition is selected from the group consisting of sodium chloride, sodium dihydrogen phosphate, sodium bicarbonate, sodium acetate, sodium citrate, magnesium chloride, magnesium sulfate, glycerol, mannitol, glucose, fructose, sucrose and a combination thereof;
- hyperosmotic pharmaceutical compositions or solutions wherein the tonicity modifying agent of the hyperosmotic pharmaceutical composition is selected from the group consisting of sodium chloride, sodium acetate or glycerol;
- hyperosmotic pharmaceutical compositions or solutions wherein the tonicity modifying agent of the hyperosmotic pharmaceutical composition is sodium dihydrogen phosphate;

hyperosmotic pharmaceutical compositions or solutions wherein the tonicity modifying agent is sucrose;

hyperosmotic pharmaceutical compositions which are aqueous solutions;

hyperosmotic pharmaceutical compositions which are aqueous solutions including any one or a combination of the above specifically mentioned tonicity modifying agents; or hyperosmotic pharmaceutical compositions which are aqueous gels including any including any one or a combination of the above specifically mentioned tonicity modifying agents.

In a specific embodiment, the hyperosmotic pharmaceutical composition is hypertonic saline having 3%-9% (w/v) sodium chloride. In a specific embodiment, the hyperosmotic pharmaceutical composition is hypertonic saline having 5%-9% (w/v) sodium chloride. In a specific embodiment, the hyperosmotic pharmaceutical composition is hypertonic saline having 9% (w/v) sodium chloride. In a specific embodiment, the hyperosmotic pharmaceutical composition is hypertonic saline having 3% (w/v) sodium chloride. In a specific embodiment, the hyperosmotic pharmaceutical composition is hypertonic saline having 5% (w/v) sodium chloride. In a specific embodiment, the hyperosmotic pharmaceutical composition is hypertonic saline having 7% (w/v) sodium chloride.

In a specific embodiment, the hyperosmotic composition useful herein is a hyperosmotic aqueous solution of sodium acetate. More specifically, the useful hyperosmotic aqueous solutions of sodium acetate have a concentration of sodium acetate ranging from 0.5 M to 2.5 M. Yet more specifically, the useful hyperosmotic aqueous solutions of sodium acetate have a concentration of sodium acetate ranging from 0.5 M to 2.0 M or 0.5 to 1.75 M, or 0.5 to 1.5 M, or 1.0 to 1.5 M or 1.0 M or 1.5 M.

In a specific embodiment, the hyperosmotic composition useful herein is a hyperosmotic aqueous solution of sodium dihydrogen phosphate. More specifically, the useful hyperosmotic aqueous solutions of sodium dihydrogen phosphate have a concentration of sodium dihydrogen phosphate ranging from 0.5 M to 2.5 M. Yet more specifically, the useful hyperosmotic aqueous solutions of sodium dihydrogen phosphate have a concentration of sodium dihydrogen phosphate ranging from 0.5 M to 2.0 M or 0.5 to 1.75 M, or 0.5 to 1.5 M, or 1.0 to 1.5 M or 1.0 M or 1.5 M.

In a specific embodiment, the hyperosmotic composition useful herein is a hyperosmotic aqueous solution of glycerol. More specifically, the useful hyperosmotic aqueous solutions of glycerol have a concentration of glycerol ranging from 1 M to 5 M. Yet more specifically, the useful hyperosmotic aqueous solutions of glycerol have a concentration of glycerol ranging from 1 M to 3.5 M or 1 to 3 M, or 1 to 2 M, or 1 to 1.5 M or 1 M, or 2 M or 3 M.

In a specific embodiment, the hyperosmotic composition useful herein is a hyperosmotic aqueous solution of sucrose. More specifically, the useful hyperosmotic aqueous solutions of sucrose have a concentration of sucrose ranging from 1 M to 1.5 M. Yet more specifically, the useful hyperosmotic aqueous solutions of sucrose have a concentration of sucrose ranging from 1 to 1.25 M or 1 M, or 1.25 M or 1.5 M.

In a specific embodiment, the hyperosmotic composition useful herein is a hyperosmotic aqueous solution of fructose. More specifically, the useful hyperosmotic aqueous solutions of fructose have a concentration of fructose ranging from 1 M to 5 M. Yet more specifically, the useful hyperosmotic aqueous solutions of fructose have a concentration of fructose ranging from 1 to 3.5 M, or 1-3 M, or 1-2.5 M, or 1-2 M, or 1-1.5 M or 1 M, or 1.5 M, or 2 M, or 3 M, or 4 M or 5 M.

In a specific embodiment, the hyperosmotic composition useful herein is a hyperosmotic aqueous solution of sodium citrate. More specifically, the useful hyperosmotic aqueous solutions of sodium citrate have a concentration of sodium citrate ranging from 0.25 M to 1.25 M. Yet more specifically, the useful hyperosmotic aqueous solutions of sodium citrate have a concentration of sodium citrate ranging from 0.25 M to 1 M or 0.25 to 0.75 M, or 0.5 to 1.0 M, or 0.5 to 1.25 M or 0.25 M, or 0.5 M, or 0.75 M or 1 M.

In a specific embodiment, the hyperosmotic composition useful herein is a hyperosmotic aqueous solution of sodium bicarbonate. More specifically, the useful hyperosmotic aqueous solutions of sodium bicarbonate have a concentration of sodium bicarbonate ranging from 0.5 M to 1 M. Yet more specifically, the useful hyperosmotic aqueous solutions of sodium bicarbonate have a concentration of sodium bicarbonate ranging from 0.5 M to 0.75 M or 0.5 M, or 0.75 M or 1 M.

In a specific embodiment, the hyperosmotic composition useful herein is a hyperosmotic aqueous solution of magnesium chloride. More specifically, the useful hyperosmotic aqueous solutions of magnesium chloride have a concentration of magnesium chloride ranging from 0.33 to 1.65 M. Yet more specifically, the useful hyperosmotic aqueous solutions of magnesium chloride have a concentration of magnesium chloride ranging from 0.33 to 1.5 M, or 0.33 to 1 M, or 0.5 to 1.5 M, or 0.5 to 1 M, or 0.75 to 1.25 M or 0.33 M, or 0.66 M, or 0.5 M, or 1.0 M, or 1.25 M or 1.5 M.

The timing of administration of the hyperosmotic composition or solution with respect to implantation of the filler is not in general critical. Administration can be shortly after implantation, if and when, undesired amount, accumulation or location of filler is detected. This can be within minutes, hours or days of implantation. However, formation or detection of such undesired amounts, accumulations or locations may occur weeks, months or years after implantation and the hyperosmotic composition or solution can be administered after such delayed formation or detection. In a specific embodiment, administration of hyperosmotic compositions or solutions is preferably within 2 years of filler implantation.

The volume of hyperosmotic composition or solution administered is not critical. It is preferred to contact the entire volume of the lesion with the hyperosmotic composition or solution. In specific embodiments, the volume of hyperosmotic composition or solution administered is related to the volume, including an estimated volume, of the undesired amount or accumulation of filler. In specific embodiments, the volume of hyperosmotic composition or solution ranges from 0.20 to 5 times the volume of the volume of filler. More specifically the volume of hyperosmotic composition or solution ranges from 0.25 to 5 times the volume of filler. In more specific embodiments, volume ratio of the tissue filler to the pharmaceutical composition ranges from 5:1 to about 1:5. In more specific embodiments, volume ratio of the tissue filler to the pharmaceutical composition ranges from 4:1 to about 1:5. In more specific embodiments, volume ratio of the tissue filler to the pharmaceutical composition ranges from 1:1 to 1:5 or from 1:2 to 1:5.

The term pharmaceutically acceptable refers to components of composition and solutions herein and the resulting compositions and solutions which are hyperosmotic as define herein. Pharmaceutical acceptability herein refers to the use of the components, compositions and solutions in the particular methods described. Pharmaceutically acceptable includes those components, compositions and solutions that are not toxic to a subject as employed. More specifically, pharmaceutically acceptable includes those components, compositions and solutions that do not cause unacceptable trauma to tissue on application. More specifically, pharmaceutically acceptable includes those components, compositions and solutions that do not induce unacceptable levels of tissue necrosis on application. More specifically, pharmaceutically acceptable includes those components, compositions and solutions that do not induce unacceptable levels of inflammation to tissue on application. Hyperosmotic composition and solutions herein may cause some level of transitory inflammation on administration without being unacceptable for uses herein.

A variety of pharmaceutically acceptable salts are known in the art and can be employed herein.

Hyperosmotic compositions and solutions herein can include ingredients other than tonicity modifying agents as is known in the art for use in formulation of injectable compositions or gels. Such ingredients include, for example, antimicrobial agents, preservatives, and the like. Such additional ingredients are typically included in formulations in minor amounts, but which may also contribute to osmolality. In specific embodiments, such other ingredients are typically present in formulation at levels of 5% wt/vol or less, and more preferably at levels of 1% wt/vol or less.

In a specific embodiment, hyperosmotic compositions and solutions herein contain a small quantity (e.g., 0.3%) of local anesthetic (e.g., lidocaine), to reduce pain related to injection. It is noted that osmolality may be affected by inclusion of components not specifically designated herein as tonicity modifying agents. Total osmolality of the compositions or solutions with such ingredients can be calculated based on known concentrations of known ingredients or can be measured using methods that are well known in the art.

Methods herein employing hyperosmotic compositions and solutions herein as administered herein cause a detectable reduction in amount of filler or a detectable redistribution of filler. In specific embodiments herein, a detectable reduction or redistribution of filler can be observed 1 week to 1 month after treatment. It is noted that treatment can involve multiple injections at the same time or separated in time by 1 week or more. Treatment can involve multiple injections at different locations, for example at different locations in the same lesion, at the same time or at different times. In a specific embodiment, detectible reduction or redistribution is observed after the last treatment injection. In specific embodiments, the amount of the implanted calcium phosphate tissue filler is reduced at least 10% about 1 week after administration of the pharmaceutical composition. In specific embodiments, the amount of the implanted calcium phosphate tissue filler is reduced at least 30% about 1 week after administration of the pharmaceutical composition. In specific embodiments, the amount of the implanted calcium phosphate tissue filler is reduced at least 50% about 1 week after administration of the pharmaceutical composition. In specific embodiments, the amount of the implanted calcium phosphate tissue filler is reduced at least 80% about 1 week after administration of the pharmaceutical composition. In specific embodiments, the amount of the implanted calcium phosphate tissue filler is reduced at least 90% about 1 week after administration of the pharmaceutical composition. In specific embodiments, the amount of the implanted calcium phosphate tissue filler is reduced at least 90% within one month after administration of the pharmaceutical composition. In specific embodiments, the at least 50%, at least 80% or at least 90% detectible reduction or redistribution is observed, respectively, after 24 hours.

Published PCT application WO 2018/085748 is incorporated by reference herein in its entirety for methods of detection of reduction of the amount or accumulation of calcium phosphate filler (see in particular section 6.5, pages 22-23). More specifically, such reduction or redistribution is measured using any method known in the art for measuring calcification.

In some embodiments, methods of measuring/assessing calcification, or methods of measuring/assessing the amount of a calcium phosphate tissue filler, include, but are not limited to, in vivo imaging methods such as plain film roentgenography, coronary arteriography; fluoroscopy, including digital subtraction fluoroscopy; cinefluorography; computed tomography (CT); X-ray; helical computed tomography; spiral computed tomography; electron beam computed tomography (EBCT); intravascular ultrasound (IVUS); magnetic resonance imaging; and transthoracic and transesophageal echocardiography. Coronary interventionalists may use cinefluorography and IVUS to evaluate calcification in specific lesions before angioplasty. In some embodiments, CT can be done using double-helix CT scanners or single-helix scanners.

In some embodiments, calcification, or the amount of a calcium phosphate tissue filler, can be measured by magnetic resonance imaging (MRI). In some embodiments, calcification, or the amount of a calcium phosphate tissue filler, can be measured by transthoracic (surface) echocardiography. In some embodiments, calcification, or the amount of a calcium phosphate tissue filler, can be assessed ex vivo by Van Kossa method. This method relies upon the principle that silver ions can be displaced from solution by carbonate or phosphate ions due to their respective positions in the electrochemical series. The argentaffin reaction is photochemical in nature and the activation energy is supplied from strong visible or ultra-violet light. Since the demonstrable forms of tissue carbonate or phosphate ions are invariably associated with calcium ions, the method can be considered as demonstrating sites of tissue calcium deposition.

Other methods of measuring calcification, or the amount of a calcium phosphate tissue filler, include, but are not limited to, immuno-fluorescent staining and densitometry. In another aspect, methods of assessing calcification, or the amount of a calcium phosphate tissue filler, include methods of measuring determinants and/or risk factors of vascular calcification. Such factors include, but are not limited to, serum levels of phosphorus, calcium, and calcium phosphorus product, parathyroid hormone (PTH), low-density lipoprotein cholesterol (LDL), high-density lipoprotein cholesterol (HDL), triglycerides, and creatinine. Methods of measuring these factors are well known in the art. Other methods of assessing calcification, or the amount of a calcium phosphate tissue filler, include assessing factors of bone formation. Such factors include bone formation markers such as bone-specific alkaline phosphatase (BSAP), osteocalcin (OC), carboxyterminal propeptide of type I collagen (PICP), and aminoterminal propeptide of type I collagen (PINP); serum bone resorption markers such as cross-linked C-telopeptide of type I collagen (ICTP), tartrate-resistant acid phosphatase, TRACP and TRAP5B, N-telopeptide of collagen cross-links (NTx), and C-telopeptide of collagen cross-links (CTx); and urine bone resorption markers, such as hydroxyproline, free and total pyridinolines (Pyd), free and total deoxypyridinolines (Dpd), N-telopeptide of collagen cross-links (NTx), and C-telopeptide of collagen crosslinks (CTx).

In embodiments, the calcium hydroxylapatite (CaHA) particles of Radiesse® injectable implant are radiopaque and are visible on CT Scans and/or in standard, plain radiography.

In specific embodiments, the efficacy of any given hyperosmotic composition or solution herein can be assessed in experiments using animal or human skin samples or in animal experiments using pigs, for example. In such testing, for example, different high osmolarity solutions (1-2 mL) are injected into a calcium phosphate filler (0.5-1 mL) bump implanted subdermal in the pig, 1 hr earlier. In exemplary testing, CT is used to monitor short term changes in the injection site (up to 24 hr on treatment. Other exemplary CT testing monitors changes in the injection site over any appropriate time after treatment, for example, over days or over multiple weeks. More specifically, exemplary CT testing monitors changes in the injection site after treatment over 7 days or 14 days. Histology (filler presence, inflammatory reaction, etc. is used to monitor filler dispersion after injection. Histology assessment is made over any appropriate time after treatment. Exemplary histology assessment is made 7-14 days after treatment. Additional histology assessment can be made 7-14 days or later after treatment. In embodiments, CT analysis can provide information on filler volume as a function of time after treatment.

When a Markush group or other grouping is used herein, all individual members of the group and all combinations and subcombinations possible of the group are intended to be individually included in the invention. Every formulation or combination of components described or exemplified can be used to practice the invention, unless otherwise stated. Specific names of compounds are intended to be exemplary, as it is known that one of ordinary skill in the art can name the same compounds differently.

One of ordinary skill in the art will appreciate that methods, including experimental procedures and analytical methods, and materials other than those specifically exemplified can be employed in the practice of the invention without resort to undue experimentation. All art-known functional equivalents of any such methods or materials are intended to be included in this invention. Whenever a range is given in the specification, for example, a composition range, all intermediate ranges and subranges, as well as all individual values included in the ranges given are intended to be included in the invention.

The invention illustratively described herein suitably may be practiced in the absence of any element or elements, limitation or limitations which is not specifically disclosed herein.

Without wishing to be bound by any particular theory, there can be discussion herein of beliefs or understandings of underlying principles or mechanisms of action relating to the invention. It is recognized that regardless of the ultimate correctness of any mechanistic explanation or hypothesis, an embodiment of the invention can nonetheless be operative and useful.

All references throughout this application, for example patent documents including issued or granted patents or equivalents; patent application publications; and non-patent literature documents or other source material; are hereby incorporated by reference herein in their entireties, as though individually incorporated by reference.

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention.

THE EXAMPLES

Example 1

The dermal filler (Radiesse® calcium hydroxylapatite labelled as Radiesse® Volume Advantage 1.5 cc, syringes) was injected in the superficial part of the subcutaneous compartment in the abdominal skin of three pigs (female Swine (*Sus scrofa domesticus*) Landrace-Large White cross from SCEA Poraubennes, France, having body weight between 56 to 58 kg at injection.) Ten sites per animal were injected, with approximately 0.5 mL of the dermal filler using graduated syringes.

One hour±5 minutes after the dermal filler injection, test sites (10 each) were injected with aqueous 25% (w/v) sodium thiosulfate or control (0.9% saline solution, normal saline). No treatment was injected in the remaining 10 sites (dermal filler alone). Three to four sites were employed for each treatment in each animal. Normal saline control and the STS solution were injected in each dedicated site at a volume of 1.5 mL Seven days following injection, animals were euthanized. The local tissue effects and degradation of the dermal filler were evaluated macroscopically, 3-D camera, histopathologically, histomorphometrically, and by micro-CT.

Micro-CT Analysis

After complete fixation in 10% NBF, the 30 test sites and one additional site (TO) were scanned by cone beam microcomputed tomography (µCT 40, SCANCO, Switzerland) following the procedure:

Energy/Intensity: 70 Kvp, 114 µA, 8 W
Integration time: 300 ms
Frame averaging: 2
Nominal resolution High: 18 µm The measured data were filtered using a Gaussian filter with finite filter support and filter width. The images were then segmented to separate the implant from the tissue background and the global volume of material was measured.

The signal detected in a CT scan is directly correlated with the density of the material in the sample scanned. The signal obtained is normalized to a grey scale (Hounsfield Unit Scale) which ranges from −1000 HU (air, the less dense medium) to +several thousand HU (very dense material, e.g., bone). Exemplary HU values of materials include: water (0 HU), soft tissue (+50 HU), Radiesse® dermal filler (approx.: +800 HU). A decrease in mean HU associated with granules in a given volume can result from removal or loss of granules from the volume or a change in volume. A decrease in mean HU can indicate removal or loss of granules or dilution of granules in a given volume. Decrease of HU combined with an increase in volume can indicate water intake giving a dilution effect and/or infiltration of cellular elements or extracellular matrix.

Electron Microscopy

EM analysis is used, for example, to analyze morphology and the particle size distribution of Calcium Hydroxyapatite (CaHA) particles in tissue integrated particles. Following Micro-CT analysis, sites dedicated to electron microscopy underwent a lateral biopsy (approximately 5×5×5 mm) and were harvested. The biopsy material underwent an enzymatic digestion with protease (Trypsin without EDTA, for 30 days, at 37° C.) after fixation in 10% neutral buffered formalin (NBF). Digested sample was centrifuged, and microscopy samples of the supernatant as well as the pellet were prepared and subjected to EM analysis at room temperature.

Samples were analyzed using a Scanning Electron Microscope (SEM) (Phenom Pure G3, ThermoFisher, with Phenom Pro Suite application system, ImageJ (version 1.51j8) software and OriginPro 2018G (64-bit) SR1 b9.5.1.195 software for analysis and data processing). To evaluate the changes in CaHA microparticle characteristics the samples were analyzed with the Scanning Electron Microscopy (SEM) and evaluated for morphology as well as for the size and shape of the material. Statistical analysis of particle size distribution (PSD) would show changes of the material.

SEM images were taken from three fractions per sample to determine the particle- and volume-weighted size distributions. Up to 400 SEM images per fraction were taken at a magnification of ×500 and further processed by automated image analyzing software ImageJ (version 1.51j8). Image processing took place for every fraction image to determine selected parameters. e.g., Feret diameter and aspect ratio (D-ratio). The averaged results represent particle- and volume-weighted size distributions based on at least more than 20K identified particles.

Histopathology

After complete fixation in 10% NBF and micro-CT analysis, the 30 test sites and the T0 site, were cut into five blocks. The blocks were decalcified for 48 hours with formic acid and then dehydrated in alcohol solutions of increasing concentration, cleared in xylene and embedded in paraffin. Following embedding, poor quality of the slides was noted so the blocks were then decalcified in EDTA for 30 min. Following this second decalcification, the poor quality of the slides still did not permit histopathologic evaluation or histomorphometric analysis. Finally, the blocks were placed in HCl for 15 min and the blocks could then be cut to obtain slides for analysis.

One central transverse section per test site was cut with a microtome (4.5 µm thickness). The section was stained with safranin-hematoxylin-eosin (SHE). The same procedure was used for the preparation of the T0 site used for structural characterization and evaluation of the degradation.

Qualitative and semi-quantitative histopathologic evaluation of the local tissue effects and the inflammatory response at injection sites was conducted according using standard methods.

Histomorphometric analysis was conducted on the 31 sections. Each section was analyzed with a color image analyzing system (Tribvn, France, CALOPIX version 3.2.0) to perform a semi-automatic analysis.

A Test Area was defined in a limited area where the print of the granules of the associated material was clear. This area was defined to evaluate the average area and diameter of each microsphere. A Test Area had to contain between 100 and 300 clearly defined granules to be considered as representative. FIG. 2 illustrates a Test Area in a section.

The injected area was the entire area where material was detected on the slide. The Test Area was part of the injected area.

Quantitative measurements were performed either in the Test Area or in the entire injected area.

Quantitative measurements were performed to determine the following parameters:

Number of Granules (Test Area): a manual counting of a representative number of dermal implant granules clearly defined on the slide (no artefact or tears in the print of the associated materials). The number of granules was between 100 and 300 depending on the quality of the slide.

Implant Area ($\mu m^2$) (Test Area): the surface area of granules measured in the Test Area (including any Lacunae Area).

Mean Granule Diameter (µm): Average Diameter of a Granule was calculated from the Implant Area measured in the Test Area using the following formula:

Mean Granule Diameter=2*($\sqrt{}$(average area of a granule/ 4⌠)).

Average Area of a Granule ($\mu m^2$) was calculated from the following formula:

Implant Area (Test Area)/number of granules (Test Area).

Implant Area ($mm^2$) (Injected Area): the surface of granules was measured in the entire injected area (including any Lacunae Area).

Number of Granules (Injected Area): the Implant Area (injected area) was divided by the Average Area of a Granule to obtain the number of Implant Granules in the entire injected area.

Lacunae Area ($mm^2$) (Injected Area): the surface of the "Lacunae" Area was measured as defined by the optically empty spaces corresponding to merged granules (no distinct limits between several granules).

Representative photomicrographs were taken of the areas of interest.

Evaluation and Statistical Analysis

The tested groups were evaluated and compared. Data were expressed as mean±standard error.

Evaluation of local tissue effects was based on the qualitative and semi-quantitative histopathologic evaluation: mean score comparison of the semi-quantitative parameters and comparison of the qualitative histopathologic findings.

Dermal filler degradation was evaluated for each time-period in comparison to the T0 site. The evaluation of the degradation was based on:

Qualitative and semi-quantitative histopathologic evaluation;

Quantitative histomorphometric analysis: The degradation of the dermal filler was evaluated considering the granules residual surface, as well as the number and diameter of the granules variations over time; and Quantitative assessment of the dermal filler volume through micro-CT analysis.

A statistical analysis (one-way, ANOVA or one way ANOVA on ranks followed by Dunnett post-hoc test) was conducted for histomorphometric and micro-CT quantitative parameters using a statistical software (Sigma Plot 14, SPSS Inc.).

Results

FIG. 1 is a graph showing the effect of STS and Saline treatment on dermal filler volume as measured by micro-CT on day 7 after injection. There is a modest (max 10%), but significant, effect of STS treatment (but not of saline treatment) on filler volume (assessed by one-way ANOVA followed by Tukey test).

Figure 2A:
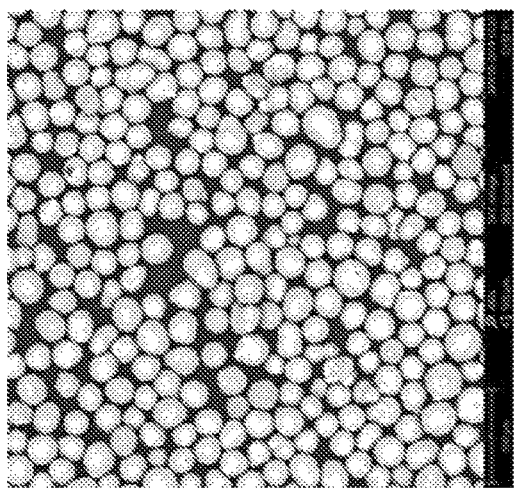
FIGS. 2A-2C are electron micrographs of filler particles isolated from Test sites seven days after filler injection.
Figure 2A:
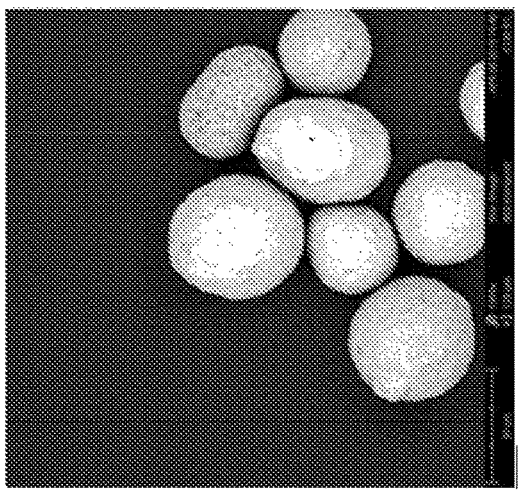
Figure 2B:
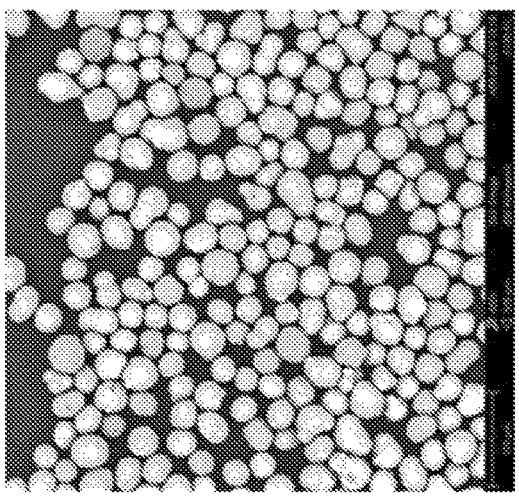
Figure 2B:
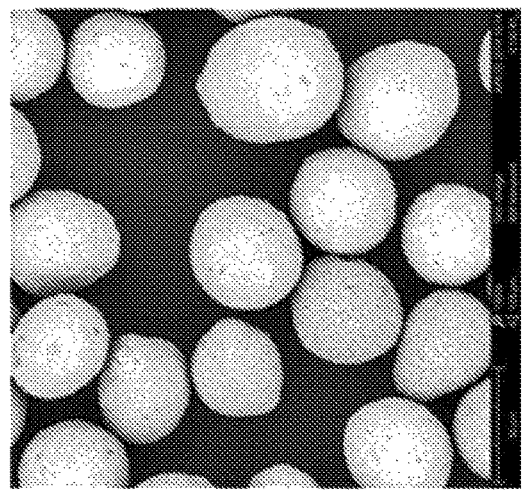
Figure 2C:
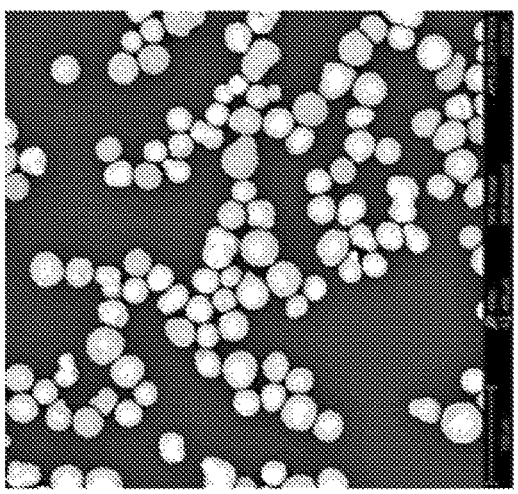
Figure 2C:
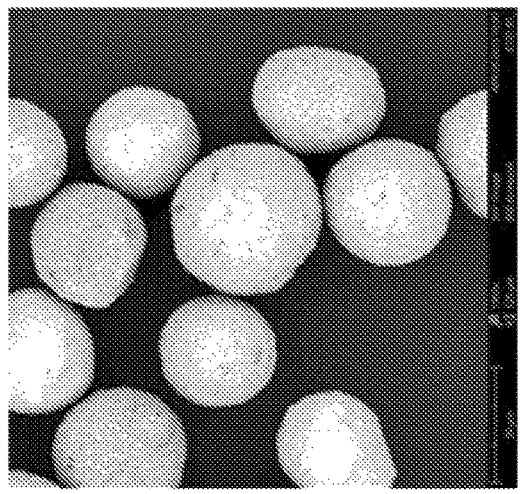

FIGS. 2A-2C are electron micrographs of filler particles isolated from Test sites seven days after filler injection. FIG. 2A shows filler particles from untreated injections of Radiesse® tissue filler in lower magnification (top) and higher magnification (bottom). FIG. 2B shows filler particles from injections of Radiesse® tissue filler treated with 25% w/v STS in lower magnification (top) and higher magnification (bottom). FIG. 2C shows filler particles from injections of Radiesse® tissue filler treated with normal saline in lower magnification (top) and higher magnification (bottom). There is no indication of particle degradation, such as a change in particle size or changes to particle surfaces, on treatment with STS or saline. Table 1 compiles results for measurement by electron microscopy (EM) of mean diameter, D-ratio (shape index, where 1=round), or particle size distribution.

TABLE 1

Effect of STS or Saline on Radiesse ® filler particles by EM

| Treatment | Mean diameter (μm) | D-ratio (–) | <25 μm (wt %) | 25-45 μm (wt %) | >45 μm (wt %) |
|---|---|---|---|---|---|
| STS (25% wt/v) | 29.2 | 0.8 | 1.7 | 93.1 | 5.2 |
| Saline | 28.8 | 0.8 | 1.4 | 93.2 | 5.4 |
| None | 31.9 | 0.9 | 0.9 | 92.3 | 6.9 |

Figure 3:
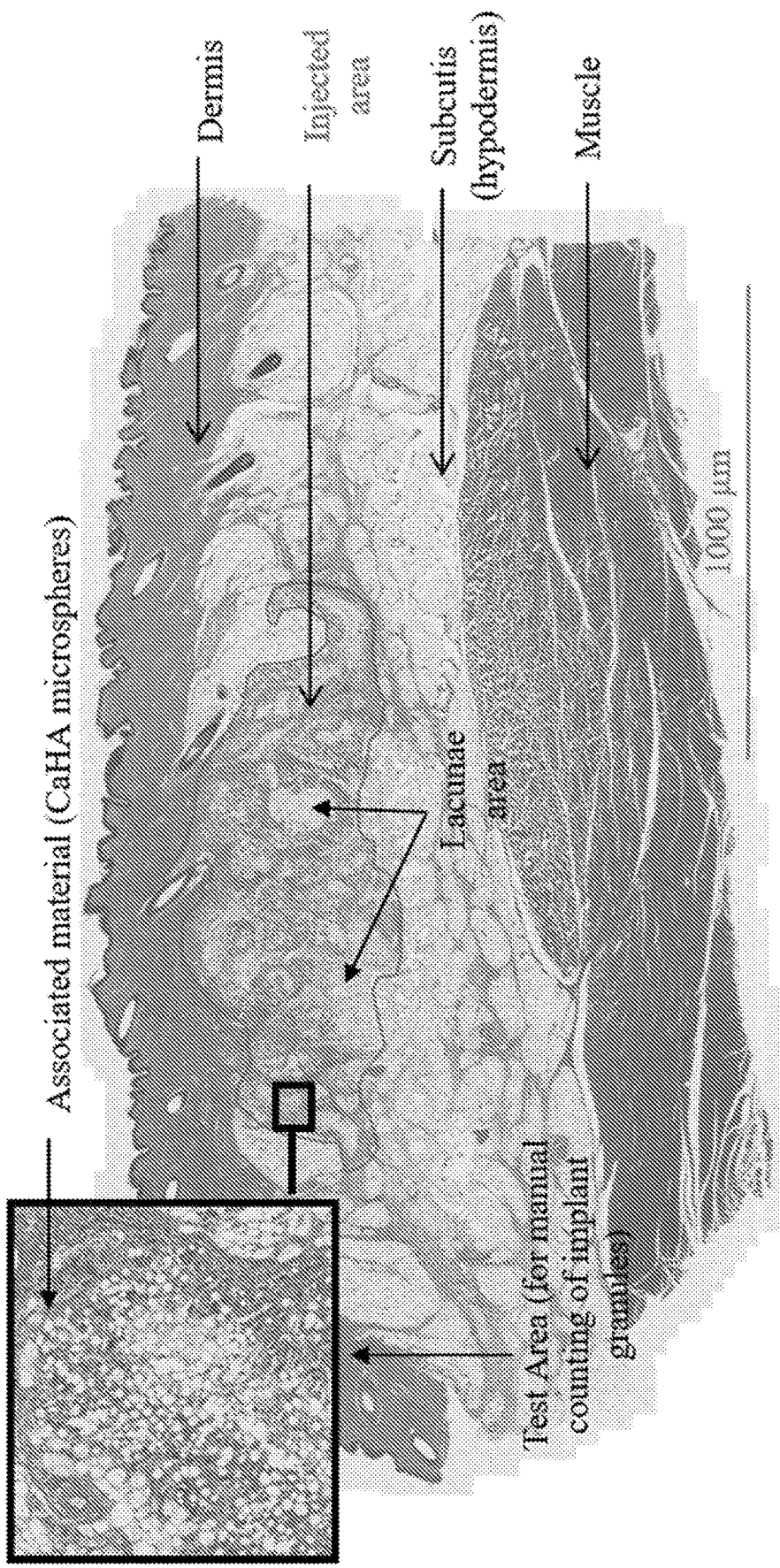
FIG. 3 shows a representative histologic section associated with an injection site. The dermis, subcutis and muscle are indicated. The injection area is indicated b an arrow. A Test Area in the injection area used for manual counting of tissue implant granules (CaHA microspheres) is shown. Lacunae areas in the injection area are shown.

FIG. 3 shows a representative histologic section associated with an injection site. The dermis, subcutis and muscle are indicated. The injection area is indicated in red. A Test Area in the injection area used for manual counting of tissue implant granules (CaHA microspheres) is shown. Lacunae areas in the injection area are shown. Table 2 provides a summary of histopathologic analysis for treatment with STS and saline compared to untreated Radiesse® filler. A * indicates a significant difference $P<0.05$ (one-way ANOVA on ranks followed by Dunnett test).

At seven days, STS treatment results in a decreased amount of filler compared to Saline treatment and untreated injections. STS treatment also shows decreased inflammation (macrophages, giant cells) and increased fibrin content, hemorrhage and necrosis.

Figures 4A, 4B, 4C:
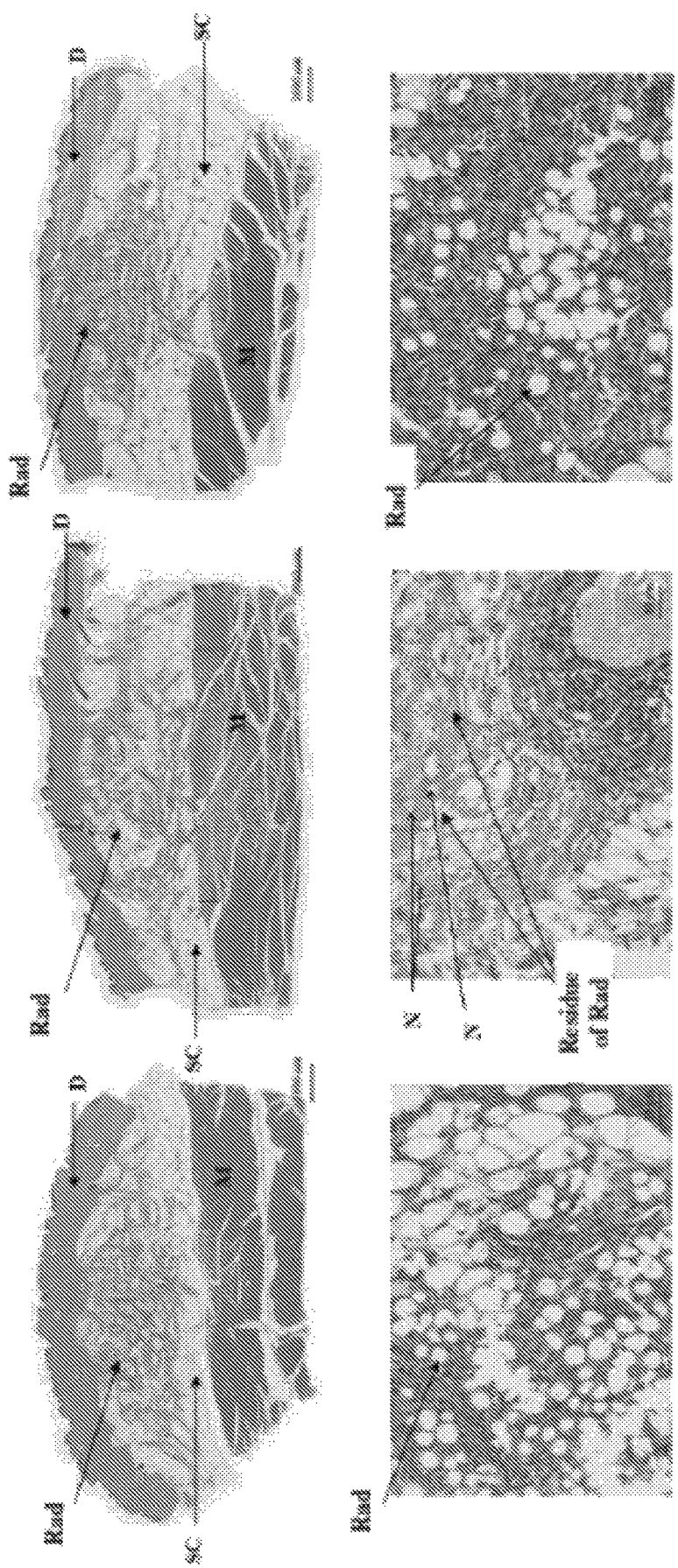
FIGS. 4A-4C are exemplary histology slices stained with safranin, hematoxylin and eosin, with low magnification (upper) and high magnification (lower).

FIGS. 4A-4C are exemplary histology slices stained with safranin, hematoxylin and eosin, with low magnification (upper) and high magnification (lower). FIG. 4A is slice of untreated filler injection. FIG. 4B is slice of filler injection treated with STS. FIG. 4C is slice of filler injection treated with saline. In the figures, Rad is Radiesse® filler, N is necrosis, SC is subcutaneous compartments and D is dermis. The histology samples show more dispersed (diluted) appearance of filler after treatment with STS compared to Saline treatment or untreated filler.

Table 3 provides a summary of quantitative histomorphometric analysis of Test samples, where a significant difference ($P<0.05$, significant difference, one-way ANOVA followed by Dunnett Test) was observed. The results show a significant decrease in the number of filler granules after STS treatment, but not after Saline treatment. The results also show that STS treatment produced a significant decrease in implant area compared to untreated filler and Saline treated filler.

TABLE 2

Summary of the Semi-Quantitative Histopathologic Analysis

| Group/Article | | Macrophages | Lymphocytes | Plasma Cells | Polymorphonuclear Cells | Giant Cells | Necrosis | Fibrosis | Neovascularization | Fatty Infiltrate |
|---|---|---|---|---|---|---|---|---|---|---|
| Rad | Mean | 2.7 | 1.2 | 0.0 | 1.0 | 2.2 | 0.3 | 0.0 | 1.0 | 0.0 |
|  | SD | 0.5* | 0.4 | 0.0 | 0.0 | 0.4* | 0.5* | 0.0 | 0.0 | 0.0 |
| Rad + STS | Mean | 2.0 | 1.1 | 0.0 | 1.1 | 1.4 | 1.2 | 0.0 | 1.0 | 0.0 |
|  | SD | 0.0 | 0.3 | 0.0 | 0.3 | 0.5 | 0.4* | 0.0 | 0.0 | 0.0 |
| Rad + Sal | Mean | 2.4 | 1.3 | 0.0 | 1.0 | 2.0 | 0.1 | 0.0 | 1.0 | 0.0 |
|  | SD | 0.5 | 0.5 | 0.0 | 0.0 | 0.0 | 0.3 | 0.0 | 0.0 | 0.0 |

| Group/Article | | Fibrin | Hemorrhage | Cell or Tissue Degeneration | Fibroblasts | Tissue Integration | Tissue Ingrowth | Encapsulation | AM Degradation |
|---|---|---|---|---|---|---|---|---|---|
| Rad | Mean | 2.0 | 1.2 | 0.0 | 1.8 | 2.7 | 2.7 | 0.0 | 1.0 |
|  | SD | 0.4 | 0.4* | 0.0 | 0.4 | 0.5 | 0.5 | 0.0 | 0.0* |
| Rad + STS | Mean | 2.4 | 2.1 | 0.0 | 2.0 | 2.5 | 2.5 | 0.0 | 1.8 |
|  | SD | 0.5* | 0.3* | 0.0 | 0.0 | 0.5 | 0.5 | 0.0 | 0.4* |
| Rad + Sal | Mean | 1.7 | 1.1 | 0.0 | 2.0 | 2.5 | 2.5 | 0.0 | 1.0 |
|  | SD | 0.5 | 0.3 | 0.0 | 0.0 | 0.5 | 0.5 | 0.0 | 0.0 |

* Indicates statistically significant change

TABLE 3

Summary of Quantitative Histomorphometric Analysis+

| Treatment | Number of granules | Implant area (mm²) |
|---|---|---|
| untreated | 42415 ± 24110 | 19.9 ± 10.0 |
| STS (25% wt/v) | 20103 ± 6101* | 9.4 ± 7.3*# |
| Saline | 39469 ± 14982 | 19.2 ± 6.5 |

+Results expressed as mean ± SD.
*P < 0.05 vs. untreated
P < 0.05 vs. Saline

Example 2

On Day 0, one pig (male, Swine (*Sus scrofa domesticus*), Landrace-Large White cross, 61 kg) received ten (10) SC injections of Radiesse® dermal filler of 500 µl/nodule in the flank (ventral area) (10 nodules in total). One hour after filler injections (T=1 h), 1.5 mL of STS (25% wt/v) were injected into 5 dermal filler nodules in the right flank (ventral area).

A total of 10 CT-scans were performed at 30 min, 1 h 15 min, 1 h 30 min, 1 h 45 min, 2 h, 3 h, 4 h, 8 h, 1 day (24 h) and 7 days after injections of the dermal filler. However, for clarity only data for 2 h, 8 h, 1 day and 7 days are shown. However, for clarity only data for 2 h, 8 h, 1 day and 7 days are shown.

For the injections of STS, the animal received an intramuscular (IM) injection of anesthesia (Zoletil (Tilétamine/Zolazépam—3.75 mg/kg) and Rompun (Xylazine—1.5 mg/kg)). A venous pathway for fluid therapy was introduced and an intubation for the relay of anesthesia with a mix of Isoflurane (1-5%) and oxygen (1-2 L/min) was used in order to maintain the pig under anesthesia during the injections and CT acquisitions. The injection site was shaved, disinfected with a chlorhexidine solution and then rinsed with 70% Alcohol.

CT-Analysis

The X-ray computed tomography (CT) acquisitions were performed with the Computed Tomography Scanner BrightSpeed 16 (General Electric). In order to measure the volume, the mean density and visualize the 3D (Three-dimensional) shape of the dermal fillers SC injected, in vivo CT-scans were performed 1 h 15 (±5 min), 1 h 30 (±10 min), 1 h 45 (±10 min), 2 h (±10 min), 3 h (±15 min), 4 h (±15 min), 8 h (±30 min), 24 h (Day 1+1 h) and 7 days after the test item injections.

During CT acquisition, the pig received an IM injection of anesthesia. Between these CT acquisitions, the animal was under surveillance in a recovery room on a heating mat with fluidotheray. During the CT acquisitions at T=8 h and on Days 1 and 7, the pig received an IM injection of anesthesia (see § III.5.4).

For each CT-scan, the animal was positioned in dorsal recumbency (ventral images) and acquisitions were centered on the injection sites. The parameters of the CT-scan are described in Table 4.

TABLE 4

CT-Scan Parameters

| Imaging system | Scanner BrightSpeed 16 |
|---|---|
| Image number | 1 acquisition (dorsal recumbency) at each time point centered on the injection sites |
| Image format | Dicom format (.dcm) |
| Field of View (FOV) | 36 cm |
| Axial resolution | 703 µm |
| Slice thickness | 625 µm (310 µm after reconstruction) |
| Rotation | 0.8 s |
| Pitch | 0.938 |
| Tension | 120 kV |
| Amperage | 150 mA |
| Algorithms for reconstruction | STANDARD & BONE |

The CT acquisitions were analyzed with Avizo version 9.2.0 software. The objective of this analysis was to assess the elimination over time of the dermal filler injected by SC route after STS injection. To achieve this goal, the evolution of the following parameters was observed over time:
- the volume of each nodule,
- the mean density of each nodule, and
- the 3D shape of each nodule by visualization on the 3D model of each nodule at each time point.

Segmentation

An image segmentation was performed on each CT acquisition using standard reconstruction. First, a manual pre-segmentation was performed around each nodule in order to roughly isolate the voxels corresponding to dermal filler. An interpolation procedure was performed to obtain a contour for each slice and define a Region of Interest (ROI). Second, an automatic segmentation was applied on the ROI previously defined using a global grey level thresholding procedure. The relevant threshold allowing the isolation of the dermal filler products was defined on the basis of the Hounsfield Unit (HU) histogram, following the Otsu method to accurately define the ROI. [see: Vala, H. J., Baxi, A, "A Review on Otsu Image Segmentation Algorithm," International Journal of Advanced Research in Computer Engineering & Technology (IJARCET) Volume 2, Issue 2, February 2013.] The relevant HU threshold for the dermal filler, which is intrinsically radio-opaque, was determined to be +250 HU. All the voxels having a grey level greater than 250 HU were selected to define an ROI corresponding to Pure (not diluted) dermal filler throughout the study. For the STS-treated filler, the relevant HU range was determined to be between 0 HU and +250 HU. Similarly, all the voxels having a grey level in this range were selected in a ROI corresponding to STS-treated diluted dermal filler. Then, a 3D model of these selected voxels was obtained allowing calculation of the total volume (in mm$^3$) of each nodule of non-degraded dermal filler.

Quantification

The volume (in mm$^3$) of the ROI corresponding to each nodule of dermal filler and the mean density (in HU) of each nodule were calculated at each time point.

In order to assess the evolution over time of the elimination of SC-injected dermal filler, the mean volume±standard deviation (SD) and the average of mean density±SD were calculated for each dermal filler injection of the right and left flank separately at each different time points. The evolution of the mean volumes, the mean volume variations and the average of the mean densities of each dermal filler were calculated.

Figure 5:
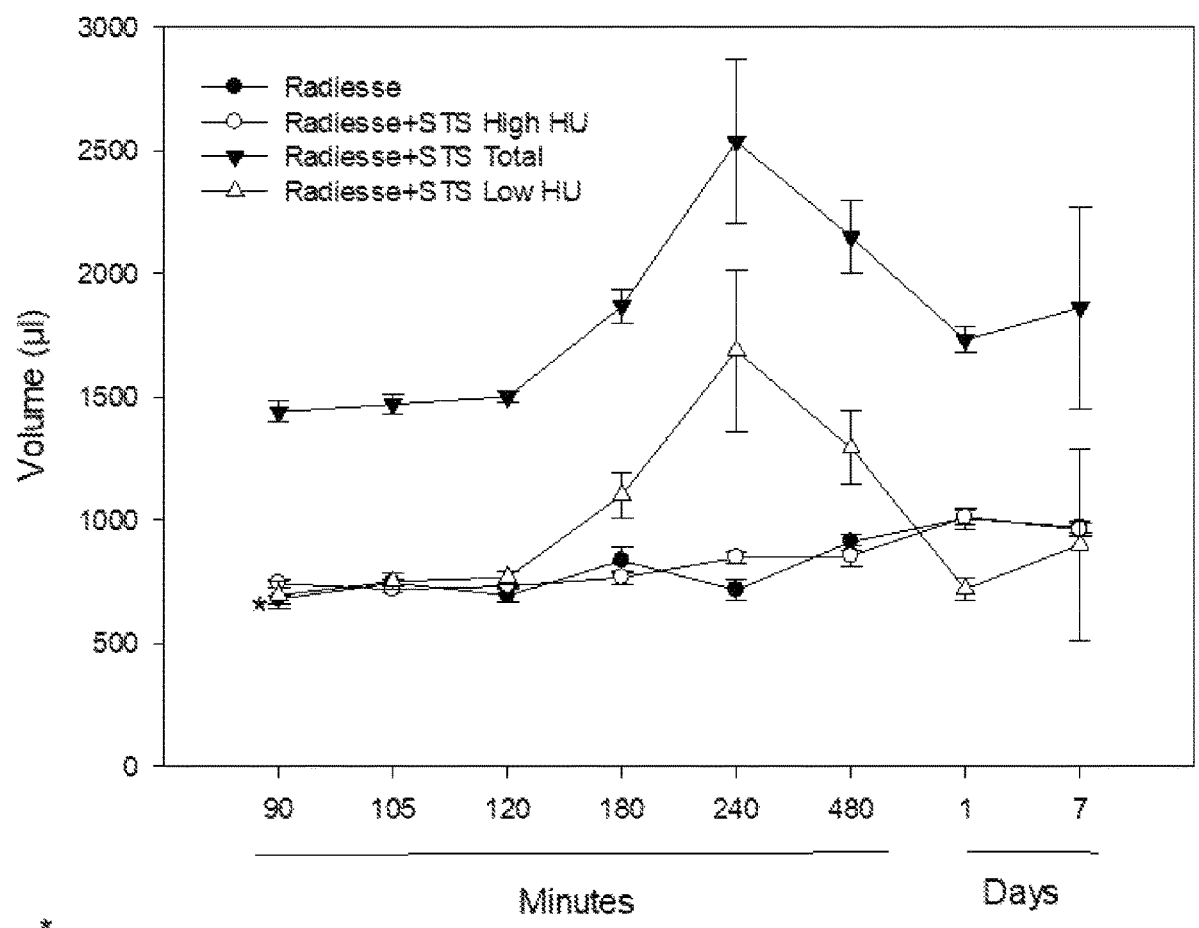
FIG. 5 is a graph showing the change of filler volume with time as analysed using CT. Note that Radiesse®+STS high is defined as unchanged filler (HU=250–infinity), while Radiesse®+STS low is defined as affected filler (diluted, degraded or dispersed). The Radiesse®+STS total is the sum of both.

FIG. 5 is a graph showing the change of filler volume with time as analysed using CT. Note that Radiesse®+STS high is defined as unchanged filler (HU=250-infinity), while Radiesse®+STS low is defined as affected filler (diluted, degraded or dispersed). The Radiesse®+STS total is the sum of both. There is a significant, but very modest temporary increase in Radiesse®+STS high volume vs. that of untreated filler (Radiesse) 90 minutes after injection. For all other time points there was no difference in the volume between Radiesse® filler vs. Radiesse®+STS. Interestingly, the volume of Radiesse®-STS (low) increases with the time between 120 and 240 minutes indicating increase of more diluted/dispersed fraction. This could indicate that water is taken up by Radiesse® filler which transits from High to Low fraction.

Figure 6:
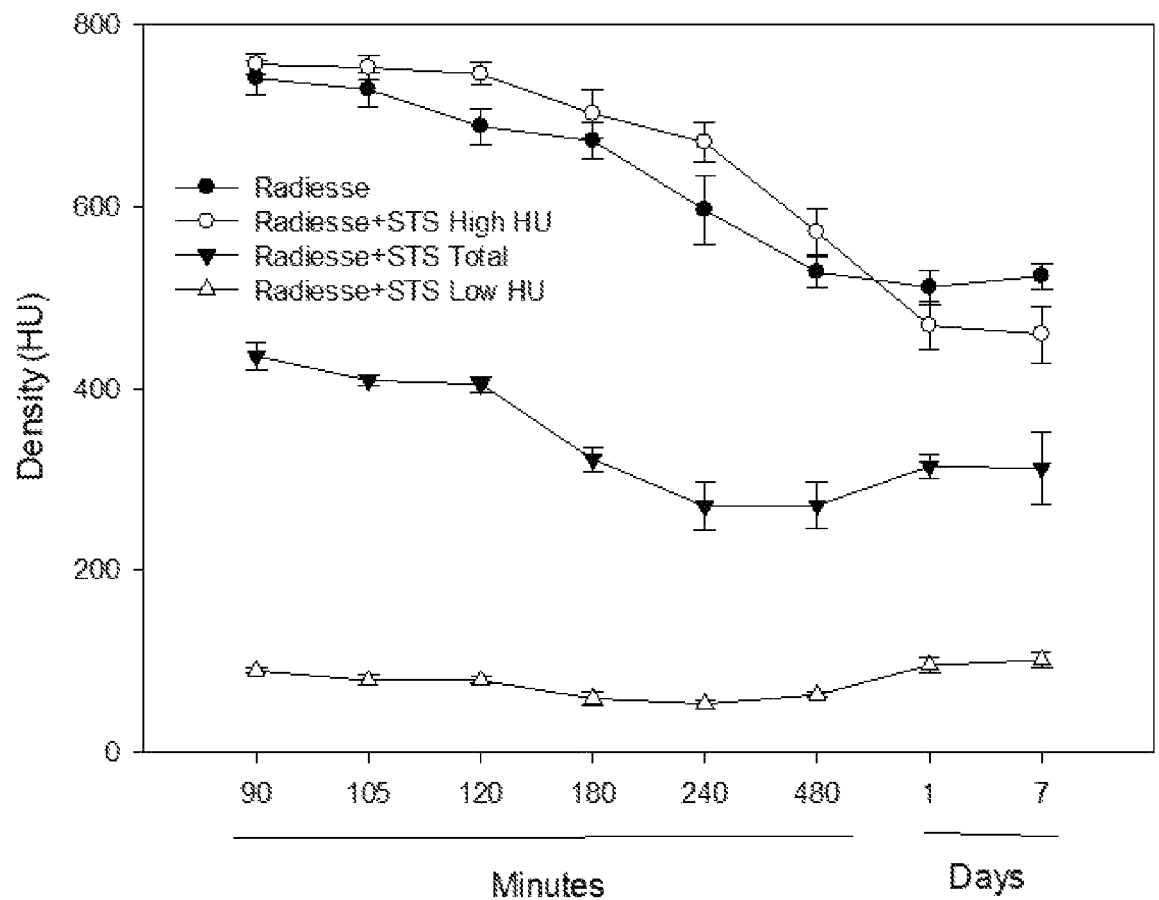
FIG. 6 is a graph similar to that of FIG. 5, but shows the change in filler density with time as analyzed using CT.

FIG. 6 is a graph similar to that of FIG. 5, but shows the change in filler density with time as analyzed using CT. At day 7, there appears to be a strong trend for a decrease of Radiesse®+STS high density compared to untreated filler. At earlier time points, e.g. 105-480 min, an opposite trend for higher density in Radiesse®+STS groups can be observed. This could result from the "pulling out" of water from the area defined However, at the decrease of density at 7 days could be interpreted as an increase in dispersion of Radiesse® filler after STS, i.e. the particles are spaced more apart.

Figure 7:
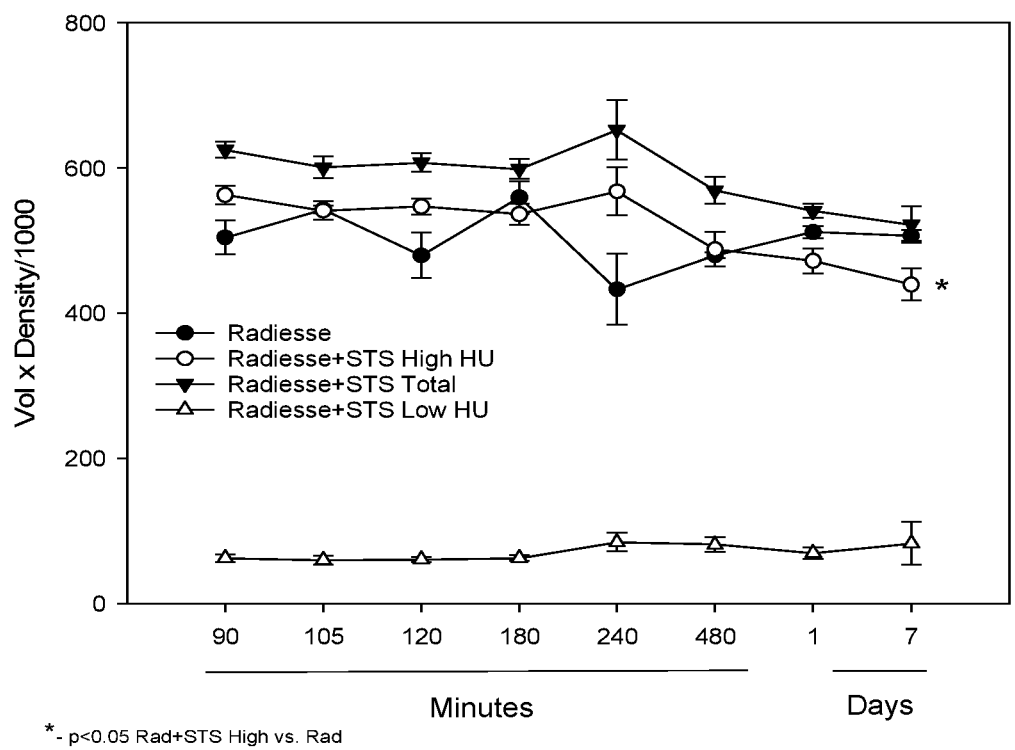
FIG. 7 is a graph showing the change in filler volume× density/1000 (a measure of filler content) with time as analyzed by CT.

FIG. 7 is a graph showing the change in filler volume× density/1000 (a measure of filler content) with time as analyzed by CT. On day 7, there is a significant decrease of filler in the Radiesse®+STS high fraction and a parallel trend for increase of filler in the Radiesse®+STS low fraction. This change reflects transition of filler particles to more dilute fractions. This transition may be prerequisite for filler degradation by increasing filler accessability to cellular machinery. FIGS. 5-7 show that in spite of no significant change of the volume, the amount of Radiesse® filler in high density fraction decreases, when mean fraction density is taken into account.

Figure 8A:
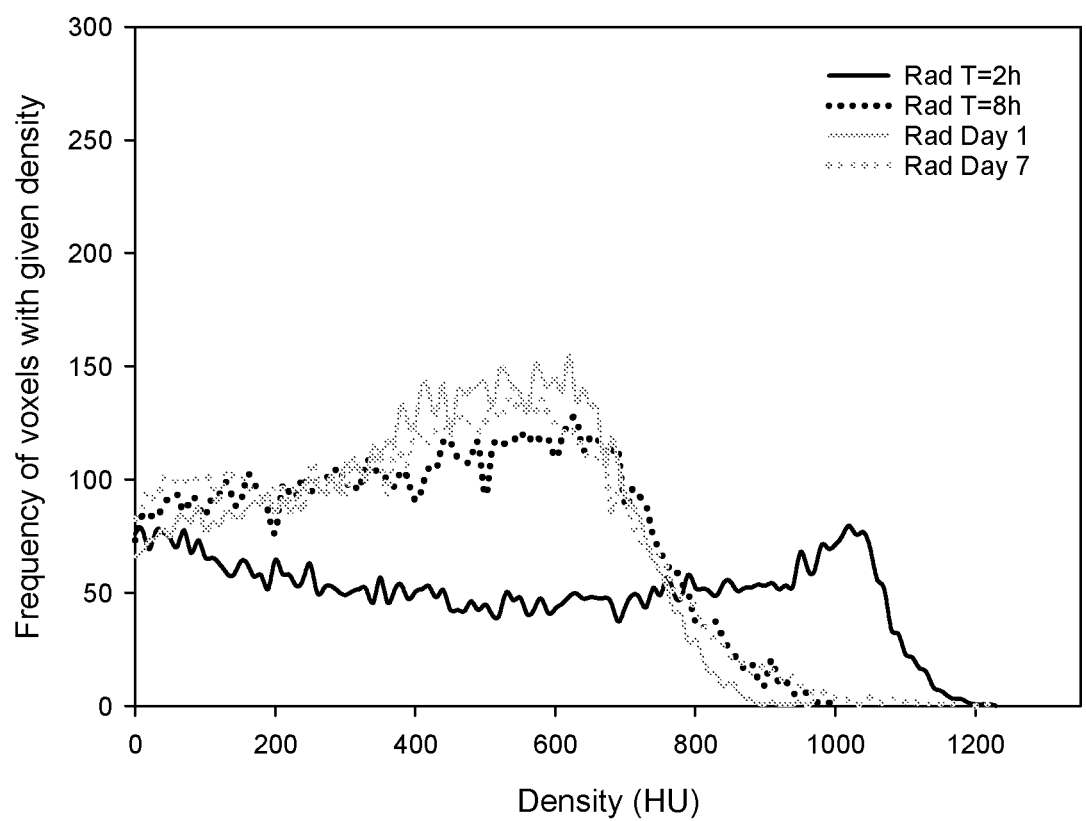
FIGS. 8A-8B are graphs of certain CT data of Example 2. The graphs show HU density units on the X-axis and the number of voxels (which are 3D pixels, from the CT scans of a selected injection site/nodule) having that HU value. The graphs represent voxel frequency.
Figure 8B:
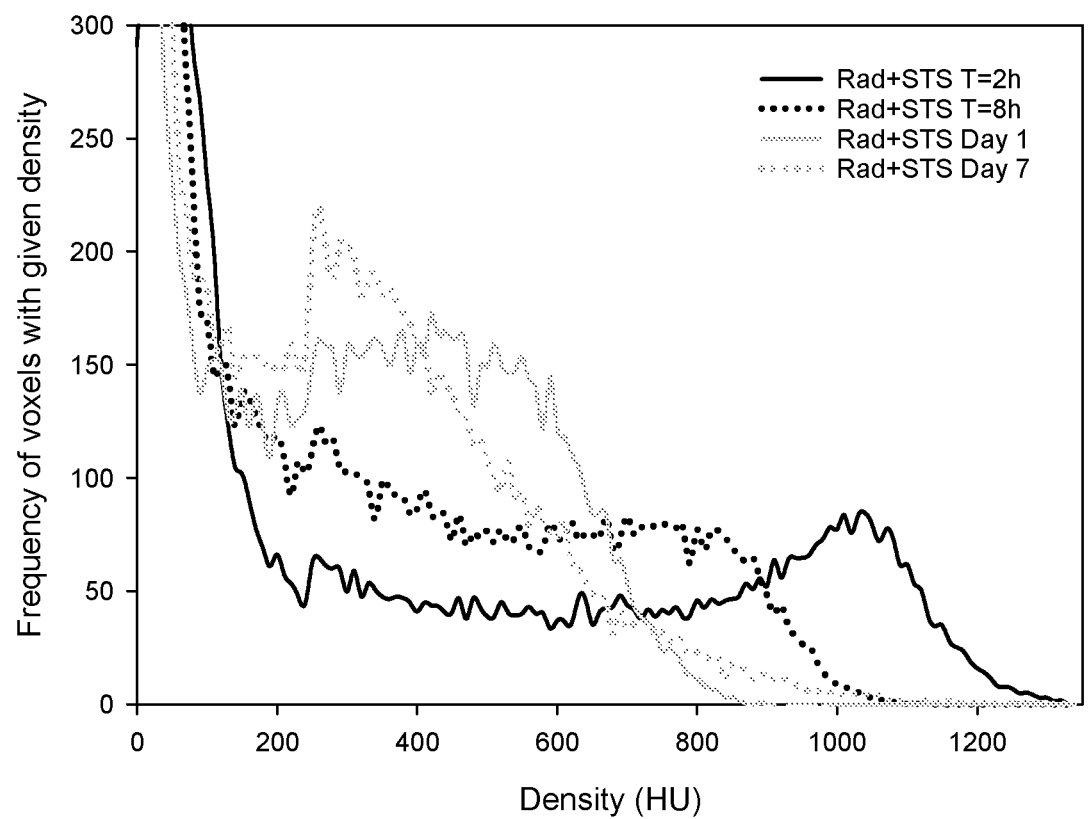

FIGS. 8A-8B are graphs of certain CT data of this example. The graphs show HU density units on the X-axis and the number of voxels (which are 3D pixels, from the CT scans of a selected injection site/nodule) having that HU value. The graphs represent voxel frequency. FIG. 8A data are from CT scans of the untreated filler nodule. FIG. 8B data are from CT scans of an injection nodule treated with STS (as described above). A comparison of the traces in the two figures show the difference in time evolution of dilution of filler in STS-treated filler and untreated filler. Traces on both graphs are for selected time points of CT scans. Shortly after (1 hr) injection of STS (not shown) there is no significant difference in treated and untreated nodules at short time. However, with time the number of voxels with low HU (as described above) increases more after STS treatment than in untreated filler. For example, for trace at day 7, the highest HU values for untreated filler are between 450-570 HU, while for the STS-treated nodules, the highest HU values are 250-400 HU below 100 HU. This comparison indicates that filler is "diluted" with time faster after STS treatment than in untreated filler. After STS treatment more filler "moves" to segmentation below 250 HU (which is considered "affected" filler). For example, if you compare the figures at day 7 at 750 HU, for the untreated filler there are c.a. 70 voxels and for STS-treated filler there are c.a. 40 voxels. The increase at 8 hr of high HU voxels after STS treatment (e.g. at 800 HU) may be related to water uptake induced the high osmolality of the STS solution which results in temporal shift in filler density to the right. The data comparison illustrated in FIGS. 8A-8B allow a more nuanced and detail comparison of temporal changes on treatment than is possible when CT data are averaged over HU ranges.

Example 3

On Day 0, each of eight pigs (male, Swine (*Sus scrofa domesticus*), Landrace-Large White cross, 50-60 kg) received ten (10) SC injections of Radiesse® dermal filler of 500 µl/nodule in the flank (ventral area) (10 nodules in total). One hour after filler injections (T=1 h), 1.5 mL of selected solutions (Table 5, solutions 0-8, test items, solution 0 is normal saline and not hyperosmotic) were injected each into 9 dermal filler nodules in the right flank (ventral area).

A total of 7 CT-scans were performed at 1 h 15, 2 h, 4 h, 1 day (24 h), 3, 7 and 14 days after injection of the dermal filler. The clinical state of each animal is assessed once a week by body weight measurement and clinical observations.

On day 14, one pig received one SC injection of Radiesse® filler in order to represented a Day 0 injection which is considered a positive control and then, all pigs were euthanized and each nodule with a part of the skin, along with negative control skin (skin samples without injection), were sampled in order to perform histological analysis of, for example, the inflammation, the necrosis and the dermal filler presence at the injection site.

For the injection of the test items, animals received an intramuscular (IM) injection of anesthesia (Zoletil (Tilétamine/Zolazépam—3.75 mg/kg) and Rompun (Xylazine—1.5 mg/kg)). Then, a venous pathway for fluid therapy was performed and an intubation for the relay of anesthesia with a mix of Isoflurane (1-5%) and oxygen (1-2 L/min) was used in order to maintain pigs under anesthesia during the injections and CT acquisitions.

The injection sites were shaved, disinfected with a chlorhexidine solution and then rinsed with 70% alcohol. The day before injection, the test solutions were prepared as described in Table 5. In detail, each solution was shaken using stirring plate for about 1 h at room temperature and the solutions were left closed at room temperature overnight. On the day of injection, each solution is introduced into a syringe (2.5 mL) for injection.

The 10 SC injections of dermal filler on Day 0 were performed in the ventral area, (five nodules on each flank of the ventral area) for each pig. For each SC nodule, a theoretical volume of 500 µl was administered. One hour (±5 min) after injection of dermal filler, SC injection of the different solutions (prepared the day before) were performed into nine (9) nodules of dermal. For each SC nodule, a theoretical volume of 1.5 mL of test solution was administered.

On Day 14, 500 µl of Radiesse® dermal filler was SC injected in one pig before euthanasia, in order to obtain a control skin which represented a Day 0 injection.

To calculate the exact volume administered for each SC injections (Radiesse® filler and test solutions), the syringes (having 100 µl scale) were weighed before and after each injection. The difference in syringe weight (grams) was converted to injected volume (µl), using the density of each test solution.

SC injections were performed with a 27G needle for the Radiesse® dermal filler. All the other test solution SC injections were performed with 26G needles.

The X-ray computed tomography acquisitions were performed with the Computed Tomography Scanner BrightSpeed 16 (General Electric). In order to measure the volume and the mean density and to visualize the 3D shape of the dermal filler (Radiesse® filler with or without test solution) injected, in vivo CT-scans were performed on Day 0: 1 h 15 (±10 min), 2 h (±15 min) and 4 h (±20 min), on Day 1 (24 h+1 h), Day 3, Day 7 and Day 14.

During CT acquisition on Day 0, the pigs received an IM injection of anesthesia. The animals were maintained under anesthesia until the CT acquisition at T=2 h (2 h after dermal filler injection session). Between these CT acquisitions, the animals were under surveillance in the recovery room on a heating mat with fluidotherapy. At the end of the CT acquisition at T=2 h, the pigs received a tattoo around each injected site. During the CT acquisitions at T=4 h and on Days 1, 3, 7 and 14, pigs received an IM injection of anesthesia. For the CT-scans, animals were positioned in dorsal recumbency and acquisitions were centered on the injection sites. The parameters of the CT-scan are described in Table 5.

TABLE 5

CT Scan Parameters

| | |
|---|---|
| Imaging system | Scanner Brightspeed 16 by General Electric |
| Image number | 1 acquisition (dorsal recumbency) at each time point centered on the injection sites |
| Image formal | Dicom format (.dcm) |
| Field of View (FOV) | 35 cm (The FOV could be modified according to the height of the pigs and will be mentioned in raw data and study report) |
| Axial resolution | 683 μm |
| Slice thickness | 625 μm (310 μm after reconstruction) |
| Rotation | 0.8 s |
| Pitch | 0.938 |
| Tension | 120 kV |
| Intensity | 150 mA |
| Algorithms for reconstruction | STANDARD & BONE |

On Day 14, animals were euthanized under anesthesia (IM injection of Zoletil (Tilétamine/Zolazépam—3.75 mg/kg) and Rompun (Xylazine—1.5 mg/kg)) by a lethal injection of pentobarbital (0.35 mL/Kg)

Next, a sample (approximate size of 5×5 cm) of each injection site/nodule was sampled and attached to a piece of cork to prevent skin folding. One site of Radiesse® dermal filler injected on Day 14 and three sites of un-injected skin were also sampled and considered as positive and negative controls, respectively. Then, each sample was fixed and prepared for histological analysis.

Image Analysis and Quantification Procedures

The CT acquisition was analyzed with the software Avizo version 9.2.0. The objective of this analysis was to assess the degradation over time of the dermal filler injected by SC route after injection of different test solutions. To achieve this goal, the evolution of three parameters was observed over time:
  the volume of each nodule (treated and untreated nodules),
  the mean density of each nodule (treated and untreated nodules), and
  the 3D shape of each nodule by visualization on the 3D model of each nodule at each time point (treated and untreated nodules).

The shape of the nodules changed during the study and tended to appear with a flattened shape, mainly on Day 14 (end of the study). All the nodules were still visible at the end of the study, except for the nodules injected with Calcium Chloride which largely degraded/dispersed the Radiesse® dermal filler and lead to a large wound on pigs.

Figure 14:
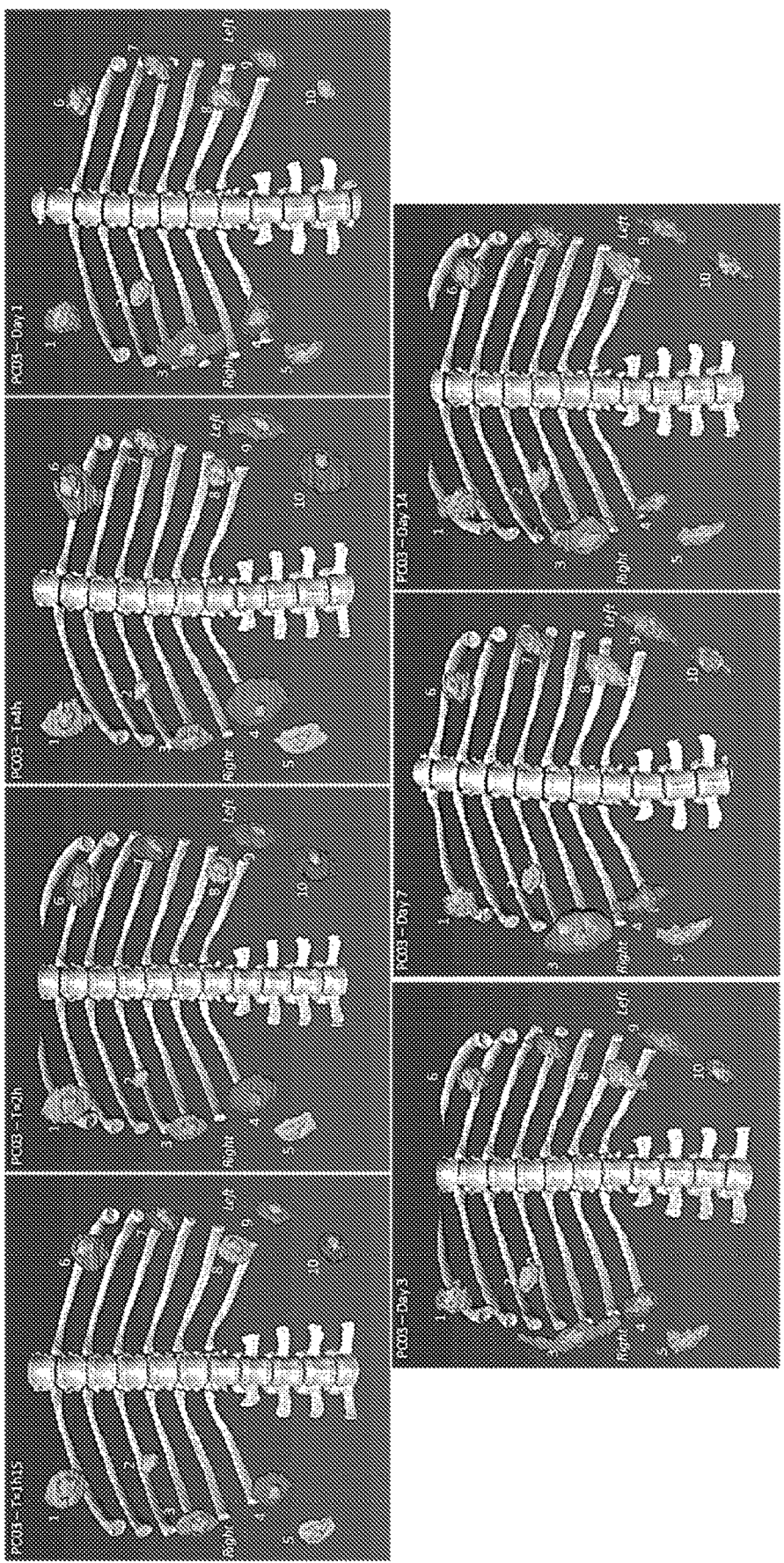
FIG. 14. Exemplary 3D models of nodules from Example 3 in pig PC03 from T=1 h 15 to Day 14. Radiesse® filler nodules in pink. 1—Magnesium Sulfate Heptahydrate. 2—Sodium Chloride 90 mg/ml. 3—Radiesse® dermal filler (alone). 4—Calcium Chloride. 5—Sodium Dihydrate Phosphate. 6—Sucrose. 7—Glycerol. 8—D-Glucose. 9—Sodium Chloride 9 mg/ml. 10—Sodium Acetate).
Figure 15:
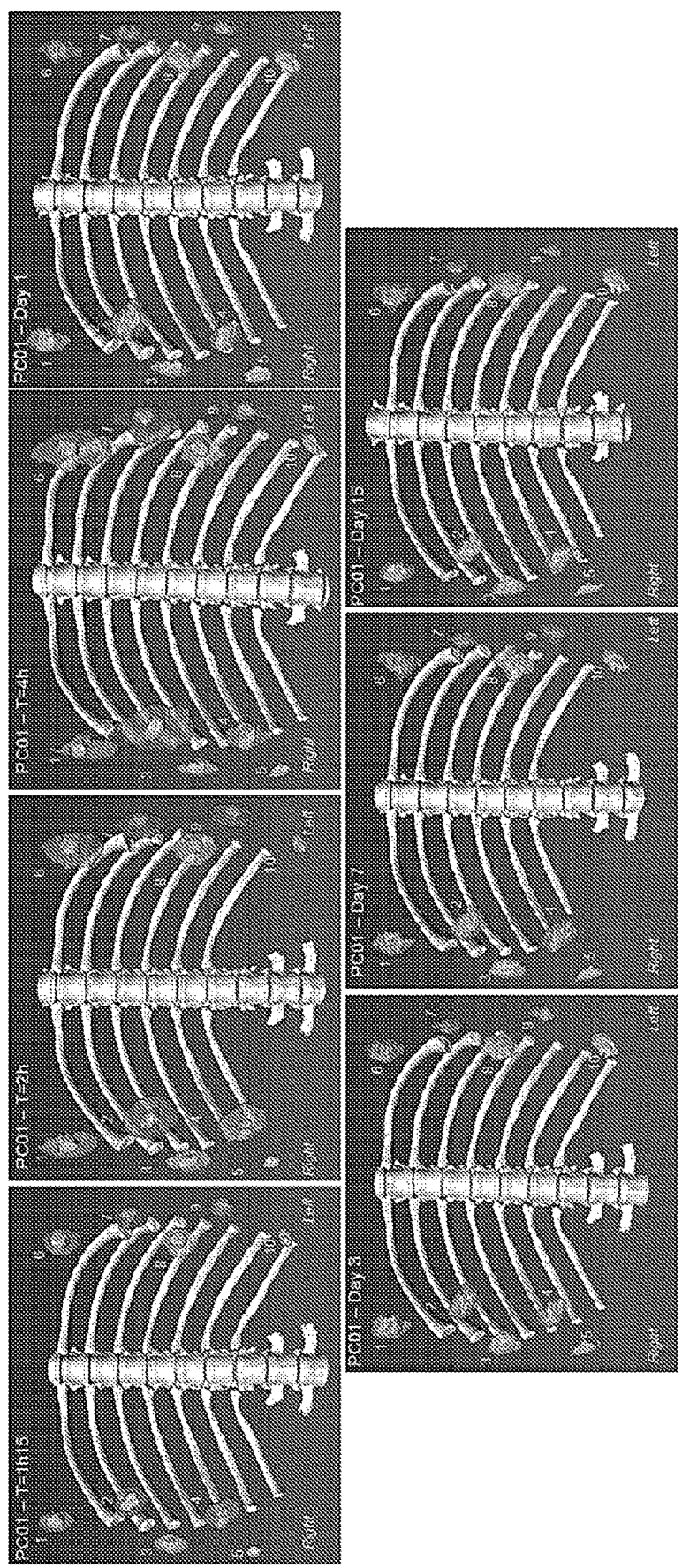
FIG. 15. 3D models of nodules from Example 4 in pig PC01 from T=1 h 15 to Day 15. Radiesse® filler nodules in pink. (1 & 6)—Magnesium Chloride Hexahydrate. (2 & 7)—Fructose. (3 & 8)—Sodium Hydrogen Carbonate. (4 & 9)—Trisodium Citrate Dihydrate. (5 & 10)—Radiesse® dermal filler (alone).
Figure 16:
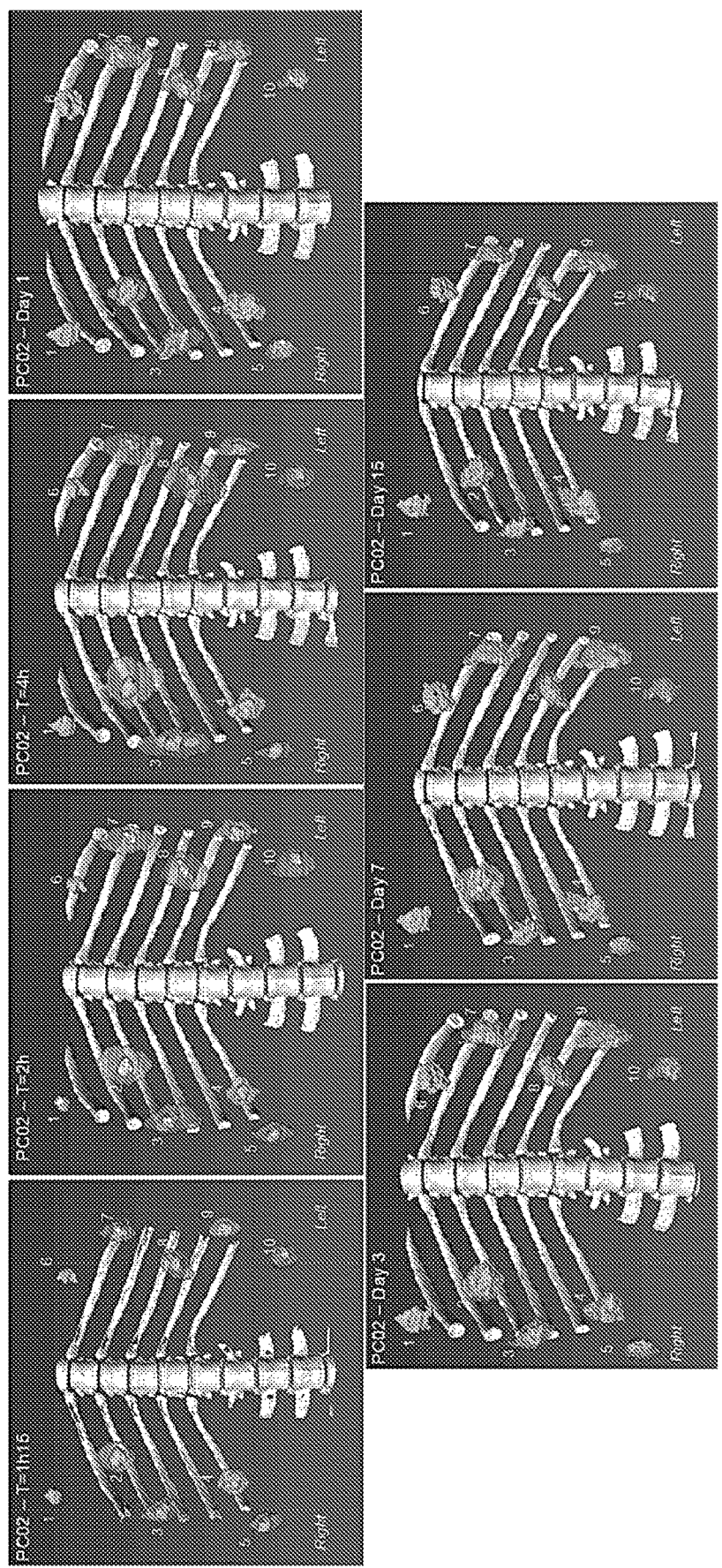
Figure 17:
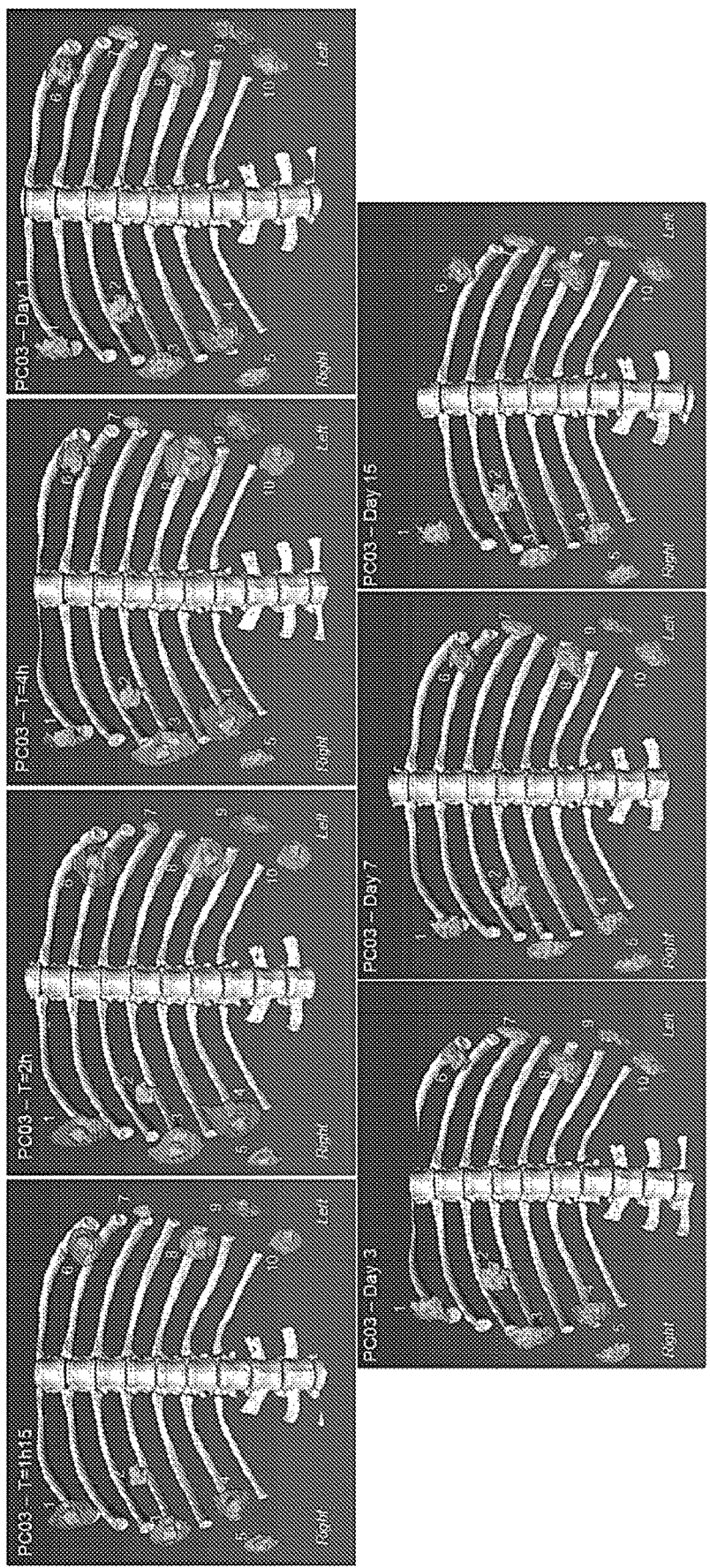
FIG. 17. 3D models of nodules from Example 4 in the pig PC03 from T=1 h 15 to Day 15. Radiesse® dermal filler nodules in pink. (1 & 6)—Trisodium Citrate Dihydrate. (2 & 7)—Radiesse® dermal filler (alone). (3 & 8)—Magnesium Chloride Hexahydrate. (4 & 9)—Fructose. (5 & 10)—Sodium Hydrogen Carbonate.
Figure 18:
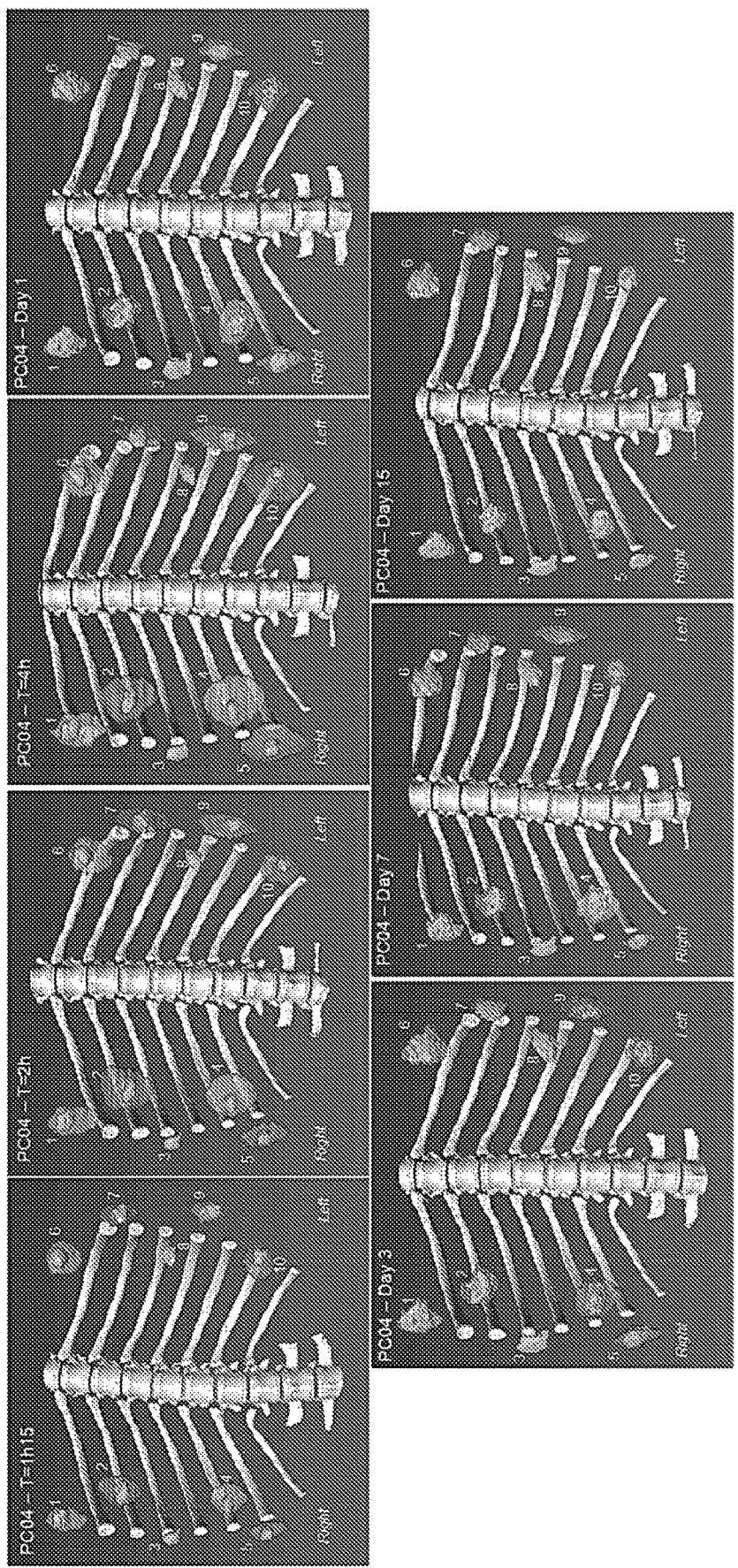
FIG. 18. 3D models of nodules from Example 4 in the pig PC04 from T=1 h 15 to Day 15. Radiesse® filler nodules in pink. (1 & 6)—Sodium Hydrogen Carbonate. (2 & 7)—Trisodium Citrate Dihydrate. (3 & 8)—Radiesse® dermal filler (alone). (4 & 9)—Magnesium Chloride Hexahydrate. (5 & 10)—Fructose.

The 3D shape evolution was assessed by visualization of the 3D model of each nodule. In order to visualize the evolution over time of the 3D shape of Radiesse® dermal filler alone and injected with different solutions, an example of the shape evolution of the 3D models of nodules from Day 0+1 h 15 to Day 14 is presented in FIG. 14.

The nodules of Radiesse® dermal filler presented an oval shape 1 h 15 after injection. In addition, the shape of Radiesse® filler nodules changed over time and nodules appeared more flattened and became rougher until Day 14 (end of the study) and was slightly more visible in Radiesse® dermal filler nodules injected with each solution compared to Radiesse® filler nodules without injection.

These observations can be explained by dilution of the Radiesse® dermal filler with the solution.

Segmentation:

An image segmentation processing was performed on each CT acquisition. First, a manual pre-segmentation was performed around each nodule in order to roughly isolate the voxels corresponding to dermal filler product, which defined a Region of Interest (ROI). Second, an automatic segmentation was applied on the previously defined ROI using a global grey level thresholding procedure. The relevant threshold allowing the isolation of the dermal filler product were defined on the basis of the Hounsfield Unit (HU) histogram, following the Otsu method (N. Otsu (1979) A threshold selection method from gray-level histograms. IEEE Transactions On Systems, Man and Cybernetics 9:62-66) to accurately define the ROI. In previous study (T19WG), the relevant HU threshold for Radiesse® dermal filler, which is intrinsically radio-opaque, was determined at +250 HU. All the voxels having a grey level greater than 250 HU were grouped in a ROI and considered to correspond to the Radiesse® dermal filler.

Table 6 lists exemplary hyperosmotic solutions useful in the methods of the present invention.

TABLE 6

Exemplary Hyperosmotic Solutions

| No. | Tonicity Modifier | Formula | M [g/mol] | m [mg] | V [mL] | c [mg/mL] | c [mM] | Estim. Osmolality [mosmol/kg] |
|---|---|---|---|---|---|---|---|---|
| 0 | Sodium chloride* | NaCl | 58.4 | 180 | 20 | 9 | 154 | 308 |
| 1 | Sodium chloride | NaCl | 58.4 | 1800 | 20 | 90 | 1540 | 3080 |
| 2 | Sodium dihydrogen phosphate dihydrate | $NaH_2PO_4 \cdot 2H_2O$ | 156.0 | 4680 | 20 | 234 | 1500 | 3000 |

TABLE 6-continued

Exemplary Hyperosmotic Solutions

| No. | Tonicity Modifier | Formula | M [g/mol] | m [mg] | V [mL] | c [mg/mL] | c [mM] | Estim. Osmolality [mosmol/kg] |
|---|---|---|---|---|---|---|---|---|
| 3 | Sodium acetate | $NaC_2H_3O_2$ | 82.0 | 2461 | 20 | 123 | 1500 | 3000 |
| 4 | Calcium chloride | $CaCl_2$ | 111.0 | 2220 | 20 | 111 | 1000 | 3000 |
| 5 | Magnesium sulfate heptahydrate | $MgSO_4 \cdot 7H_2O$ | 246.5 | 7394 | 20 | 370 | 1500 | 3000 |
| 6 | Glycerol | $C_3H_8O_3$ | 92.1 | 5525 | 20 | 276 | 3000 | 3000 |
| 7 | Glucose | $C_6H_{12}O_6$ | 180.2 | 3603 | 20 | 180 | 1000 | 1000 |
| 8 | Sucrose | $C_{12}H_{22}O_{11}$ | 342.3 | 6846 | 20 | 342 | 1000 | 1000 |
| 9 | Sodium citrate, dihydrate | $Na_3C_6H_5O_7 \cdot 2H_2O$ | 294.1 | 1471 | 20 | 73.5 | 250 | 1000 |
| 10 | Fructose | $C_6H_{12}O_6$ | 180.2 | 3603 | 20 | 180 | 1000 | 1000 |
| 11 | Fructose | $C_6H_{12}O_6$ | 180.2 | 10809 | 20 | 540 | 3000 | 3000 |
| 12 | Magnesium chloride, hexahydrate | $MgCl_2 \cdot 6H_2O$ | 203.2 | 1354 | 20 | 68 | 333 | 1000 |
| 13 | Magnesium chloride, hexahydrate | $MgCl_2 \cdot 6H_2O$ | 203.2 | 4062 | 20 | 204 | 1000 | 3000 |
| 14 | Sodium hydrogen carbonate (sodium bicarbonate) | $NaCHO_3$ | 84.0 | 840 | 20 | 42 | 500 | 1000 |

*Normal saline, not hyperosmotic

It will be apparent to one of ordinary skill in the art that hyperosmotic solutions of the listed tonicity modifiers of varying osmolality between 1000-5000 milleosmol/Kg can be readily prepared.

Experiments were undertaken to assess whether different hyperosmotic solutions exhibit an effect on Radiesse® volume as analyzed by CT and histology. On day 0, a farm pig received ten (10) SC injections of Radiesse® dermal filler 0.5 mL (ventral area) (10 nodules in total). One hour after filler injections (T=1 h), 1.5 mL of one of eight test hyperosmotic solutions (1-8 solutions, Table 5) was injected at an injection site. One injection site was untreated and one injection site was treated with normal saline (0.9% wt/v NaCl). It was noted that injection of 1M $ClCl_2$ resulted in severe skin necrosis.

Results presented in Table 7 indicate that treatment with certain hyperosmotic solutions, particularly hyperosmotic NaCl, produces significant decreased volume at the filler injection site after 7 and 14 days. In contrast, treatment with normal saline does not produce significant decreased volume at the filler injection site at these times. Additionally, at 7 and 14 days $CaCl_2$), glycerol and sodium acetate produce a significant effect at these times. It should be however stressed that $CaCl_2$) produced strong local irritating effect and is not preferred for use in the methods herein. A trend to decrease volume of filler was observed after treatment with sucrose solution, however this failed to reach significance (P=0.06-0.07) at day 14. Table presents results for Example 3 and Example 4.

TABLE 7

Change in Volume on Treatment with Certain Hyperosmotic Solutions Shown as percent of Injected Volume). Combined Results from Examples 3 and 4.

| Treatment | | Inject. volume (μL) | Time after Treatment | | | | | | |
|---|---|---|---|---|---|---|---|---|---|
| | | | Day 0 + 1 h 15 | Day 0 + 2 h | Day 0 + 4 h | Day 1 | Day 3 | Day 7 | Day 14/15 |
| Untreated 1[#] | Mean | 501.32 | 147.22 | 152.20 | 171.92 | 207.30 | 214.90 | 214.52 | 190.45 |
| | SD | 19.25 | 5.30 | 7.37 | 12.42 | 9.02 | 19.52 | 17.06 | 6.20 |
| $CaCl_2$ (sol 4) 1M 3000 mosmol/Kg | Mean | 499.08 | 170.60* | 162.46 | 157.72 | 145.42* | 174.24* | 175.91* | 169.73* |
| | SD | 15.83 | 7.69 | 11.52 | 17.71 | 19.27 | 23.74 | 40.50 | 7.31 |
| Sodium dihydrogen phosphate (sol 2) 1.5M 3000 mosmol/Kg | Mean | 512.10 | 156.57 | 151.58 | 164.27 | 198.42 | 201.11 | 201.97 | 179.72* |
| | SD | 33.73 | 10.07 | 10.25 | 8.03 | 13.14 | 19.93 | 39.22 | 18.73 |
| Sucrose (sol 8) 1M 1000 mosmol/Kg | Mean | 498.10 | 167.87* | 167.63 | 190.95 | 202.96 | 207.85 | 199.72 | 180.45 |
| | SD | 18.96 | 10.34 | 10.44 | 17.80 | 8.12 | 16.03 | 14.46 | 16.00 |

TABLE 7-continued

Change in Volume on Treatment with Certain Hyperosmotic Solutions Shown as percent of Injected Volume). Combined Results from Examples 3 and 4.

| Treatment | | Inject. volume (µL) | Day 0 + 1 h 15 | Day 0 + 2 h | Day 0 + 4 h | Day 1 | Day 3 | Day 7 | Day 14/15 |
|---|---|---|---|---|---|---|---|---|---|
| Glycerol (sol 6) 3M 3000 mosmol/Kg | Mean SD | 515.61 24.20 | 151.48 6.15 | 156.43 5.72 | 184.92 7.45 | 200.32 10.53 | 197.65* 17.59 | 197.62* 13.53 | 173.93* 12.79 |
| Glucose (sol 7) 1M 1000 mosmol/Kg | Mean SD | 497.52 13.61 | 159.49* 9.53 | 170.39* 11.15 | 199.02* 25.12 | 211.88 12.86 | 210.20 17.91 | 204.43 19.57 | 185.65 15.78 |
| Normal Saline (sol 0) 154 mM 308 mosmol/Kg | Mean SD | 502.30 10.62 | 155.02 5.96 | 159.42 6.50 | 182.97 15.64 | 209.66 9.20 | 215.48 13.54 | 212.85 17.20 | 187.72 4.75 |
| Hyperosmotic Saline (sol 1) 1.54M 3080 mosmol/Kg | Mean SD | 512.05 25.02 | 161.28* 5.25 | 157.58 5.81 | 164.59* 7.43 | 202.75 14.64 | 199.27 9.52 | 192.06* 17.72 | 175.89* 11.09 |
| Sodium Acetate (sol 3) 1.5M 3000 mosmol/Kg | Mean SD | 507.35 21.24 | 152.73 10.94 | 154.89 6.26 | 165.88 10.05 | 202.12 11.42 | 197.50* 13.58 | 189.13* 19.40 | 176.61* 12.35 |
| Magnesium sulfate (sol 5) 1.5M 3000 mosmol/Kg | Mean SD | 491.71 29.27 | 170.49* 19.89 | 159.33 11.82 | 158.84* 10.60 | 188.43 14.50 | 206.26* 8.47 | 202.32 23.33 | 186.95 19.72 |
| Untreated 2[#] | Mean SD | 502.1 9.7 | 1417 69 | 1511 97 | 1787 126 | 2216 105 | 2112 177 | 2176 361 | 1998 141 |
| Fructose (sol 11) 3.0M 3000 mosmol/Kg | Mean SD | 5009 118 | 1581* 94 | 1610 111 | 1871 177 | 2285 80 | 1959 133 | 2002 303 | 1930 99 |
| Sodium Hydrogen Carbonate (sol 14) 0.5M 1000 mosmol/Kg | Mean SD | 5035 61 | 1529* 95 | 1561 132 | 1799 79 | 2214 81 | 2014 214 | 2345 663 | 1977 98 |
| Trisodium Citrate Dihydrate (sol 9) 0.25M 1000 mosmol/Kg | Mean SD | 5081 105 | 1488 79 | 1571 96 | 1901 147 | 2210 128 | 2010 146 | 2243 475 | 1969 163 |
| Magnesium chloride hexahydrate (sol 13) 1.0M 3000 mosmol/Kg | Mean SD | 5076 106 | 1527* 78 | 1502 58 | 1511* 94 | 1920* 94 | 2139 94 | 2197 349 | 1989 122 |

*Significant decrease in volume compared to untreated 1 or 2 filler ($p < 0.05$ two tailed Student t test)
[#]Untreated 1 and Untreated 2 indicated two groups of experiments (Example 3 and Example 4, respectively)

Example 4: Assessment by X-Ray Computed Tomography of the Behaviour of Dermal Filler Subcutaneously Injected in a Pig Model after Injection of Different Hyperosmotic Solutions This Example assessed the behavior of Radiesse® dermal filler subcutaneously (SC) injected in pigs, after injection of different hyperosmotic solutions into the Radiesse® filler nodules. The changes over time of the volume and the mean density of Radiesse® filler and of each different solution were assessed by CT-scans at selected time points between Day 0 and Day 15. The nodule 3D shape was also assessed over time by visualizing the 3D model of each nodule. Finally, on Day 15, each nodule was sampled for histological analysis to detect inflammation, necrosis and the remaining material.

The CT-scanner analyses showed that the volume of Radiesse® dermal filler expanded from injection through Day 1 potentially due to a change in water content (water tapping) and then, remained relatively stable until Day 15. With injection of Magnesium Chloride solution into the Radiesse® filler nodule, the volume of the nodule increased more slowly than without injection of solution. The mean density of the filler nodule was observed to decrease more slowly than without injection of solution. These results are consistent with Magnesium Chloride solution slowing down water tapping. However, on Day 15, irrespectively of the solution injected, volume and mean density of Radiesse® filler nodules without injected solution was similar to those of Radiesse® filler nodules with injected solutions.

A difference was observed for the Magnesium Chloride and Fructose solutions compared to the Sodium Hydrogen Carbonate and Trisodium Citrate solutions for the volume (which increased until T=4 h or T=2 h) and for the mean density (which decreased until T=4 h or T=2 h).

In addition, 3D models showed that the Radiesse® dermal filler was slightly rougher and more split after injection of solutions than without injection of solution.

Thus, the CT-scans showed that the Radiesse® dermal filler with or without injection of different hyperosmotic solutions had an expansion phase between Day 0 and Day 1 and when injection of Magnesium Chloride was performed the volume increases more slowly than with solution. This observation is consistent with injection of Magnesium Chloride solution tending to slow down the water tapping of the Radiesse® dermal filler.

Most of the complications associated with dermal fillers concern inappropriate injection placement or volume. Methods for correction of such complications are unavailable or limiting.

Therefore; the aim of this Example was to assess by X-ray Computed Tomography (CT-scanner) the behavior of Radiesse® dermal filler after subcutaneous (SC) injection of different hyperosmotic solutions in pigs, which may lead to a dispersion of Radiesse dermal filler.

Pigs are injected by SC route with Radiesse® filler without Lidocaine (Test item). One hour after the Radiesse® filler injection, selected different hyperosmotic solutions are injected by SC route into the dermal filler nodules. For two Radiesse® filler nodules per pig, no additional product is injected; these nodules are used as controls.

The evolution over time of the volume and mean density of the Radiesse® filler nodules with injection of the different solutions are assessed by CT-scanner at selected time points: on Day 0, at about 1 hour (h) and 15 minutes (min), 2 h and 4 h after the Radiesse® filler injection and solution injection, and then, on Day 1 (about 24 h after Radiesse® filler injection), Day 3, Day 7 and Day 15.

The nodule 3D shape is also assessed over time by visualization of the 3D model of each nodule (Radiesse® filler with or without hyperosmotic solution injection).

Finally, on Day 15, each nodule is sampled for histological analysis in order to detect inflammation, necrosis and the dermal filler presence at the injection sites.

Materials and Methods

Tables 8-10 provide a description of the test items, test item characteristics and animal model characteristics.

TABLE 8

Test item characteristics (P20WK-EE-01, -02 and -03).

| reference | P20WK-EE-01 | P20WK-EE-02 | P20WK-EE-03 |
|---|---|---|---|
| Denomination | Radiesse ® dermal filler | Magnesium Chloride Hexahydrate | Fructose |
| Description | Calcium Hydroxylapatite based dermal filler | Solid material, inorganic salt ($MgCl_2$ $6H_2O$) | Solid material, sugar-like compound ($C_6H_{12}O_6$) |
| Provided form | 23 syringes of 1.5 ml | 250 g of powder in a plastic bottle | 250 g of powder in a plastic bottle |
| Concentration provided | 56% Ca Hydroxy Apatite, 44% carrier | Not applicable | |
| Density | 1.65 g/cm$^3$ | 1.1 g/cm$^3$ after dissolving | |

TABLE 9

Test item characteristics (P20WK-EE-04 and -05).

| reference | P20WK-EE-04 | P20WK-EE-05 |
|---|---|---|
| Denomination | Sodium Hydrogen Carbonate | Trisodium Citrate Dihydrate |
| Description | Solid material, inorganic salt ($NaHCO_3$) | A Solid material, organic salt ($C_6H_5O_7Na_3$ $2H_2O$) |
| Provided form | 250 g of powder in a plastic bottle | 250 g of powder in a plastic bottle |
| Concentration provided | Not Applicable | |
| Density | 1.1 g/cm$^3$ | |

TABLE 10

Animal model characteristics.

| | |
|---|---|
| Species/Strain | Pig (*Sus scrofa domesticus*) |
| Provider | GAEC des 4 vents |
| Sex | Male |
| Number | 4 |
| Age | Not communicated by the provider |
| Weight | 51.8 ± 4.6 kg on 2 Mar. 2020 [DEV2] |

Figure 9A:
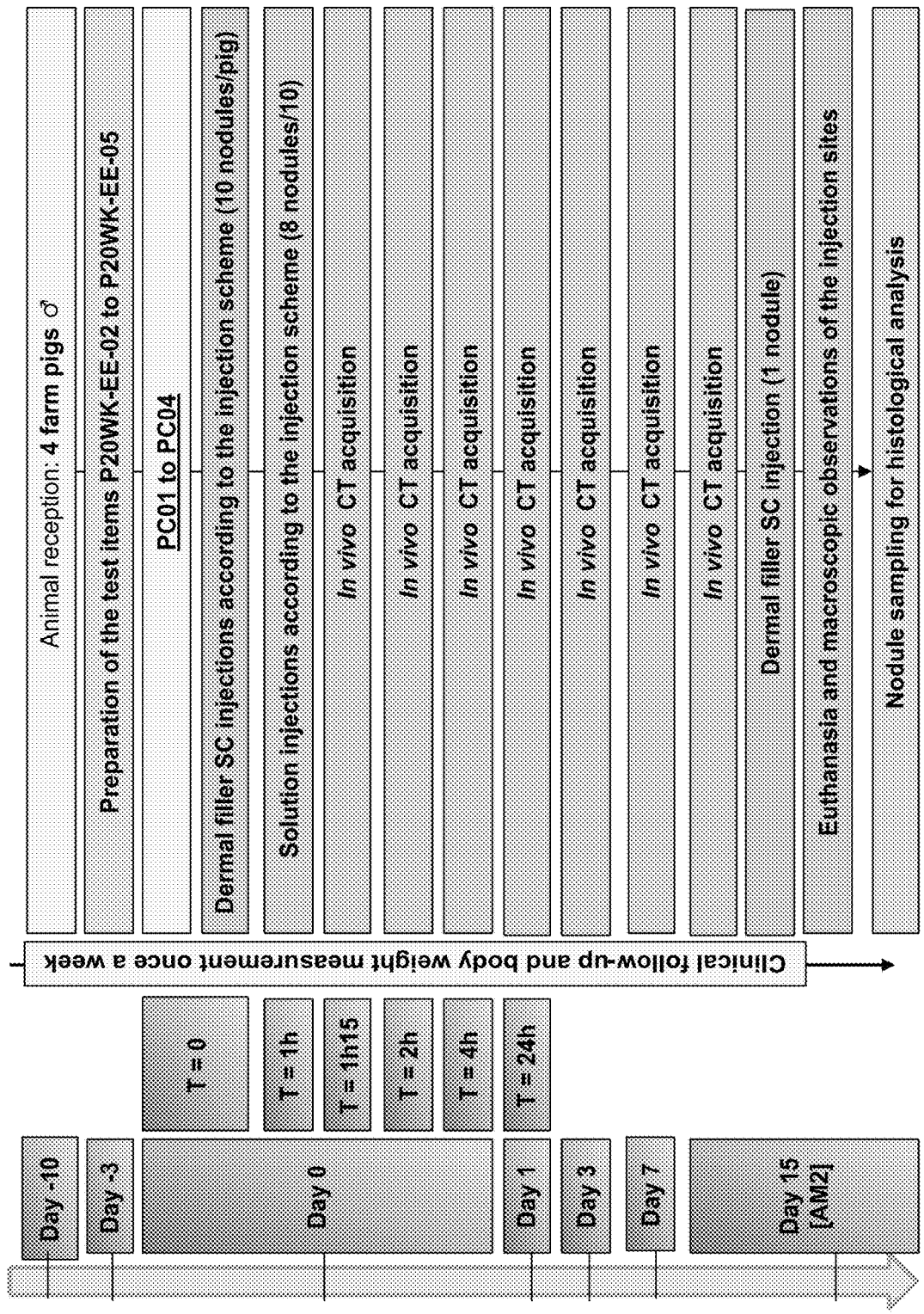
FIGS. 9A-9C. Study design for experimental phases for Example 4.
Figure 9B:
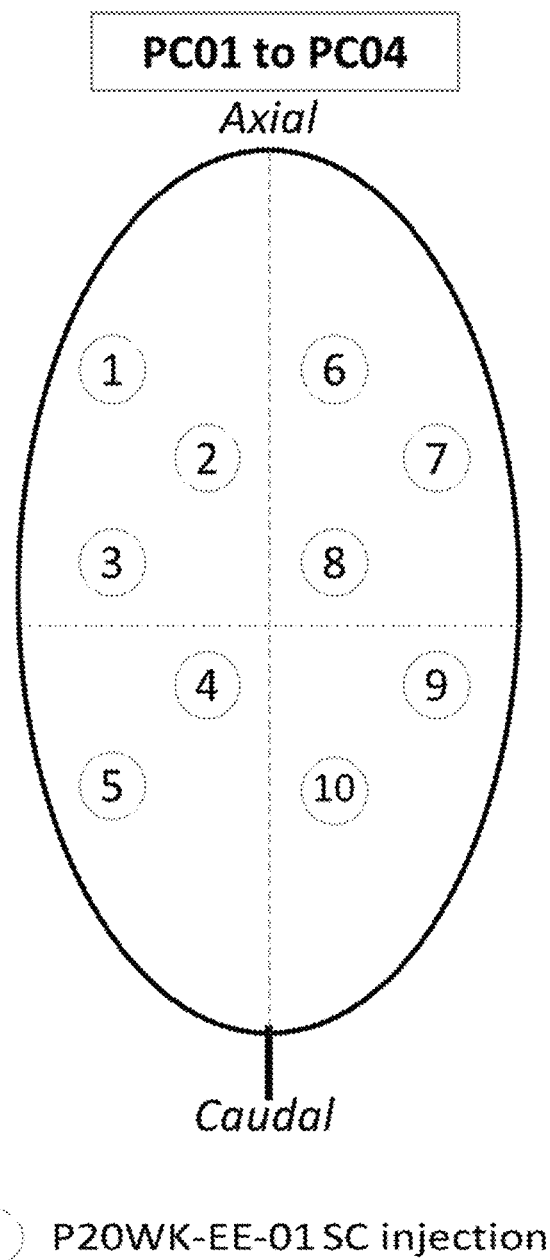
Figure 9C:
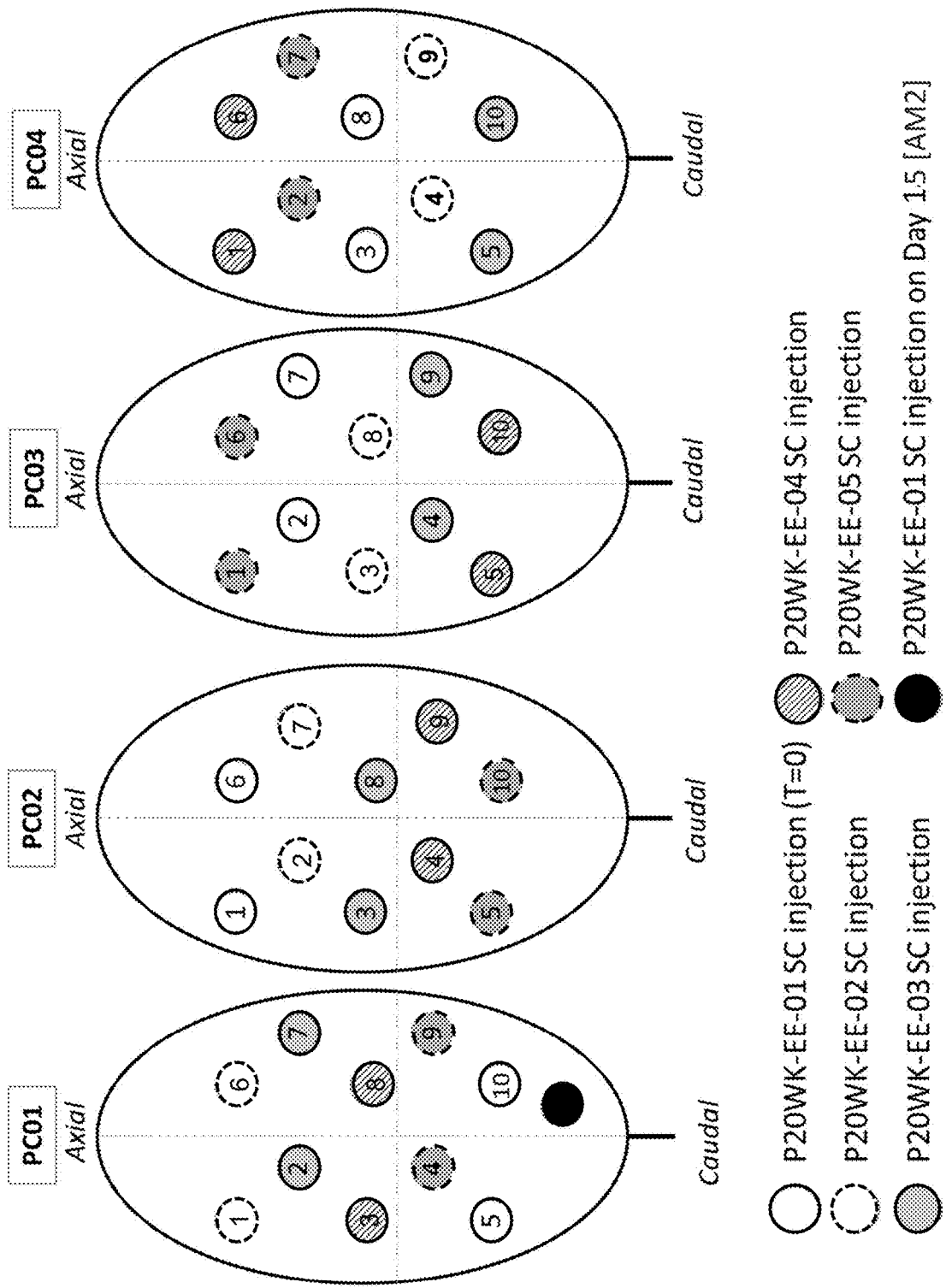

Table 11 and FIGS. 9A-9C provide a description and characteristics of the study design.

On Day 0, 4 pigs received ten (10) SC injections of Radiesse® dermal filler (P20WK-EE-01) of about 500 μl/nodule in the flank (ventral area) at T=0. One hour after Radiesse® dermal filler injections (T=1 h), about 1.5 ml of different hyperosmotic solutions (P20WK-EE-02 to P20WK-EE-05) were each injected into 8 Radiesse® filler nodules. Two Radiesse® filler nodules per animal were not injected with hyperosmotic solution and served as controls. The scheme of injection is presented in FIGS. 9A-9C.

TABLE 11

Study design.

| | |
|---|---|
| Animal model Identification | Pigs PC01 to PC04 (number) 1097-01 to 1097-04 (ear tag and number) |
| Test item preparation | Day - 3 |
| Test item injections on Day 0 - T = 0 | See FIG. 9B |
| Volume of injection | 500 μl per nodule of P20WK-EE-01 SC injected |
| Test item injections on Day 0 - T = 1 h ± 5 min | See: FIG. 9C |
| Volume of injection | 1.5 ml per nodule P20WK-EE-02 to P20WK-EE-05 inside Radiesse nodules |
| CT acquisitions | T = 1 h 15 ± 10 min T = 2 h ± 15 min T = 4 h ± 20 min T = 24 h (Day 1) ± 1 h Day 3 Day 7 Day 15 |
| Radiesse SC injection (positive control sample) | Day 15 (one nodule before euthanasia on pig PC01) |
| Euthanasia/Macroscopic observation and sampling of injection sites | Day 15 |

A total of 7 CT-scans were performed at 1 h 15±10 min, 2 h±15 min, 4 h±20 min, 1 day (24 h±1 h), 3, 7 and 15 days after injection of the dermal filler, as described in FIG. 9A. Test item injections on Day 0-T=0 are shown in FIG. 9B. Test item injections on Day 0-T=1 h±5 min are shown in FIG. 9C.

The clinical state of the animal was assessed at least once a week by body weight measurement and clinical observations.

Eventually, on Day 15, pig PC01 received one SC injection of Radiesse® dermal filler to represent a Day 0 injection and this nodule was considered as a positive control for histological analyses. Then, all pigs were euthanized and each nodule, with a part of the skin, along with positive (1 skin sample with Radiesse® filler injection) and negative control skin (3 skin samples without injection site), were sampled, fixed in Ethanol 70% and embedded in MMA (methyl methacrylate) blocks in order to perform histological analysis of inflammation, necrosis and the dermal filler present at the injection sites.

Table 12 provides a description of the Experimental Phase Schedule.

TABLE 12

Experimental phase schedule.

| Day | Action (V), Test Site No 1 (B), Test Site No 2 LLS Rowiak (L) and Test Site No 3 NOVOTEC (N) | |
|---|---|---|
| Days-10 | B | Reception of 4 pigs for acclimation period and health checks |
| Day-3 | V | Test item preparation |
| Day 0 T0 | | SC injections of the Radiesse ® dermal filler according to the injection scheme described in FIG. 9B. (10 nodules/pig) (4 PC) |
| T = 1 h | | Injections of the hyperosmotic solutions inside Radiesse ® dermal filler nodules according to the injection scheme described in FIG. 9C. (8 nodules/pig) (4 PC) |
| T = 1 h 15 | | CT acquisitions (4 PC) |
| T = 2 h | | CT acquisitions (4 PC) |
| T = 4 h | | CT acquisitions (4 PC) |
| Day 1 T = 24 h | | CT acquisitions (4 PC) |
| Day 3 | | CT acquisitions (4 PC) |
| Day 7 | | CT acquisitions (4 PC) |
| Day 15 | | CT acquisitions (4 PC) |
| | V | Radiesse ® dermal filler SC injection (positive control sample - one nodule pig PC01) |
| | B | Euthanasia |
| | V | Nodule macroscopic observations |
| | V | Nodules with a part of skin and control skin sampling for preparation and histological analysis |

Preparation of the Test Items:

On Day−3, the test items (except Radiesse® dermal filler which was provided ready to use) were prepared as described below:

P20WK-EE-02 (Magnesium Chloride Hexahydrate): 5108 mg of product powder were dissolved in 25.1 mL of distilled water (water for injection) concentration 1000 mM, osmolarity 3000 mosmol/kg;

P20WK-EE-03 (Fructose): 13588 mg of product powder were dissolved in 25.1 mL of distilled water (water for injection) concentration 3000 mM, osmolarity 3000 mosmol/kg;

P20WK-EE-04 (Sodium Hydrogen Carbonate (Sodium bicarbonate)): 1068 mg of product powder were dissolved in 25.4 mL of distilled water (water for injection) concentration 500 mM, osmolarity 1000 mosmol/kg; and P20WK-EE-05 (Trisodium citrate dihydrate): 2015 mg of product were dissolved in 27.4 mL of distilled water (water for injection) concentration 250 mM osmolarity 1000 mosmol/kg.

Then, each solution was mixed using a magnetic stir bar and stirring plate for about 1 h at room temperature. The solutions were left closed at room temperature until the day of injection (Day 0). The day of injection, each solution was mounted on syringe of 2.5 ml for injection.

Preparation of Pigs:

For the test item injections, pigs received an IM injection of anesthesia (Zoletil (Tiletamine/Zolazepam—3.75 mg/kg) and Rompun (Xylazine—1.5 mg/kg)). Then, a venous pathway for fluid therapy was performed and an intubation for the relay of anesthesia with a mix of Isoflurane (1-5%) and oxygen (1-2 L/min) was used in order to maintain pigs under anesthesia during the injections and CT acquisitions until T=2 h. The injection site was shaved, disinfected with a chlorhexidine solution and then rinsed with 70% Alcohol solution.

Injection of the Test Items:

On Day 0 (TO), 10 SC injections of test item P20WK-EE-01 (Radiesse® dermal filler) were performed in the ventral area (five nodules on each flank of the ventral area). For each SC nodule, a theoretical volume of 500 μL was administered. One hour (±5 min) after injection of dermal filler, SC injections of the different solutions (prepared on Day −3) were performed into 8 nodules of dermal filler. For each injection of solution, a theoretical volume of 1.5 mL was administered (see, e.g., injection scheme in Table 11).

At the end of the CT acquisitions at T=2 h, pigs received tattoos around each injected site in order to visualize the injection site and to facilitate sampled them on Day 15.

On Day 15, a theoretical volume of 500 μL of Radiesse® dermal filler was SC injected in pig PC01 (1097-01), before euthanasia, to obtain a positive control skin which represented a Day 0 injection.

SC injections were performed with 26G needles both for the dermal filler and the hyperosmotic solutions. The same syringe and needle were used for several injections of dermal filler (3 maximum). For the injection of the other solution, one different syringe and needle were used for each nodule.

In order to calculate the exact volume administered for each SC nodule (Radiesse and hyperosmotic solutions), the syringes (having 100 μl scale) were weighed before and after each SC injection. To convert the syringe weights (grams) in injected volume (μl), the density of each test item is evaluated, as described above.

Computed Tomography Acquisition

The X-ray computed tomography acquisitions were performed with the Computed Tomography Scanner BrightSpeed 16 of General Electric.

In order to measure the volume, the mean density and to visualize the 3D shape of the dermal filler SC injected (in presence or absence of different hyperosmotic solutions), in vivo CT-scans were performed on Day 0: 1 h 15 (±10 min), 2 h (±15 min) and 4 h (±20 min), on Day 1 (24 h±1 h), Day 3, Day 7 and Day 15.

On T=0, during CT acquisition, pigs received an IM injection of anesthesia (see Table 12, FIG. 9B).). Pigs were maintained under anesthesia until CT acquisition at T=2 h (2 hours after Radiesse® dermal filler injection). Between T=0 and T=2 h, the animals were under surveillance in a recovery room on a heating mat with fluidotherapy.

For the CT acquisitions at T=4 h, pigs received an IV (intravenous) injection of Propofol (1 mg/kg) and on Days 1, 3, 7 and 14, pigs received an IM injection of anesthesia (Zoletil (Tilétamine/Zolazépam—3.75 mg/kg) and Rompun (Xylazine—1.5 mg/kg)).

For each CT-scan, animals were positioned in dorsal recumbency (ventral images) and acquisitions were centered on the injection sites.

The parameters of the CT-scanners are described in the Table 13.

TABLE 13

CT acquisition parameters.

| Imaging system | Scanner BrightSpeed 16 |
|---|---|
| Image number | 1 acquisition (dorsal recumbency) at each timepoint centered on the injection sites |
| Image format | Dicom format (.dcm) |
| Field of View (FOV) | 35 cm |
| Axial resolution | 703 μm |
| Slice thickness | 625 μm (310 μm after reconstruction) |
| Rotation | 0.8 s |

TABLE 13-continued

CT acquisition parameters.

| Imaging system | Scanner BrightSpeed 16 |
|---|---|
| Pitch | 0.938 |
| Tension | 120 kV |
| Amperage | 150 mA |
| Algorithms for reconstruction | STANDARD & BONE |

Animal Euthanasia and Post-Mortem Examination

On Day 15, animals were euthanized under anesthesia (IM injection of Zoletil (Tiletamine/Zolazepam—3.75 mg/kg) and Rompun (Xylazine—1.5 mg/kg)) by an IV lethal injection of pentobarbital (0.45 ml/kg).

After euthanasia, each injection site was observed and then, an incision was performed in the skin, on the animal ventral area, to perform a macroscopic examination of each side (internal and external) of the injection site/nodule.

Injection Site Sampling and Fixation

After euthanasia on Day 15, an approximate size of 2×2 cm of each nodule, centered on the injection site, was sampled and was attached onto a piece of cork to prevent skin folding. One site of Radiesse® dermal filler injected on Day 15 and a number of 3 sites of un-injected skin (from pig PC01/1097-01) were also sampled and considered as positive and negative controls, respectively. Each nodule was orientated to facilitate cutting with the microtome (see, e.g., above). The orientation was noted on the skin and on the piece of cork. Then, each sample was fixed in formaldehyde solution 4% buffered at room temperature for 48 hours±2 h in an appropriate volume (5 at 10 times more than the volume of the sample). Then, the samples were transferred into Ethanol 70% (in an appropriate volume −5 at 10 times more than the volume of the sample) and were kept at room temperature. Finally, the samples were sent to LLS Rowiak LaserLabSolutions GmbH (Test Site n° 2) to embed the injection sites/nodules in MMA.

Embedding of Tissue in MMA and Sectioning

After the fixation step, samples were dehydrated in solutions with increasing alcohol concentrations, infiltrated and polymerized in MMA. Resulting blocks were cut following the orientation right-left, on area of interest with a diamond saw (Struers Secotom 15). Blocks were mounted on microscope slides (LLS Glue) and subsequently sections of approximately 10 µm (2 sections/sample) were prepared with lasermicrotome (TissueSurgeon, LLS ROWIAK LaserLabSolutions).

Staining

After deplastification, sections were subsequently stained in Hematoxylin Eosin (HE). After dehydration, sections were coverslipped with Roti® Histokitt (Carl Roth). Cytoplasm is stained pink and nuclei are stained violet/blue. Extracellular matrix is stained in yellow to pink.

Reference Volume Calculation

To calculate the reference volume of each injected test item (Radiesse® dermal filler and each hyperosmotic solution), the injected mass (expressed in grams) of each test items is calculated as following:

Reference mass(g) =

Syringe weight before injection(g) − Syringe weight after injection(g)

To convert the reference mass of the syringe (grams) into reference injected volume (µL), the following formula is applied (the density of each test item is mentioned above):

$$\text{Reference injected volume}(\mu l) = \frac{\text{Reference mass(g)}}{\text{Density}} \times 1000$$

Computed Tomography Acquisitions

The CT acquisitions are analyzed with the software Avizo version 9.2.0. The objective of this analysis was to assess the dispersion over time of the Radiesse® dermal filler injected by SC route after injection of different hyperosmotic solutions.

To achieve this goal, the evolution of these parameters is observed over time:
  the volume of each nodule (Radiesse® dermal filler and solution separately),
  the mean density of each nodule (Radiesse® dermal filler and solution separately),
  the 3D shape of each nodule by visualization of the 3D model of each nodule at each time point (Radiesse® dermal filler with or without solution separately).

Figure 10:
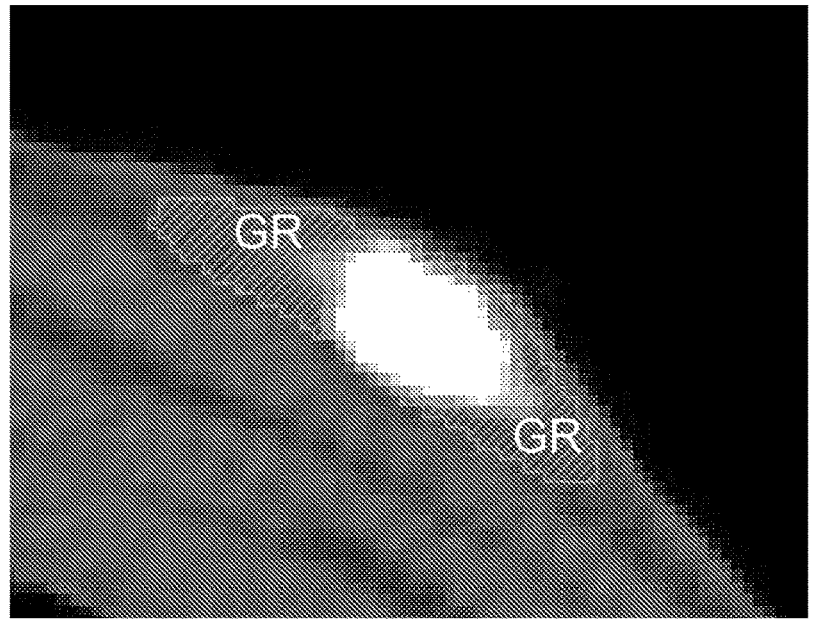
FIG. 10. Automatic segmentation with the thresholding procedure to select the voxels with a grey level between −100 and 250 HU (labelled GR) corresponding to the injected solution (Sodium Hydrogen Carbonate—P20WK-EE-04 at T+2 h).

Segmentation:

An image segmentation is performed on each CT acquisition on the STANDARD reconstruction. At first, a manual pre-segmentation is performed around each nodule in order to roughly isolate the voxels corresponding to Radiesse® dermal filler and hyperosmotic solutions and defined a Region of Interest (ROI). Secondly, an automatic segmentation is applied on the ROI previously defined using a global grey level thresholding procedure. The relevant threshold allowing the isolation of the pure (not dispersed) Radiesse® dermal filler or of the solutions (containing or not containing dispersed Radiesse® dermal filler) is defined on the basis of a Hounsfield Unit (HU) histogram, following the Otsu method to accurately define the ROI:

The relevant HU threshold for Radiesse® dermal filler, which is intrinsically radio-opaque, is determined at +250 HU. All the voxels having a grey level greater than 250 HU were selected in a ROI which corresponds to Pure (not dispersed) Radiesse® dermal filler throughout the study.
  For the other solutions, the relevant HU threshold is determined between −100 HU and +250 HU (determined in Example 3). Similarly, all the voxels having a grey level between these HU values are selected in a ROI and corresponds to the pure solution or solution containing some dispersed Radiesse® dermal filler (see, FIG. 10).

Figure 11:
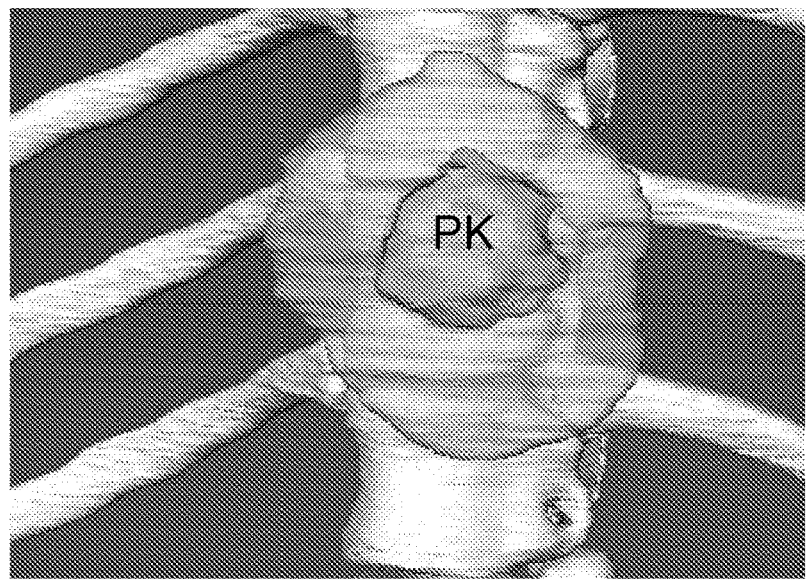
FIG. 11. 3D model of nodule of Radiesse® dermal filler labelled PK) with injected solution Sodium Hydrogen Carbonate (P20WK-EE-04) presented in 3D view at T+2 h.

Then, a 3D model of these selected voxels (see, FIG. 11) is obtained allowing the calculation of the total volume (in mm³) and the mean density (in HU) of the two defined compartments of each nodule of Pure Radiesse® dermal filler and of each solution containing or not containing dispersed Radiesse® dermal filler.

Quantification:

The volume (in mm³) of the ROI of Radiesse® dermal filler and the solutions corresponding to each nodule and the mean density (in HU) of each nodule are calculated at each time point. See Tables 15 and 16.

In order to assess the evolution over time of the dispersion and the behavior of dermal filler SC injected, the mean volume±standard deviation (SD) and the average of mean density±SD are calculated for each test item (of the two defined compartments) at each time point. A comparison between the mean volume and the average of the mean density evolution obtained for the Radiesse® dermal filler alone, considered as the control, and the combinations of the Radiesse® hyperosmotic solutions is performed (for the threshold [+250; +∞] HU).

In addition, the mean volume±SD and the average of the mean density±SD of each solution are compared with each other (for the threshold [−100; +250] HU).

The evolution of the mean volumes and the average of the mean densities of each test item for the threshold [+250; +∞] HU and [−100; +250] HU are represented in graphs.

Visualization

A 3D model of each nodule at each time point is presented to visualize the evolution of 3D shape of the test items and behavior of different solutions on Radiesse® filler nodules after injection (see, FIGS. 15-18).

Histological Analysis

The stained slides are observed with an optical microscope (Leica DM2000) combined with a digital camera (Leica DFC420C), managed with an imaging acquisition system (LAS V4.2).

The images (jpg format) are selected for the realization of photo-board performed using the software Photoshop (Adobe CC2019).

At first, a qualitative analysis of each slice to observe the eventual local inflammatory reaction (localization, intensity, inflammatory cell types) is performed. Moreover, the eventual tissue and cell necrosis, the remaining dermal filler presence and cell infiltration are observed.

Results and Discussion

On Day −3, each solution was prepared. Nothing abnormal was reported during the preparation.

On Day 0, the injection session of the test item P20WK-EE-01 (Radiesse® dermal filler) lasted about 10 minutes per pig. One hour±5 min after this injection, the injection session of the test item P20WK-EE-02 to P20WK-EE-05 into the Radiesse® filler nodule was performed and lasted about 5 minutes per pig. Nothing abnormal was reported during the injection sessions.

After the injection session of the hyperosmotic solutions (P20WK-EE-02 to P20WK-EE-05) at T=1 h 15, a redness on the nodule surface was observed for pigs PC01 to PC04 on all nodules (except nodules injected with Radiesse® dermal filler alone) which progressively disappeared by the end of the CT session at T=4 h.

No other abnormal clinical sign was observed on pigs during the injection sessions.

After the injection sessions, the mean of the injected volume of the nodules of Radiesse® dermal filler and the other solutions was relatively close to the targeted theoretical volume of 500 μl (504.4±9.9 μl) and 1500 μl (see, Table 14) respectively.

TABLE 14

Mean and SD of the injected volume of each solution (P20WK-EE-02 to P20WK-EE- 05).

| Mean and SD of the injected volume for each solution | Injected volume (in μl) |
|---|---|
| Mean - Magnesium Chloride Hexahydrate (P20WK-EE-02) | 1455.4 |
| SD - Magnesium Chloride Hexahydrate (P20WK-EE-02) | 8.2 |
| Mean - Fructose (P20WK-EE-03) | 1546.7 |
| SD - Fructose (P20WK-EE-03) | 22.9 |
| Mean - Sodium Hydrogen Carbonate (P20WK-EE-04) | 1371.1 |

TABLE 14-continued

Mean and SD of the injected volume of each solution (P20WK-EE-02 to P20WK-EE- 05).

| Mean and SD of the injected volume for each solution | Injected volume (in μl) |
|---|---|
| SD - Sodium Hydrogen Carbonate (P20WK-EE-04) | 22.6 |
| Mean - Trisodium Citrate Dihydrate (P20WK-EE-05) | 1424.2 |
| SD - Trisodium Citrate Dihydrate (P20WK-EE-05) | 6.8 |

Assessment of the Dermal Filler Short-Term Dispersion

Volume evolution of Pure Radiesse® dermal filler (not dispersed Radiesse® dermal filler) (>250 HU)

Figure 12A:
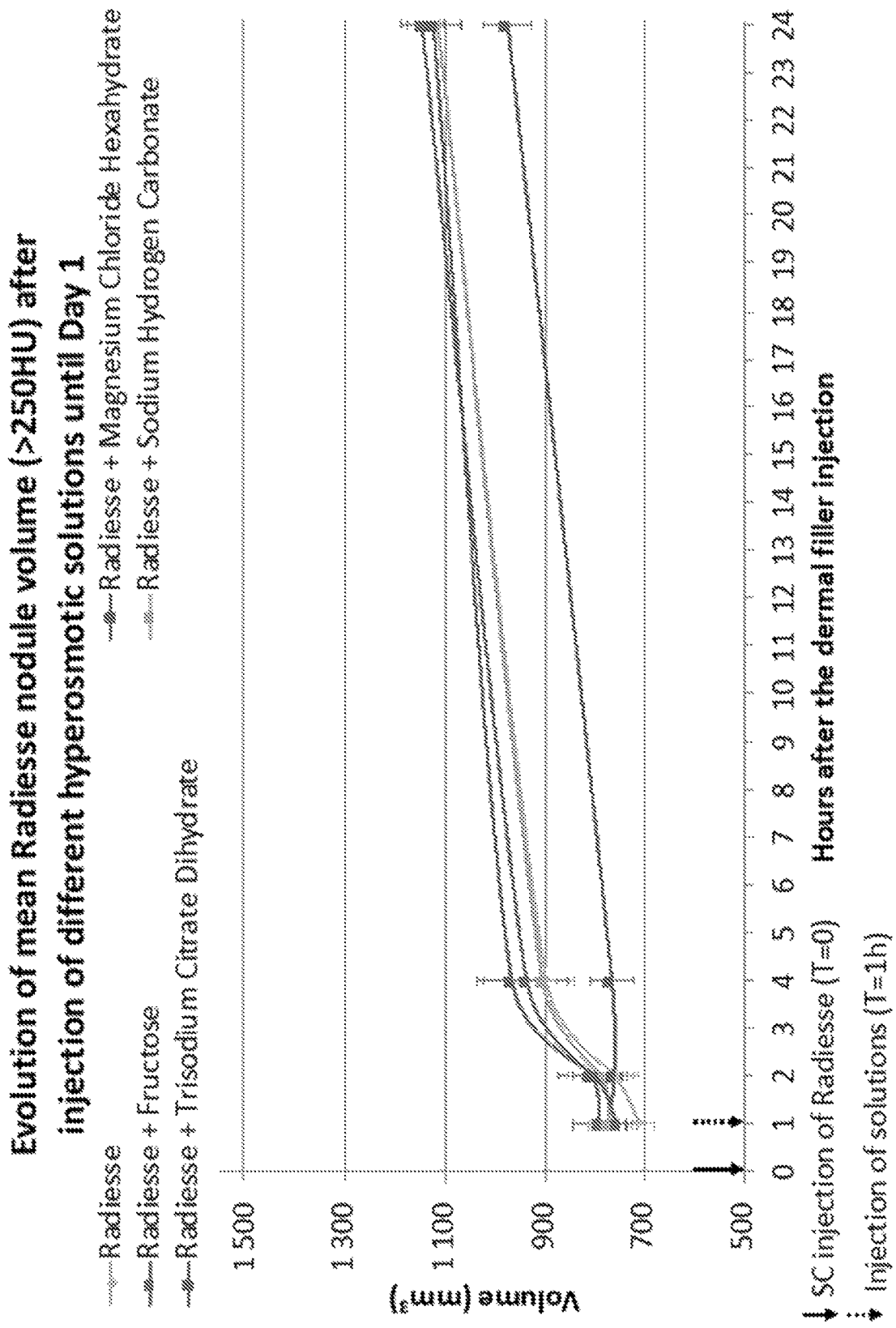
FIGS. 12A-12B. Mean nodule volumes (in mm$^3$)±SD of Radiesse® filler (pure Radiesse® filler >250 HU) measured at different timepoints from Day 0 (T0+1 h 15) (FIG. 12A) to Day 15 (FIG. 12B), after injection of different hyperosmotic solutions injected inside Radiesse® dermal filler.

About 1 hour and 15 min after the SC injection of Radiesse® dermal filler, the mean volume of Radiesse® filler nodules (alone) was at 711.3±29.4 mm$^3$ and the mean volume of Radiesse® filler nodules with injected hyperosmotic solutions was on average 773.2±43.5 mm$^3$ and were slightly increased compared to the targeted volume of 500 μL, injected at T0 (FIG. 12A). This slight difference between the mean volume of Radiesse® filler nodules (alone) and Radiesse® filler nodules+hyperosmotic solutions could be due to the injection of the solutions into the Radiesse® filler nodule.

Figure 12B:
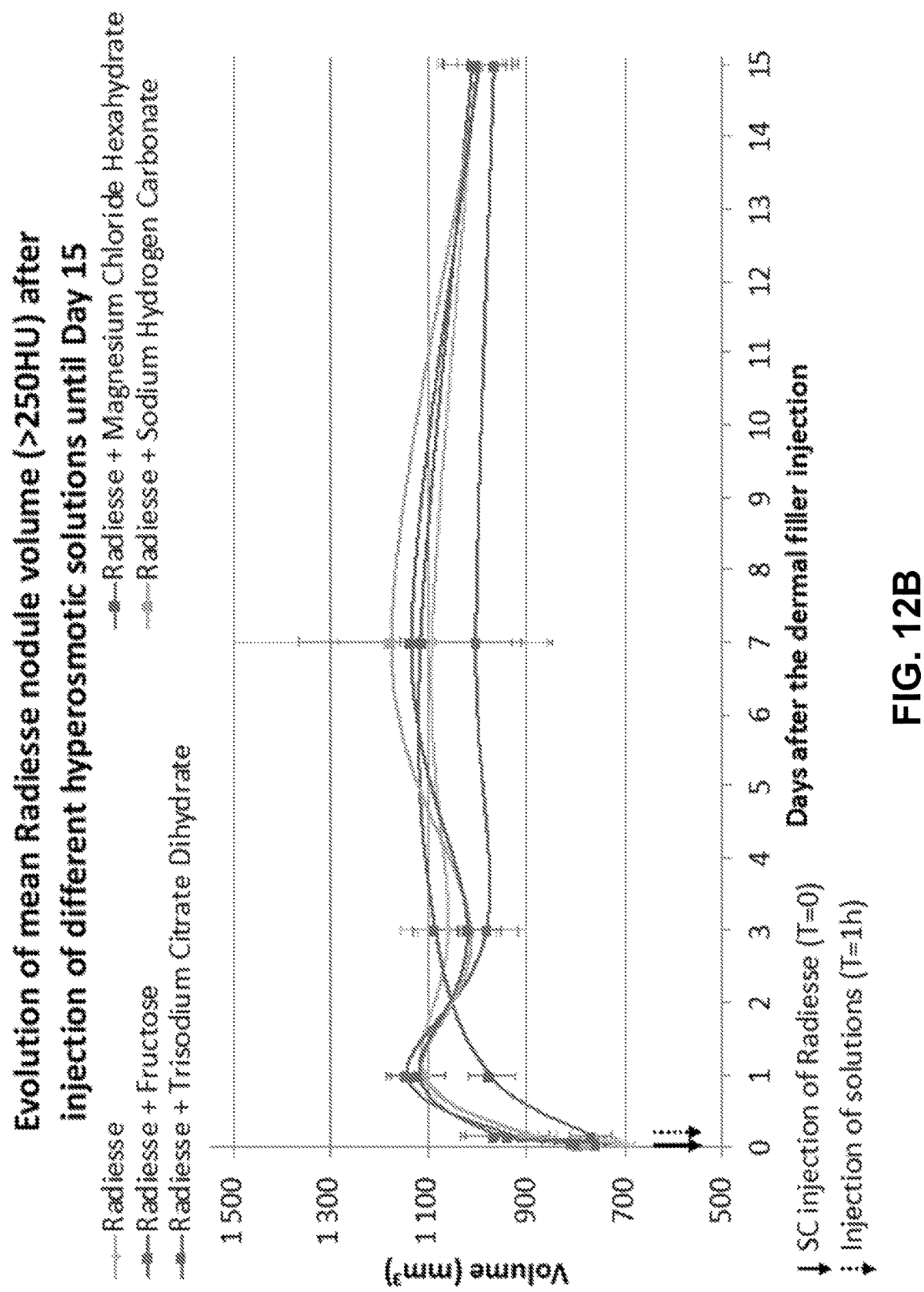

The mean volume of Radiesse® filler nodules without injected solutions increased from T0+2 h until Day 1 and reached 1112.2±46.0 mm$^3$. This expansion phase could be explained by the water tapping. Then, the mean volume of Radiesse® filler nodules (alone) remained stable until Day 7 and slightly decreased on Day 15. On Day 15 (see, FIG. 12B), the mean volume of Radiesse® filler nodules alone was 1003.4±79.7 mm$^3$, corresponding to a variation of 99.9% between T=0 (injected volume in mm$^3$) and Day 15 (CT volume measured).

The mean volume of Radiesse® filler nodules with each injected solution presented the same trend as the mean volume of Radiesse® filler nodules alone, except for the mean volume of Radiesse® filler nodules injected with Magnesium Chloride (P20WK-EE-02) which increased only from T0+24 h (remained stable between T0+1 h 15 and T0+4 h) and until Day 7.

On Day 15, the mean volumes of Radiesse® filler nodules irrespective of the injected solution were similar: between 966.8±52.9 (for the Fructose solution) and 1009.6±66.3 mm$^3$ (for the Magnesium Chloride solution injection).

Volume evolution of solutions with potential dispersed Radiesse® dermal filler (between −100 HU and 250 HU)

After injection at T0+1 h, the mean volume of the nodules injected with the Magnesium Chloride and Fructose solutions drastically increased between T=1 h 15 and T=4 h, whereas the mean volume of the nodules injected with the Sodium Hydrogen Carbonate and Trisodium Citrate solutions increased, but to a lesser extent between T=1 h 15 and T=2 h and then the mean volume of the nodules injected with each of the solutions decreased until Day 1:

The mean volume of nodules injected with Magnesium Chloride and Fructose solutions was at 5979.8±954.6 mm$^3$ and 7000.8±1389.9 mm$^3$, respectively, at T+4 h.

The mean volume of nodules injected with Sodium Hydrogen Carbonate and Trisodium Citrate solutions was at 2577.4±54.0 mm$^3$ and 4319.7±989.2 mm$^3$, respectively, at T=2 h.

Then, the mean volume of the nodules injected with each of the hyperosmotic solutions remained relatively stable on Day 15. Finally, the mean volume of all the hyperosmotic solutions (P20WK-EE-02 to P20WK-EE-05) reached between 883.9±269.9 mm$^3$ (for the Fructose solution) and 1352.3±570.6 mm$^3$ (for the Sodium Hydrogen Carbonate solution) on Day 15, corresponding to a variation of −42.8% and −1.4% respectively compared to the injected volume (in μL) on T=1 h.

Individual injected volume (in μL) of nodules of Radiesse® dermal filler SC injected in pigs PC01 to PC04 on Day 0.

The individual volumes of each nodule at each time point are presented in the Tables 17-18.

Mean Density Evolution of Nodules

Mean Density Evolution of Pure Radiesse® Dermal Filler (not Dispersed Radiesse® Dermal Filler) (>250 HU)

Figure 13A:
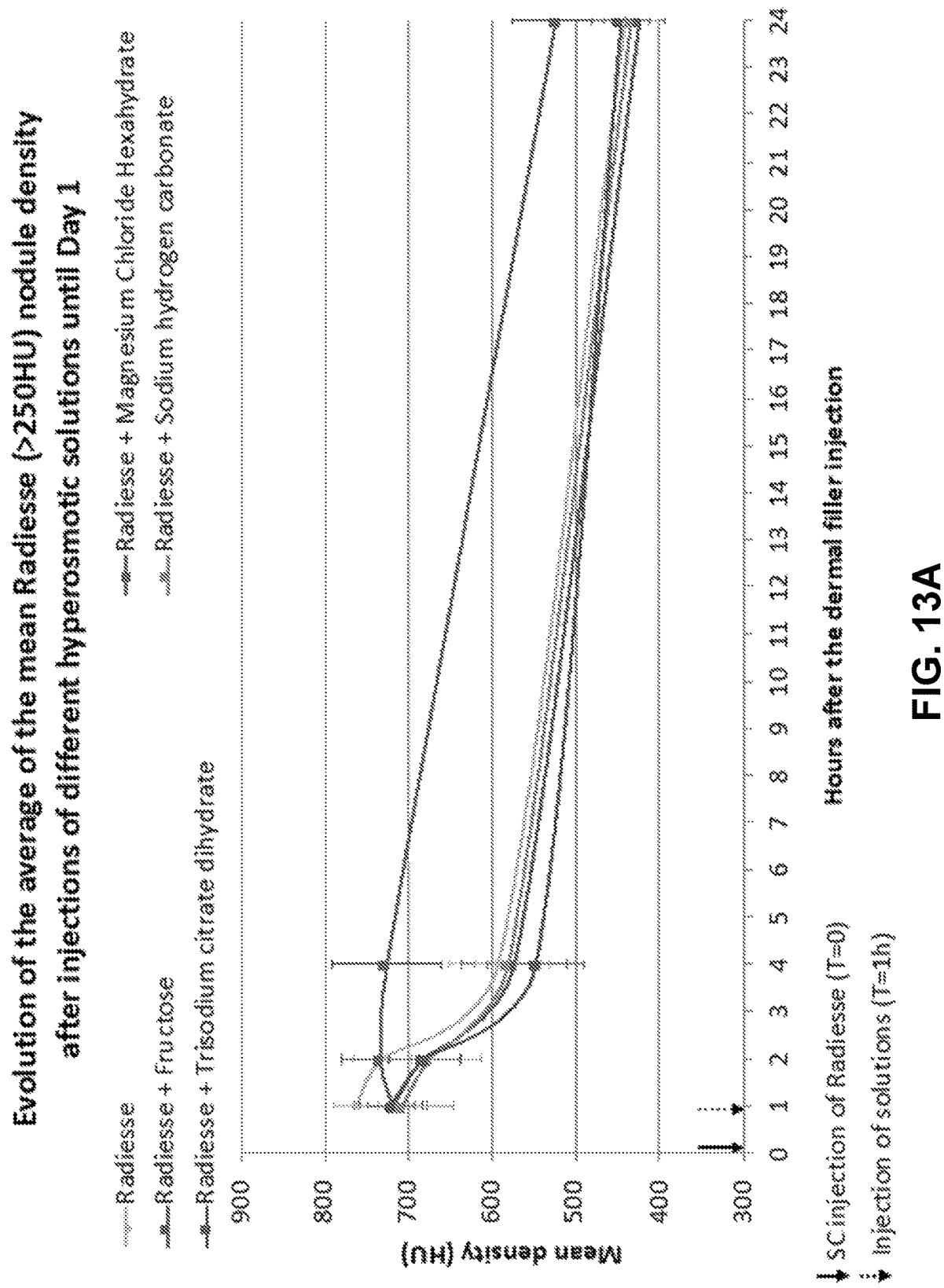
FIGS. 13A-13B. Average of the mean density (in HU)±SD of Radiesse® filler (pure Radiesse® filler >250 HU) nodules measured at different timepoint between Day 1 (FIG. 13A) and Day 15 (FIG. 13B), after injection of different hyperosmotic solutions injected inside Radiesse® dermal filler.
Figure 13B:
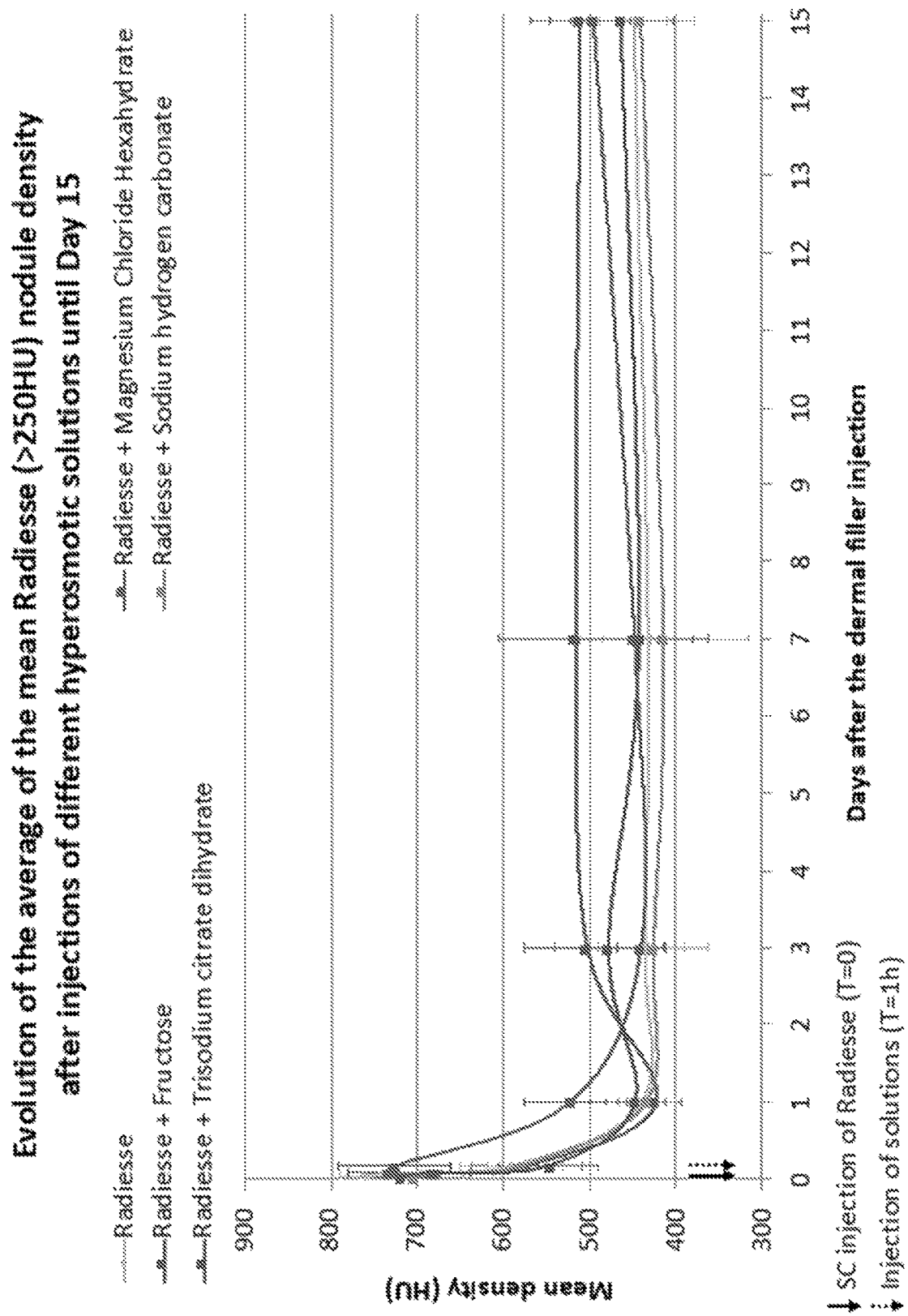

About 1 hour and 15 minutes after the SC injection, the average of the mean density of Radiesse® filler nodules alone was at 762.7±26.8 HU (see, FIG. 13A). Then, the average of the mean density of Radiesse® filler nodules alone decreased until Day 1 to reach 440.5±27.2 HU and then remained stable until Day 15 (end of the study) (450.0±39.2 HU) (see, FIG. 13B). This observation was consistent with the evolution of the volume of Radiesse® filler alone.

The average of the mean density of Radiesse® filler nodules with the different injected hyperosmotic solutions presented the same trend as those of Radiesse® filler nodules alone, except for the Radiesse® filler nodules injected with Magnesium Chloride solution. The mean average of density of Radiesse® filler nodule injected with Magnesium Chloride solution was stable until T+4 h, decreased until Day 3 and finally remained stable until Day 15.

The average of the mean density of Radiesse® filler nodules injected with Fructose solution and Radiesse® filler nodules injected with Trisodium Citrate solution slightly increased between Day 1 and Day 3 (424.6±31.6 HU and 447.0±34.1 HU on Day 1 and 505.0±72.2 HU and 478.2±64.8 HU on Day 3, respectively) and then, remained stable until Day 15.

Finally, the average of the mean density of Radiesse® filler nodules alone was 450.0±39.2 HU on Day 15. Similarly, the average of the mean densities of Radiesse® filler nodules injected with different solutions were between 441.3±62.9 HU (Sodium Hydrogen Carbonate solution) and 512.9±57.4 HU (Fructose solution).

Mean density evolution of solutions with potential dispersed Radiesse® dermal filler (between −100 HU and 250 HU)

After the injection at T=0+1 h, the average of the mean density of the nodules of the Magnesium Chloride and Fructose solutions drastically decreased between T=1 h 15 (44.3±9.5 and 58.6±6.2 respectively) and T=4 h (−6.7±5.3 HU and −1.0±7.7 HU respectively), whereas the average of the mean density of the nodules of the Sodium Hydrogen Carbonate and Trisodium Citrate solutions slightly decreased between T=1 h 15 (25.7±5.5 HU and 18.4±7.0 HU) and T=2 h (14.1±7.1 HU and 2.1±7.9 HU, respectively).

Then, the average of the mean density of nodules of the Sodium Hydrogen Carbonate and Trisodium Citrate solutions increased until Day 3 and after that, remained stable until Day 15, whereas the mean average of the nodules of Fructose and Magnesium Chloride slightly increased until Day 15.

Finally, the average of the mean density of solution nodules (P20WK-EE-02 to P20WK-EE-05) was similar (in average of 76.3±16.2 HU) at the end of the study (Day 15).

The variation of the average of the mean density of solutions was between 34.7% (for the Fructose solution) and 347.7% % (for the Trisodium Citrate Dihydrate solution) on Day 15 compared to the mean average of density measured on T=1 h 15.

The individual mean densities of each nodule at each time point are presented in Tables 19 and 20.

3D Shape Evolution

The 3D shape evolution is assessed by visualization of the 3D model of each nodule. In order to visualize the evolution over time of the 3D shape of nodules of Radiesse® dermal filler alone and those injected with different solutions, 3D models of each nodule from Day 0+1 h 15 to Day 15 is presented in FIGS. 15-18.

The shape of the nodule changed during the study and tended to appear with a flattened shape, mainly on Day 15 (end of the study). All the nodules were still visible until the end of the study.

The nodules of Radiesse® dermal filler presented an oval shape 1 h 15 after injection. In addition, the nodule shape of Radiesse® filler nodules changed over time and nodules appeared more flattened and became rougher until Day 15 (end of the study) and was slightly more visible in Radiesse® filler nodules injected with each solution compared to Radiesse® filler nodules without injection.

These observations may be explained by the solution injected tending to disperse the Radiesse® dermal filler.

Macroscopic Observations and Post-Mortem Examination

Nodules were macroscopically visible throughout the study and the majority of them presented a flatted shape on Day 15. No observations were noted during the post-mortem examination.

The CT-scanner analyses showed that the volume of Radiesse® dermal filler expands from the injection until Day 1. After this expansion phase, the volume of the Radiesse® filler nodule remains relatively stable until Day 15 and corresponding to a variation of almost 100% on Day 15 compared to the injected volume at T=0. Conversely, the mean density of Radiesse® filler nodules decreases from T0+1 h 15 until Day 3 and then, remains relatively stable until Day 15 and is consistent with the volume evolution. The decrease of density observed is consistent with a change in water content (water tapping) and it is possible to correlate this observation with the increase of volume of Radiesse® filler nodules.

In summary, when Magnesium Chloride solution is injected into a Radiesse® dermal filler nodule, the volume of nodule increases more slowly than without injection of solution and the mean density decreases more slowly than without injection of solutions, indicating that solution could slow down the water tapping. However, on Day 15, irrespectively of the solution injected, volume and mean density of Radiesse® filler nodules without injected solution is similar to those of Radiesse® filler nodules with injected solutions. In addition, 3D models showed that the Radiesse® dermal filler is slightly rougher and more split after injection of solutions than without injection of solutions.

A difference is observed for the mean volume of the Magnesium Chloride and Fructose solutions which increased until T=4 h compared to the Hydrogen Carbonate and Trisodium Citrate Hydrogen solutions which increased until T=2 h and the mean average density of these solutions decreased until T=4 h or T=2 h, respectively.

Thus, the CT-scanner results show that the Radiesse® filler with or without injection of different hyperosmotic solutions had an expansion phase between Day 0 and Day 1 and when Magnesium Chloride solution is injected, the volume increases slower than without solution. This observation is likely consistent with the solution action which tends to slow down the water tapping of the Radiesse® dermal filler.

Scientific and Technical References:
- N. Otsu. A threshold selection method from gray-level histograms. *IEEE Transactions on systems, man and cybernetics* (1979) 9:62-66.
- Halimi, Célia, et al. "Chitosan solutions as injectable systems for dermal filler applications: Rheological characterization and biological evidence." 2015 37th Annual International Conference of the IEEE Engineering in Medicine and Biology Society (EMBC). IEEE, 2015.

Individual values of injected volume of test items.

TABLE 15

Individual injected volume (in µL) of nodules of Radiesse ® dermal filler SC injected in pigs PC01 to PC04 on Day 0.

| No Pig | No Tattoo | Theoretical volume (µl) | Injected product | Nodule | Injected mass (g) | Injected volume (µl) |
|---|---|---|---|---|---|---|
| PC01 | 1097-01 | 500.00 | Radiesse ® | 5 | 0.81 | 490.2 |
| PC01 | 1097-01 | | dermal filler | 10 | 0.84 | 506.3 |
| PC02 | 1097-02 | | | 1 | 0.84 | 506.1 |
| PC02 | 1097-02 | | | 6 | 0.84 | 507.2 |
| PC03 | 1097-03 | | | 2 | 0.83 | 505.4 |
| PC03 | 1097-03 | | | 7 | 0.85 | 516.8 |
| PC04 | 1097-04 | | | 3 | 0.80 | 487.8 |
| PC04 | 1097-04 | | | 8 | 0.82 | 497.0 |
| PC01 | 1097-01 | | | 1 | 0.80 | 487.2 |
| PC01 | 1097-01 | | | 6 | 0.84 | 512.1 |
| PC02 | 1097-02 | | | 2 | 0.84 | 509.2 |
| PC02 | 1097-02 | | | 7 | 0.85 | 516.6 |
| PC03 | 1097-03 | | | 3 | 0.83 | 505.8 |
| PC03 | 1097-03 | | | 8 | 0.86 | 522.8 |
| PC04 | 1097-04 | | | 4 | 0.83 | 505.0 |
| PC04 | 1097-04 | | | 9 | 0.83 | 501.9 |
| PC01 | 1097-01 | | | 2 | 0.79 | 479.4 |
| PC01 | 1097-01 | | | 7 | 0.82 | 499.7 |
| PC02 | 1097-02 | | | 3 | 0.83 | 500.2 |
| PC02 | 1097-02 | | | 8 | 0.86 | 521.0 |
| PC03 | 1097-03 | | | 4 | 0.82 | 499.1 |
| PC03 | 1097-03 | | | 9 | 0.84 | 509.8 |
| PC04 | 1097-04 | | | 5 | 0.83 | 502.0 |
| PC04 | 1097-04 | | | 10 | 0.82 | 496.1 |
| PC01 | 1097-01 | | | 3 | 0.82 | 494.2 |
| PC01 | 1097-01 | | | 8 | 0.83 | 505.3 |
| PC02 | 1097-02 | | | 4 | 0.83 | 501.3 |
| PC02 | 1097-02 | | | 9 | 0.82 | 495.8 |
| PC03 | 1097-03 | | | 5 | 0.84 | 507.4 |
| PC03 | 1097-03 | | | 10 | 0.83 | 505.9 |
| PC04 | 1097-04 | | | 1 | 0.85 | 512.4 |
| PC04 | 1097-04 | | | 6 | 0.83 | 505.9 |
| PC01 | 1097-01 | | | 4 | 0.84 | 506.9 |
| PC01 | 1097-01 | | | 9 | 0.87 | 528.7 |
| PC02 | 1097-02 | | | 5 | 0.84 | 508.8 |
| PC02 | 1097-02 | | | 10 | 0.82 | 494.5 |
| PC03 | 1097-03 | | | 1 | 0.83 | 500.2 |
| PC03 | 1097-03 | | | 6 | 0.83 | 502.4 |
| PC04 | 1097-04 | | | 2 | 0.84 | 507.0 |
| PC04 | 1097-04 | | | 7 | 0.85 | 516.4 |
| Mean - Radiesse ® filler [+250; +∞] HU | | | | | 0.83 | 504.4 |
| SD - Radiesse ® filler [+250; + ∞] HU | | | | | 0.02 | 9.9 |

TABLE 16

Individual injected volume (in µL) of solutions (P20WK-EE-02 to P20WK-EE-05) injected inside Radiesse ® dermal filler nodules on pigs PC01 to PC04 on Day 0.

| No Pig | No Tattoo | Theoretical volume (µl) | Injected product | Nodule | Injected mass (g) | Injected volume (µl) |
|---|---|---|---|---|---|---|
| PC01 | 1097-01 | 1500.0 | Magnesium | 1 | 1.63 | 1471.2 |
| PC01 | 1097-01 | | Chloride | 6 | 1.62 | 1461.5 |
| PC02 | 1097-02 | | Hexahydrate | 2 | 1.61 | 1452.2 |
| PC02 | 1097-02 | | | 7 | 1.61 | 1453.4 |
| PC03 | 1097-03 | | | 3 | 1.62 | 1460.0 |
| PC03 | 1097-03 | | | 8 | 1.61 | 1447.5 |
| PC04 | 1097-04 | | | 4 | 1.61 | 1450.1 |

TABLE 16-continued

Individual injected volume (in μL) of solutions (P20WK-EE-02 to P20WK-EE-05) injected inside Radiesse ® dermal filler nodules on pigs PC01 to PC04 on Day 0.

| No Pig | No Tattoo | Theoretical volume (μl) | Injected product | Nodule | Injected mass (g) | Injected volume (μl) |
|---|---|---|---|---|---|---|
| PC04 | 1097-04 | | | 9 | 1.61 | 1447.6 |
| Mean - Magnesium Chloride Hexahydrate [−100; +250] HU | | | | | 1.62 | 1455.4 |
| SD - Magnesium Chloride Hexahydrate [−100; +250] HU | | | | | 0.01 | 8.2 |
| PC01 | 1097-01 | 1500.0 | Fructose | 2 | 1.73 | 1561.3 |
| PC01 | 1097-01 | | | 7 | 1.77 | 1592.9 |
| PC02 | 1097-02 | | | 3 | 1.70 | 1535.7 |
| PC02 | 1097-02 | | | 8 | 1.70 | 1535.1 |
| PC03 | 1097-03 | | | 4 | 1.72 | 1545.2 |
| PC03 | 1097-03 | | | 9 | 1.72 | 1549.9 |
| PC04 | 1097-04 | | | 5 | 1.71 | 1538.8 |
| PC04 | 1097-04 | | | 10 | 1.68 | 1515.0 |
| Mean - Fructose [−100; +250] HU | | | | | 1.72 | 1546.7 |
| SD - Fructose [−100; +250] HU | | | | | 0.03 | 22.9 |
| PC01 | 1097-01 | 1500.0 | Sodium | 3 | 1.53 | 1377.5 |
| PC01 | 1097-01 | | Hydrogen | 8 | 1.57 | 1417.0 |
| PC02 | 1097-02 | | Carbonate | 4 | 1.54 | 1383.6 |
| PC02 | 1097-02 | | | 9 | 1.51 | 1363.1 |
| PC03 | 1097-03 | | | 5 | 1.52 | 1371.4 |
| PC03 | 1097-03 | | | 10 | 1.49 | 1345.3 |
| PC04 | 1097-04 | | | 1 | 1.50 | 1350.5 |
| PC04 | 1097-04 | | | 6 | 1.51 | 1360.4 |
| Mean - Sodium Hydrogen Carbonate [−100; +250] HU | | | | | 1.52 | 1371.1 |
| SD - Sodium Hydrogen Carbonate [−100; +250] HU | | | | | 0.03 | 22.6 |
| PC01 | 1097-01 | 1500.0 | Trisodium | 4 | 1.57 | 1415.0 |
| PC01 | 1097-01 | | Citrate | 9 | 1.59 | 1431.4 |
| PC02 | 1097-02 | | Dihydrate | 5 | 1.58 | 1421.5 |
| PC02 | 1097-02 | | | 10 | 1.58 | 1425.2 |
| PC03 | 1097-03 | | | 1 | 1.57 | 1417.7 |
| PC03 | 1097-03 | | | 6 | 1.58 | 1419.6 |
| PC04 | 1097-04 | | | 2 | 1.59 | 1430.5 |
| PC04 | 1097-04 | | | 7 | 1.59 | 1432.6 |
| Mean - Trisodium Citrate Dihydrate [−100; +250] HU | | | | | 1.58 | 1424.2 |
| SD - Trisodium Citrate Dihydrate [−100; +250] HU | | | | | 0.01 | 6.8 |

TABLE 17

Individual volume (in mm$^3$) of nodules of Radiesse ® filler alone and Radiesse ® filler + Magnesium Chloride solution and Radiesse ® filler + Fructose solution SC injected on pigs PC01 to PC04 from Day 0 to Day 15.

| | | | | | Nodule volume (mm$^3$) | | | | | | |
|---|---|---|---|---|---|---|---|---|---|---|---|
| No Pig | No Tattoo | Theoretical volume (μl) | Injected product | Nodule | Day 0 + 1 h 15 | Day 0 + 2 h | Day 0 + 4 h | Day 1 | Day 3 | Day 7 | Day 15 |
| PC01 | 1097-01 | 500.0 | Radiesse | 5 | 745.8 | 792.1 | 928.7 | 1150.8 | 879.5 | 868.6 | 893.7 |
| PC01 | 1097-01 | | | 10 | 664.1 | 726.9 | 932.5 | 1157.6 | 1220.8 | 1149.8 | 1076.3 |
| PC02 | 1097-02 | | | 1 | 711.6 | 778.2 | 948.9 | 1151.7 | 1111.7 | 1374.8 | 1054.6 |
| PC02 | 1097-02 | | | 6 | 689.4 | 751.3 | 902.2 | 1140.9 | 1130.4 | 1369.1 | 1135.0 |
| PC03 | 1097-03 | | | 2 | 753.4 | 840.2 | 934.4 | 1056.5 | 1054.5 | 1043.9 | 938.1 |
| PC03 | 1097-03 | | | 7 | 720.3 | 705.5 | 629.2 | 1081.1 | 1074.3 | 1078.5 | 994.5 |
| PC04 | 1097-04 | | | 3 | 712.6 | 747.2 | 913.7 | 1115.9 | 1001.3 | 925.5 | 957.0 |
| PC04 | 1097-04 | | | 8 | 693.6 | 726.5 | 783.1 | 1043.2 | 1019.1 | 944.8 | 978.1 |
| Mean - Radiesse [+250; +∞] HU | | | | | 711.3 | 758.5 | 896.6 | 1112.2 | 1061.4 | 1094.4 | 1003.4 |
| SD - Radiesse [+250; +∞] HU | | | | | 29.4 | 43.4 | 58.8 | 46.0 | 101.0 | 193.4 | 79.7 |
| PC01 | 1097-01 | 500.0 | Radiesse + | 1 | 793.7 | 773.1 | 807.5 | 958.6 | 1052.6 | 1052.1 | 1006.5 |
| PC01 | 1097-01 | | Magnesium | 6 | 785.9 | 767.5 | 781.4 | 879.6 | 1052.3 | 1103.3 | 1062.3 |
| PC02 | 1097-02 | | Chloride | 2 | 737.9 | 737.7 | 737.8 | 998.0 | 1157.5 | 1409.5 | 1109.4 |
| PC02 | 1097-02 | | Hexahydrate | 7 | 741.6 | 733.0 | 741.0 | 1032.5 | 1046.1 | 1396.5 | 1055.9 |
| PC03 | 1097-03 | | | 3 | 799.8 | 775.7 | 794.7 | 1010.4 | 1024.3 | 956.4 | 949.3 |
| PC03 | 1097-03 | | | 8 | 850.1 | 813.1 | 792.8 | 986.8 | 1125.7 | 1053.9 | 1018.2 |
| PC04 | 1097-04 | | | 4 | 747.4 | 767.5 | 794.0 | 987.1 | 1119.5 | 1018.7 | 967.7 |
| PC04 | 1097-04 | | | 9 | 743.0 | 728.8 | 682.2 | 940.5 | 1106.8 | 937.0 | 907.6 |
| Mean - Radiesse + Magnesium Chloride hexahydrate [+250; +∞] HU | | | | | 774.9 | 762.1 | 766.4 | 974.2 | 1085.6 | 1115.9 | 1009.6 |
| SD - Radiesse + Magnesium Chloride hexahydrate [+250; +∞] HU | | | | | 39.6 | 28.1 | 42.7 | 47.7 | 47.6 | 185.1 | 66.3 |
| PC01 | 1097-01 | 500.0 | Radiesse + | 2 | 799.1 | 795.9 | 1039.3 | 1168.2 | 1043.6 | 1041.9 | 997.7 |
| PC01 | 1097-01 | | Fructose | 7 | 845.1 | 856.3 | 957.8 | 1120.2 | 1039.7 | 1040.7 | 997.2 |
| PC02 | 1097-02 | | | 3 | 739.4 | 750.5 | 861.1 | 1122.3 | 961.0 | 1239.0 | 944.9 |
| PC02 | 1097-02 | | | 8 | 852.5 | 863.0 | 985.4 | 1226.3 | 1053.3 | 1200.9 | 1054.8 |

TABLE 17-continued

Individual volume (in mm³) of nodules of Radiesse ® filler alone and Radiesse ® filler +
Magnesium Chloride solution and Radiesse ® filler + Fructose solution SC injected on pigs PC01 to PC04 from Day 0 to Day 15.

| No Pig | No Tattoo | Theoretical volume (µl) | Injected product | Nodule | Day 0 + 1 h 15 | Day 0 + 2 h | Day 0 + 4 h | Day 1 | Day 3 | Day 7 | Day 15 |
|---|---|---|---|---|---|---|---|---|---|---|---|
| PC03 | 1097-03 | | | 4 | 760.4 | 770.1 | 902.9 | 1085.5 | 969.6 | 879.3 | 923.5 |
| PC03 | 1097-03 | | | 9 | 837.5 | 898.7 | 1039.4 | 1165.0 | 992.2 | 953.1 | 997.7 |
| PC04 | 1097-04 | | | 5 | 793.0 | 808.3 | 912.1 | 1153.8 | 891.2 | 833.5 | 912.9 |
| PC04 | 1097-04 | | | 10 | 710.6 | 712.1 | 796.2 | 1115.5 | 897.7 | 838.3 | 905.4 |
| Mean - Radiesse + Fructose [+250; +∞] HU | | | | | 792.2 | 806.9 | 936.8 | 1144.6 | 981.0 | 1003.3 | 966.8 |
| SD - Radiesse + Fructose [+250; +∞] HU | | | | | 52.1 | 62.8 | 85.4 | 43.4 | 63.5 | 156.5 | 52.9 |

TABLE 18

Individual volume (in mm³) of nodules of Radiesse ® filler + Sodium Hydrogen Carbonate
solution and Radiesse ® filler + Trisodium Citrate solution SC injected on pigs PC01 to PC04 from Day 0 to Day 15.

| No Pig | No Tattoo | Theoretical volume (µl) | Injected product | Nodule | Day 0 + 1 h15 | Day 0 + 2 h | Day 0 + 4 h | Day 1 | Day 3 | Day 7 | Day 15 |
|---|---|---|---|---|---|---|---|---|---|---|---|
| PC01 | 1097-01 | 500.0 | Radiesse + | 3 | 865.6 | 885.8 | 958.4 | 1067.6 | 1099.5 | 1051.9 | 1038.4 |
| PC01 | 1097-01 | | Sodium | 8 | 751.3 | 788.6 | 892.6 | 1058.4 | 1107.8 | 1154.7 | 1026.2 |
| PC02 | 1097-02 | | Hydrogen | 4 | 759.4 | 674.9 | 932.5 | 1106.3 | 823.3 | 1642.0 | 1044.5 |
| PC02 | 1097-02 | | Carbonate | 9 | 755.2 | 747.9 | 910.8 | 1122.4 | 876.0 | 1721.7 | 905.1 |
| PC03 | 1097-03 | | | 5 | 734.7 | 768.8 | 900.6 | 1078.8 | 1033.2 | | 996.9 |
| PC03 | 1097-03 | | | 10 | 777.9 | 820.1 | 887.9 | 1118.3 | 1100.1 | 1038.8 | 1019.8 |
| PC04 | 1097-04 | | | 1 | 772.7 | 847.0 | 860.5 | 1126.9 | 1049.5 | 921.6 | 982.5 |
| PC04 | 1097-04 | | | 6 | 741.3 | 754.9 | 900.5 | 1201.8 | 981.4 | 863.1 | 949.9 |
| Mean - Radiesse + Sodium Hydrogen Carbonate [+250; +∞] HU | | | | | 769.8 | 786.0 | 905.5 | 1114.9 | 1014.5 | 1178.4 | 995.4 |
| SD - Radiesse + Sodium Hydrogen Carbonate [+250; +∞] HU | | | | | 41.3 | 65.4 | 29.5 | 43.5 | 110.5 | 323.5 | 48.1 |
| PC01 | 1097-01 | 500.0 | Radiesse + | 4 | 824.3 | 892.6 | 1068.4 | 1081.8 | 1106.6 | 1051.1 | 1053.5 |
| PC01 | 1097-01 | | Trisodium | 9 | 755.6 | 801.4 | 964.6 | 1038.5 | 1035.3 | 1062.1 | 926.7 |
| PC02 | 1097-02 | | Citrate | 5 | 735.4 | 796.2 | 884.8 | 1221.3 | 1066.5 | 1443.3 | 1113.3 |
| PC02 | 1097-02 | | Dihydrate | 10 | 707.7 | 765.5 | 946.5 | 1094.0 | 1057.1 | 1537.3 | 1075.6 |
| PC03 | 1097-03 | | | 1 | 753.9 | 789.2 | 1006.9 | 1128.5 | 1005.2 | 1037.2 | 938.9 |
| PC03 | 1097-03 | | | 6 | 788.2 | 829.8 | 1038.0 | 1160.8 | 1037.2 | 1106.47 | 994.2 |
| PC04 | 1097-04 | | | 2 | 705.6 | 743.4 | 876.3 | 1111.1 | 877.6 | 900.6 | 934.8 |
| PC04 | 1097-04 | | | 7 | 777.5 | 765.9 | 936.8 | 1139.5 | 982.3 | 962.3 | 958.0 |
| Mean - Radiesse + Trisodium Citrate Dihydrate [+250; +∞] HU | | | | | 756.0 | 798.0 | 965.3 | 1122.0 | 1021.0 | 1137.6 | 999.4 |
| SD - Radiesse + Trisodium Citrate Dihydrate [+250; +∞] HU | | | | | 40.5 | 46.5 | 68.9 | 55.0 | 69.2 | 228.1 | 72.3 |

TABLE 19

Individual mean density (in HU) of nodules of Radiesse ® dermal filler SC injected and with Magnesium Chloride
hexahydrate and Fructose solutions injected inside Radiesse ® filler nodules on pigs PC01 to PC04 from Day 0 to Day 15

| No Pig | No Tattoo | Theoretical volume (µl) | Product | Nodule | Day 0 + 1 h 15 | Day 0 + 2 h | Day 0 + 4 h | Day 1 | Day 3 | Day 7 | Day 15 |
|---|---|---|---|---|---|---|---|---|---|---|---|
| PC01 | 1097-01 | 500.0 | Radiesse | 5 | 761.2 | 695.4 | 503.6 | 393.0 | 368.9 | 365.4 | 391.4 |
| PC01 | 1097-01 | | | 10 | 808.7 | 763.8 | 590.5 | 424.5 | 397.1 | 424.1 | 442.2 |
| PC02 | 1097-02 | | | 1 | 733.7 | 737.3 | 552.9 | 428.0 | 398.2 | 380.0 | 416.8 |
| PC02 | 1097-02 | | | 6 | 769.4 | 758.5 | 623.6 | 456.2 | 450.2 | 411.0 | 437.2 |
| PC03 | 1097-03 | | | 2 | 725.3 | 665.6 | 552.6 | 437.7 | 442.4 | 432.8 | 453.6 |
| PC03 | 1097-03 | | | 7 | 777.9 | 746.2 | 649.4 | 464.0 | 453.8 | 438.7 | 450.2 |
| PC04 | 1097-04 | | | 3 | 748.5 | 730.7 | 576.5 | 438.7 | 497.5 | 501.8 | 511.4 |
| PC04 | 1097-04 | | | 8 | 777.1 | 753.8 | 690.8 | 481.6 | 489.3 | 512.6 | 497.0 |
| Mean - Radiesse [+250; +∞] HU | | | | | 762.7 | 731.4 | 592.5 | 440.5 | 437.2 | 433.3 | 450.0 |
| SD - Radiesse [+250; +∞] HU | | | | | 26.8 | 34.1 | 60.0 | 27.2 | 45.7 | 52.2 | 39.2 |
| PC01 | 1097-01 | 500.0 | Radiesse + | 1 | 662.4 | 659.8 | 608.2 | 458.4 | 427.4 | 389.5 | 470.6 |
| PC01 | 1097-01 | | Magnesium | 6 | 757.7 | 754.2 | 726.2 | 606.5 | 484.9 | 420.2 | 467.4 |
| PC02 | 1097-02 | | Chloride | 2 | 738.9 | 790.9 | 782.4 | 515.9 | 433.6 | 402.4 | 478.6 |
| PC02 | 1097-02 | | Hexahydrate | 7 | 747.4 | 770.9 | 770.0 | 458.3 | 406.2 | 381.1 | 456.3 |

TABLE 19-continued

Individual mean density (in HU) of nodules of Radiesse ® dermal filler SC injected and with Magnesium Chloride hexahydrate and Fructose solutions injected inside Radiesse ® filler nodules on pigs PC01 to PC04 from Day 0 to Day 15

| | | | | | Mean nodule density (HU) | | | | | | |
|---|---|---|---|---|---|---|---|---|---|---|---|
| No Pig | No Tattoo | Theoretical volume (µl) | Product | Nodule | Day 0 + 1 h 15 | Day 0 + 2 h | Day 0 + 4 h | Day 1 | Day 3 | Day 7 | Day 15 |
| PC03 | 1097-03 | | | 3 | 676.7 | 685.5 | 670.9 | 488.1 | 415.9 | 435.5 | 448.2 |
| PC03 | 1097-03 | | | 8 | 693.3 | 710.3 | 722.6 | 538.2 | 466.4 | 488.9 | 501.2 |
| PC04 | 1097-04 | | | 4 | 731.8 | 739.2 | 721.7 | 546.0 | 435.2 | 501.6 | 555.6 |
| PC04 | 1097-04 | | | 9 | 759.1 | 769.5 | 816.1 | 571.9 | 462.7 | 572.8 | 591.5 |
| Mean - Radiesse + Magnesium Chloride hexahydrate [+250; +∞] HU | | | | | 720.9 | 735.0 | 727.3 | 522.9 | 441.5 | 449.0 | 496.2 |
| SD - Radiesse + Magnesium Chloride hexahydrate [+250; +∞] HU | | | | | 38.0 | 45.8 | 65.6 | 53.1 | 27.1 | 66.6 | 51.1 |
| PC01 | 1097-01 | 500.0 | Radiesse + | 2 | 690.2 | 660.1 | 518.7 | 399.5 | 436.5 | 453.3 | 494.7 |
| PC01 | 1097-01 | | Fructose | 7 | 678.7 | 629.8 | 548.0 | 452.8 | 440.7 | 456.4 | 470.5 |
| PC02 | 1097-02 | | | 3 | 751.3 | 717.6 | 615.3 | 403.8 | 443.5 | 416.2 | 454.5 |
| PC02 | 1097-02 | | | 8 | 711.5 | 671.1 | 583.0 | 425.8 | 520.1 | 490.0 | 501.9 |
| PC03 | 1097-03 | | | 4 | 735.2 | 690.0 | 532.2 | 413.4 | 491.5 | 529.2 | 506.3 |
| PC03 | 1097-03 | | | 9 | 658.9 | 640.3 | 494.5 | 377.5 | 483.1 | 497.5 | 472.2 |
| PC04 | 1097-04 | | | 5 | 753.7 | 689.6 | 608.3 | 459.7 | 616.4 | 648.2 | 599.7 |
| PC04 | 1097-04 | | | 10 | 777.6 | 763.5 | 692.8 | 464.0 | 607.8 | 652.2 | 603.2 |
| Mean - Radiesse + Fructose [+250; +∞] HU | | | | | 719.7 | 682.7 | 574.1 | 424.6 | 505.0 | 517.9 | 512.9 |
| SD - Radiesse + Fructose [+250; + +∞] HU | | | | | 41.5 | 43.2 | 64.2 | 31.6 | 72.2 | 88.4 | 57.4 |

TABLE 20

Individual mean density (in HU) of nodules of Radiesse ® dermal filler SC injected and with Sodium hydrogen carbonate and Trisodium Citrate solutions injected inside Radiesse ® filler nodules on pigs PC01 to PC04 from Day 0 to Day 15.

| | | | | | Mean nodule density (HU) | | | | | | |
|---|---|---|---|---|---|---|---|---|---|---|---|
| No Pig | No Tattoo | Theoretical volume (µl) | Product | Nodule | Day 0 + 1 h 15 | Day 0 + 2 h | Day 0 + 4 h | Day 1 | Day 3 | Day 7 | Day 15 |
| PC01 | 1097-01 | 500.0 | Radiesse + | 3 | 580.3 | 568.8 | 513.7 | 437.4 | 386.7 | 352.1 | 410.1 |
| PC01 | 1097-01 | | Sodium | 8 | 730.6 | 699.3 | 596.2 | 463.4 | 440.1 | 400.9 | 452.3 |
| PC02 | 1097-02 | | Hydrogen | 4 | 680.6 | 635.8 | 551.1 | 387.6 | 362.1 | 314.4 | 381.4 |
| PC02 | 1097-02 | | Carbonate | 9 | 725.6 | 613.6 | 578.8 | 386.0 | 345.8 | 283.7 | 349.1 |
| PC03 | 1097-03 | | | 5 | 696.3 | 695.2 | 556.1 | 416.4 | 415.9 | 414.7 | 432.7 |
| PC03 | 1097-03 | | | 10 | 722.0 | 715.3 | 607.1 | 453.6 | 434.1 | 464.6 | 456.7 |
| PC04 | 1097-04 | | | 1 | 739.4 | 718.4 | 627.7 | 475.0 | 487.7 | 515.9 | 508.4 |
| PC04 | 1097-04 | | | 6 | 777.8 | 754.1 | 616.0 | 458.2 | 541.2 | 574.7 | 539.8 |
| Mean - Radiesse + Sodium hydrogen carbonate [+250; +∞] HU | | | | | 706.6 | 675.5 | 580.9 | 434.7 | 426.7 | 415.1 | 441.3 |
| SD - Radiesse + Sodium hydrogen carbonate [+250; +∞] HU | | | | | 58.6 | 62.5 | 38.5 | 34.4 | 64.9 | 99.7 | 62.9 |
| PC01 | 1097-01 | 500.0 | Radiesse + | 4 | 662.6 | 590.2 | 481.2 | 432.1 | 426.2 | 388.0 | 453.1 |
| PC01 | 1097-01 | | Trisodium | 9 | 713.2 | 674.1 | 532.7 | 479.2 | 451.5 | 401.5 | 441.7 |
| PC02 | 1097-02 | | Citrate | 5 | 720.5 | 713.8 | 617.5 | 429.1 | 445.0 | 388.0 | 421.7 |
| PC02 | 1097-02 | | Dihydrate | 10 | 748.3 | 692.4 | 566.4 | 398.4 | 415.8 | 352.0 | 385.1 |
| PC03 | 1097-03 | | | 1 | 711.3 | 658.2 | 492.0 | 419.0 | 458.3 | 424.4 | 432.8 |
| PC03 | 1097-03 | | | 6 | 714.2 | 684.3 | 490.7 | 441.5 | 491.8 | 458.6 | 475.9 |
| PC04 | 1097-04 | | | 2 | 748.6 | 727.9 | 615.8 | 488.4 | 613.6 | 578.5 | 569.7 |
| PC04 | 1097-04 | | | 7 | 747.1 | 698.9 | 589.2 | 487.9 | 523.6 | 550.5 | 530.0 |
| Mean - Radiesse + Trisodium Citrate Dihydrate [+250; +∞] HU | | | | | 720.7 | 680.0 | 548.2 | 447.0 | 478.2 | 442.7 | 463.7 |
| SD - Radiesse + Trisodium Citrate Dihydrate [+250; +∞] HU | | | | | 28.8 | 42.3 | 56.8 | 34.1 | 64.8 | 81.6 | 60.1 |

What is claimed is:

1. A method of treatment of a subject having undesired implanted tissue filler, which comprises administrating to the subject an effective amount of a hyperosmotic pharmaceutical composition consisting of an aqueous solution of NaCl by injection to a location containing the undesired amount or accumulation of implanted tissue filler.

2. The method of claim 1, wherein the implanted tissue filler is a calcium phosphate tissue filler.

3. The method of claim 1, wherein the hyperosmotic pharmaceutical composition has osmolality ranging from 1000 to 5000 milliosmol/kg.

4. The method of claim 1, wherein the hyperosmotic pharmaceutical composition is administered to the subject by intralesion injection.

5. The method of claim 1, wherein the hyperosmotic pharmaceutical composition is administered to the subject by one or more of deep dermal, subdermal, subcutaneous, intramuscular, or supraperiosteal injection.

6. The method of claim 4, wherein the volume ratio of the tissue filler in a lesion to the pharmaceutical composition injected into the lesion ranges from 5:1 to 1:5.

7. The method of claim 1, wherein the subject is a human.

8. The method of claim 1, wherein the hyperosmotic pharmaceutical composition is administered to the subject by intralesion injection, and wherein the volume ratio of implanted tissue filler to the pharmaceutical composition injected into the lesion ranges from 5:1 to 1:5.

9. The method of claim 1, wherein the hyperosmotic pharmaceutical composition has osmolality ranging from 2500 to 5000 milliosmol/kg.

10. The method of claim 1, wherein the administrating step results in in situ dilution of an amount of the undesired implanted tissue filler or results in reducing or redistributing an amount of the undesired implanted tissue filler.

11. The method of claim 8, wherein the hyperosmotic pharmaceutical composition has osmolality ranging from 2500 to 5000 milliosmol/kg.

12. The method of claim 8, wherein the administrating step results in in situ dilution of an amount of the undesired implanted tissue filler or results in reducing or redistributing an amount of the undesired implanted tissue filler.

13. The method of claim 1, wherein the hyperosmotic pharmaceutical composition is administered to the subject by intralesion injection, the volume ratio of implanted tissue filler to the pharmaceutical composition injected into the lesion ranges from 5:1 to 1:5, the hyperosmotic pharmaceutical composition has osmolality ranging from 2500 to 5000 milliosmol/kg and the administrating step results in in situ dilution of an amount of the undesired implanted tissue filler or results in reducing or redistributing an amount of the undesired implanted tissue filler.

* * * * *